(12) United States Patent
Chang et al.

(10) Patent No.: US 9,662,328 B2
(45) Date of Patent: May 30, 2017

(54) TARGETING HUMAN THYMIDYLATE KINASE INDUCES DNA REPAIR TOXICITY IN MALIGNANT TUMOR CELLS

(71) Applicants: NATIONAL YANG-MING UNIVERSITY, Taipei (TW); NATIONAL TAIWAN UNIVERSITY, Taipei (TW)

(72) Inventors: Zee-Fen Chang, Taipei (TW); Jim-Min Fang, Taipei (TW)

(*) Notice: Subject to any disclaimer, the term of this patent is extended or adjusted under 35 U.S.C. 154(b) by 0 days.

(21) Appl. No.: 15/015,878

(22) Filed: Feb. 4, 2016

(65) Prior Publication Data

US 2016/0151362 A1 Jun. 2, 2016

Related U.S. Application Data

(63) Continuation-in-part of application No. 13/990,398, filed as application No. PCT/CN2011/083103 on Nov. 29, 2011, now Pat. No. 9,278,982.

(60) Provisional application No. 61/417,648, filed on Nov. 29, 2010.

(51) Int. Cl.
| | |
|---|---|
| *A61K 31/496* | (2006.01) |
| *C07D 513/04* | (2006.01) |
| *A61K 31/704* | (2006.01) |
| *C07D 519/00* | (2006.01) |
| *C07D 275/04* | (2006.01) |
| *C07F 7/18* | (2006.01) |
| *A61K 31/695* | (2006.01) |
| *C07D 417/04* | (2006.01) |

(52) U.S. Cl.
CPC .......... *A61K 31/496* (2013.01); *A61K 31/695* (2013.01); *A61K 31/704* (2013.01); *C07D 275/04* (2013.01); *C07D 417/04* (2013.01); *C07D 513/04* (2013.01); *C07D 519/00* (2013.01); *C07F 7/1856* (2013.01)

(58) Field of Classification Search
None
See application file for complete search history.

(56) References Cited

U.S. PATENT DOCUMENTS

| | | |
|---|---|---|
| 3,965,107 A | 6/1976 | Rainey et al. |
| 5,776,925 A | 7/1998 | Young et al. |
| 2005/0049207 A1 | 3/2005 | Kaufmann |

FOREIGN PATENT DOCUMENTS

| | | |
|---|---|---|
| CN | 1185737 A | 6/1998 |
| CN | 1775025 A | 5/2006 |
| CN | 101427835 A | 5/2009 |
| JP | 2007210938 A | 8/2007 |
| KR | 20040014007 A | 2/2004 |
| PL | 180728 B1 | 3/2001 |
| PL | 185588 B1 | 6/2003 |

OTHER PUBLICATIONS

"Aurora Fine Chemicals", RN 902589-96-2, Database Registry Chemical Abstracts Service, Columbus, Ohio, Accession No. RN 902589-96-2, Entered STN: Aug. 18, 2006.*
Haouz et al. disclose in J. Biol. Chem. 278, 4963-4971 (2003).
K. Hirai et al., "Reactivity of Some Benzothiazepine Derivatives," Annu. Rep. Sankyo Res. Lab. 44, pp. 141-150 (1992).
C.M. Hu et al., "Synthetic Lethality by Lentiviral Short Hairpin RNA Silencing of Thymidylate Kinase and Doxorubicin in Colon Cancer Cells Regardless of the p53 Status," Cancer Res 2008; 68: 2831-2840, publ. online Apr. 15, 2008.
Speziale et al. In Journal of the American Chemical Society 78, 5580-5584 (1056).
Ito et al. In Cancer Science 94(1), 3-8 (2003).
"Aurora Fine Chemicals", RN 902872-75-7, Database Registry Chemical Abstracts Service, Columbus, Ohio, Accession No. RN 902872-75-7, Entered STN: Aug. 21, 2006.
Chun-Mei Hu et al., "Tumor Cells Require Thymidylate Kinase to Prevent dUTP Incorporation during DNA Repair", Cancer Cell 22, pp. 36-50, Jul. 10, 2012.

* cited by examiner

*Primary Examiner* — Dennis Heyer
(74) *Attorney, Agent, or Firm* — Muncy, Geissler, Olds & Lowe, P.C.

(57) ABSTRACT

The present invention relates to novel TMPK inhibitor and their methods of use. In particular, it relates to novel TMPK inhibitor of Formula (I) and therapeutics that decrease the cellular dTTP level to suppress the growth and inhibit DNA repair in tumor cells and acts as a novel chemosensitizer, which are useful in methods for treating or preventing cancers.

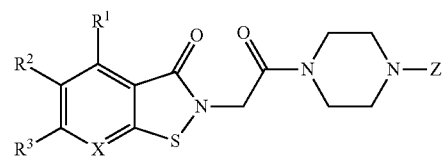

16 Claims, 6 Drawing Sheets
(3 of 6 Drawing Sheet(s) Filed in Color)

(A)

(B)

(C)

(A)

*: p=0.03 ; * *: p=0.001 ; * * *: p<0.0001

(B)

(C)

(D)

(A)

(B)

(C) MCF-7 cells  (D) MCF10A cells (E)

(A)

(B)

TARGETING HUMAN THYMIDYLATE KINASE INDUCES DNA REPAIR TOXICITY IN MALIGNANT TUMOR CELLS

CROSS REFERENCE TO RELATED APPLICATIONS

This application is a Continuation-in-Part of U.S. patent application Ser. No. 13/990,398, filed on May 29, 2013; and this application claims priority of U.S. Provisional Application No. 61/417,648 filed on Nov. 29, 2010, the entire contents of all of which are hereby incorporated by reference.

STATEMENT OF GOVERNMENT LICENSE RIGHTS

This invention was made with grants NHRI-EX-100-10005NI from National Health Research Institute, NSC 96-2628-B-002-079-MY2 from National Science Council, Taiwan and a grant from Aim for the Top University plan in National Yang-Ming University supported by the Ministry of Education, Taiwan.

FIELD OF THE INVENTION

The present invention relates to novel TMPK inhibitor and their methods of use. In particular, it relates to novel TMPK inhibitor, synthesis scheme, and therapeutics that impairs DNA repair in cancer but not non-tumorigenic cells. Such novel TMPK inhibitor and therapeutics may acts as novel chemosensitizers, and are useful in methods for treating or preventing cancers.

BACKGROUND OF THE INVENTION

Thymidylate kinase (TMPK) is a key enzyme for the phosphorylation of dTMP to dTDP, which is converted to dTTP by nucleotide diphosphate kinases (NDPKs) for DNA synthesis. Ribonucleotide reductase (RNR) is the enzyme essential for de novo synthesis of dNTPs. RNR-catalyzed reactions generate dADP, dGDP, dCDP and dUDP from the corresponding NDPs (Nordlund and Reichard, 2006). Therefore, dTDP is the only dNDP not directly derived from RNR reaction, but from TMPK reaction.

Conventional anti-cancer therapies often directly induce genotoxicity (Garg et al., 2010). For example, thymidylate synthase (TS) inhibitor, 5-FU or 5-FdUrd, blocks the conversion of dUMP to dTMP, causing dUTP to accumulate and 5-FdUTP formation (Longley et al., 2003). Since DNA polymerases cannot discriminate between dUTP and dTTP (Bessman et al., 1958; Mosbaugh, 1988), excessive amounts of dUTP and 5FdUTP are mis-incorporated into DNA, triggering genotoxicity-induced cell death (Ahmad et al., 1998). Consequently, such anti-metabolites produce excessive DNA damage due to erroneous nucleotide incorporation and causes cancer cells death while being highly toxic to normal cycling cells (Ahmad et al., 1998). In contrast, blocking TMPK does not cause dUTP accumulation, therefore the general cytotoxicity is much lower than TS inhibition (Hu et al, 2012)

It is known that double-strand breaks (DSBs) in proliferating cells are mainly repaired by homologous recombination (HR) in which the repair of a single DSB needs more than 10 thousands of dNTPs new incorporation (Robert et al., 2011; San Filippo et al., 2008). As such, RNR function in supply of dNTPs is critical for HR repair (Burkhalter et al., 2009). Of note, blocking RNR on its own induces DNA damage signal and replication stress (Helleday et al., 2008). Since dTDP formation specifically requires TMPK function, we showed that blocking TMPK decreases the efficiency of DSBs repair and sensitizes tumor cells to genotoxic insults (Hu et al., 2008, 2012)

Accordingly, inhibition of TMPK that blocks dTDP conversion from dTMP will inhibit DNA replication and repair that demand a large quantity of dTTP. Therefore, the TMPK inhibitor can be used for chemosensitization and inhibiting the growth of cancer. The TMPK inhibitor treatment has low general genotoxicity as compared to 5 FU or blocking dTMP formation.

The main problem with chemotherapy is the lack of differentiation between tumor- and rapidly-dividing cells in normal tissues. This causes substantial side effects, which can in the long run lead to secondary cancers induced by the treatment. Chemotherapeutic agents often cause unwanted general cytotoxicity, and activities of several DNA repair pathways enable tumor cells to survive by removing lesions (Helleday et al., 2008).

Small-molecule inhibitors of checkpoint pathways or DNA repair machineries were identified and used as cellular radio- and chemosensitization compounds in clinical trials (Bolderson et al., 2009). Given the differences in checkpoint and DNA repair alteration during tumorigenesis, the therapeutic efficacies of these strategies were found various depending on the checkpoint context of tumor (Jackson and Bartek, 2009; Jiang et al., 2009).

Moreover, derangement of DNA damage response could cause the accumulation of DNA error during therapy, which might provoke secondary tumor development (Mimeault et al., 2008). Therefore, it is important to develop a chemosensitization regimen that does not disrupt the checkpoint network while specifically inducing cancer cell death with little side effect.

SUMMARY OF THE INVENTION

The present invention provides novel compounds, their synthesis schemes and their methods of use. More particularly, the inventors have identified novel compounds and therapeutics comprising TMPK inhibitors and methods of use in treating or preventing cancers.

The present invention provides a compound for inhibiting thymidylate kinase (TMPK) comprising a therapeutically effective amount of Formula (I):

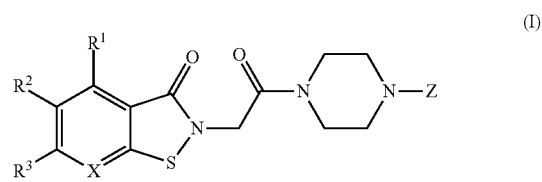

or a pharmaceutically acceptable salt thereof,
wherein
X is independently N or $CR^4$;
Z is H or Y-G
wherein
Y is $-C(=O)O$ or $-C(=O)CH_2$;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, —NHR$^B$, —NHC(=O)NHR$^B$, —N=C=O, or —N=C=S;

R$^1$, R$^2$, R$^3$ and R$^4$ is independently hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —SR$^A$, —NHR$^B$, —N(R$^B$)$_2$, —C(=O)R$^A$, —C(=O)OR$^A$, —OC(=O)R$^A$, —OCH$_2$C(=O)N(R$^B$)$_2$, —C(=O)NHR$^B$, —C(=O)N(R$^B$)$_2$, —NR$^B$C(=O)R$^A$, —OC(=O)N(R$^B$)$_2$, —NR$^B$C(=O)OR$^A$, —NR$^B$C(=O)N(R$^B$)$_2$, —S(=O)R$^A$, —OS(=O)$_2$R$^A$, —SO$_2$R$^A$, —NR$^B$SO$_2$R$^A$, —SO$_2$N(R$^B$)$_2$, or optionally substituted triazole;

wherein

R$^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

R$^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

or two R$^B$ taken together with the intervening nitrogen form optionally substituted heterocyclyl;

providing

Z is not —C(=O)OC$_2$H$_{50}$ or —C(=O)OC(CH$_3$)$_3$ when X, R$^1$, R$^2$, R$^3$, R$^4$ are simultaneously N, CH$_3$, H, CH$_3$ and H, respectively.

In some embodiments of the present invention, the compound is of Formula (I-a):

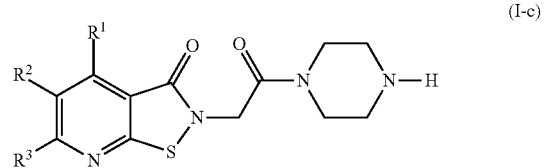

(I-a)

or a pharmaceutically acceptable salt thereof,
wherein
G, R$^1$, R$^2$ and R$^3$ are defined herein.

In some embodiments of the present invention, the compound is of Formula (I-b):

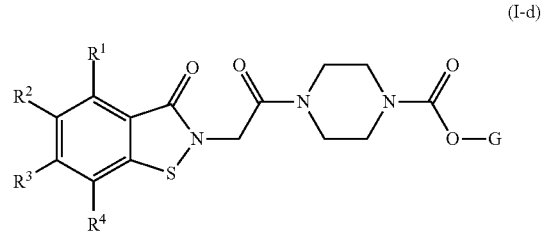

(I-b)

or a pharmaceutically acceptable salt thereof,
wherein
G, R$^1$, R$^2$ and R$^3$ are defined herein.

In some embodiments of the present invention, the compound is of Formula (I-c):

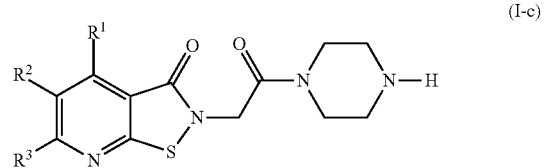

(I-c)

or a pharmaceutically acceptable salt thereof,
wherein
R$^1$, R$^2$ and R$^3$ are defined herein.

In some embodiments of the present invention, the compound is of Formula (I-d):

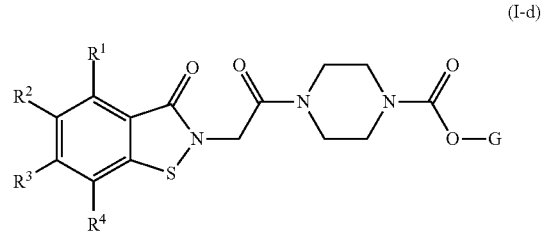

(I-d)

or a pharmaceutically acceptable salt thereof,
wherein
G, R$^1$, R$^2$, R$^3$ and R$^4$ are defined herein.

In some embodiments of the present invention, the compound is of Formula (I-e):

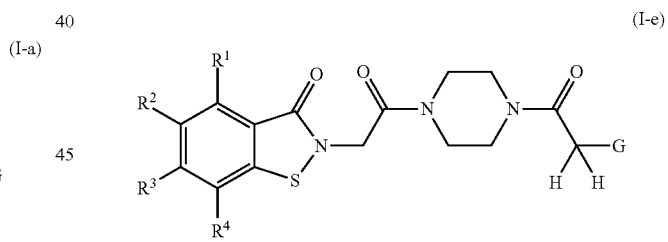

(I-e)

or a pharmaceutically acceptable salt thereof,
wherein
G, R$^1$, R$^2$, R$^3$ and R$^4$ are defined herein.

In some embodiments of the present invention, the compound is of Formula (I-f):

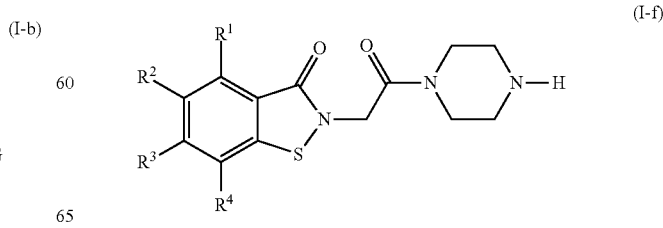

(I-f)

or a pharmaceutically acceptable salt thereof, wherein
R$^1$, R$^2$, R$^3$ and R$^4$ are defined herein.

In some embodiments, the compounds of the present invention are capable of inhibiting TMPK activity. In other embodiments, the compounds of the present invention are capable of inhibiting cellular dTTP levels. In some embodiments, the compounds of the present invention are capable of inhibiting tumor growth, DNA damage checkpoint, DNA mismatch repair, nucleotide excision repair, double-strand break repair, DNA helicase function, signaling, cell cycle control or apoptosis.

In some embodiments, the double-strand break repair may be associated with chemotherapy. In some embodiments, the chemotherapy involves treatment with doxorubicin.

In some embodiments, the compositions of the present invention selectively target toxicity to cancer cells with DNA lesions.

In other embodiments, the compositions of the present invention are capable of sensitizing cancer cells to chemotherapy. In some embodiments, the chemotherapy involves treatment with doxorubicin.

In some embodiments, the compositions of the present invention do not result in genotoxic side effects.

The present invention further provides a pharmaceutical composition comprising a composition described herein and a pharmaceutically acceptable carrier.

The present invention also provides a method for manufacturing a composition as described in the section of Methods of Invention.

The present invention also provides a method for sensitizing cancer cells to the therapeutic effects of chemotherapy comprising exposing the cancer cells to an effective amount of an agent that inhibits TMPK activity. In some embodiments, the agent is a composition of the present invention.

The present invention further provides a method of preventing double-strand break repair of cancer cells comprising exposing the cancer cells to an effective amount of a composition of the present invention.

The present invention also provides a method of selectively targeting toxicity to cancer cells with DNA lesions comprising exposing the cancer cells to an effective amount of a composition of the present invention.

In some embodiments, the cancer cell is selected from the group consisting of a breast cancer cell, a hepatoma cell, a colorectal cancer cell, pancreatic carcinoma cell, an esophageal carcinoma cell, a bladder cancer cell, an ovarian cancer cell, a skin cancer cell, a liver carcinoma cell, a gastric cancer cell, a prostate cancer cell, a colon cancer cell, a lung cancer cell, a rectal cancer cell, a renal cancer cell, a thyroid cancer cell, a brain cancer cell, melanoma, sarcoma, leukemia, bone cancer cell and endometrial cancer cell.

In some embodiments, the methods further comprise exposing the cancer cells to at least one additional therapeutic agent selected from the group consisting of anticancer agents, antiviral agents, anti-inflammatory agents and immunosuppressive agents.

The present invention also provides a method of treating or preventing cancer in a subject in need thereof, comprising administering to the subject a therapeutically effective amount of a composition of the present invention.

In some embodiments, the anti-cancer therapy is administered prior to administration of the composition. In some embodiments, the anti-cancer therapy is administered simultaneously with administration of the composition.

In some embodiments, the cancer is selected from the group consisting of breast cancer, hepatoma, colorectal cancer, pancreatic carcinoma, esophageal carcinoma, bladder cancer, ovarian cancer, skin cancer, liver carcinoma, gastric cancer, prostate cancer, colon cancer, lung cancer, rectal cancer, renal cancer, thyroid cancer, brain cancer, melanoma, sarcoma, leukemia, bone cancer and endometrial cancer.

In some embodiments, the subject is a mammal.

These and other features, aspects and advantages of the present invention will become better understood with reference the following description, examples and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
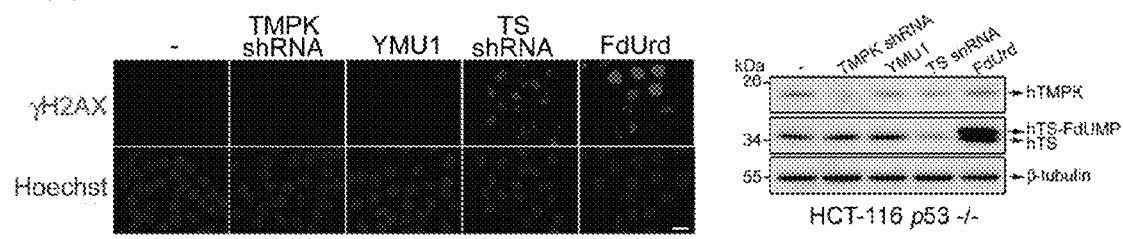
FIG. 1. TMPK knockdown has no genotoxicity but promoting doxorubicin-induced cell death in p53 proficient and deficient colon cancer cells. (A) HCT-116 p53$^{-/-}$ cells were infected with lentiviral shRNA of TMPK or TS. In parallel, cells were treated with YMU1 (2 μM) for 2 days, or 5-fluoro-2'deoxyuridine (FdUrd, 2 μM) for 1 day. These cells were fixed for γH2AX foci staining to indicate DNA damage and Western blotting analysis. (B-C) FITC-labeled annexin V apoptosis assay. (B) p53(+/+) HCT-116 were and (−/−) HCT-116 cells were infected with or without lentiviral TMPK$^{shRNA}$ for 72 hr, treated with 0.5 μM doxorubicin for 24 hr (C) Cells were with or without lentiviral TS$^{shRNA}$ for 72 hr with a subsequent 1 μM doxorubicin treatment for 24 hr as indicated Cells were then stained with FITC-labeled annexin V and observed by fluorescent microscopy. Green-positive indicates apoptotic cell.
Figure 1:
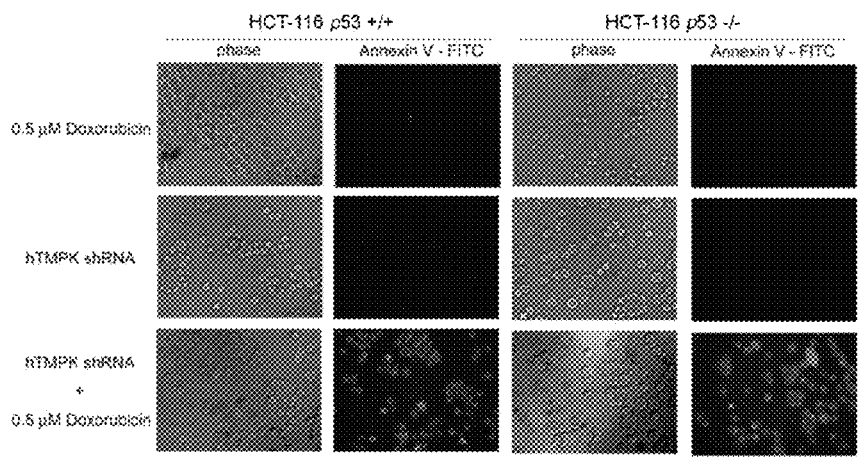
Figure 1:
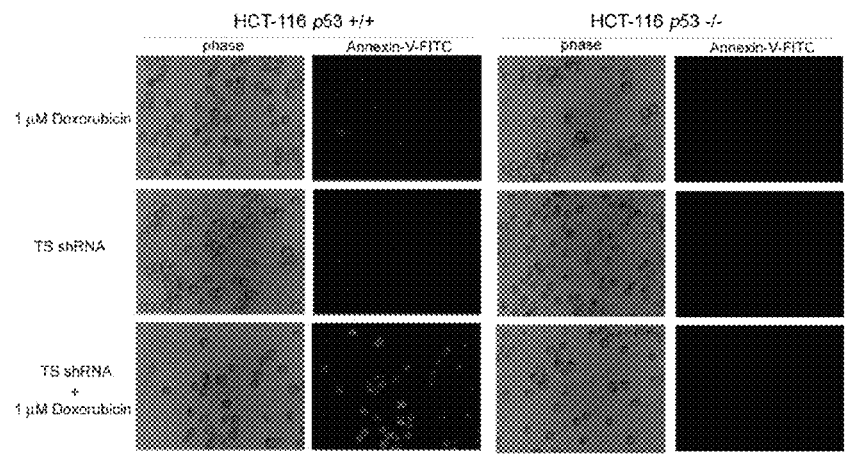

Unless otherwise defined, all technical terms used herein have the same meaning as commonly understood by one of ordinary skill in the art to which this invention belongs.

To facilitate understanding of the present application and for ease of reference, a number of terms and abbreviations as used herein are defined below.

As used herein, the terms "treating" and "treatment" are used to refer to administration or application of a therapeutic agent to a subject or performance of a procedure or modality on a subject for the purpose of obtaining a therapeutic benefit of a disease or health-related condition.

As used herein, the terms "preventing," "inhibiting," "reducing" or any variation of these terms, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99% or more, or any range derivable therein, reduction of activity or symptoms, compared to normal.

As used herein, the terms "administered" and "delivered" are used to describe the process by which a composition of the present invention is administered or delivered to a subject, a target cell or are placed in direct juxtaposition with the target cell. The terms "administered" and "delivered" are used interchangeably.

As used herein, the terms "patient," "subject" and "individual" are used interchangeably herein, and mean a mammalian (e.g., human) subject to be treated and/or to obtain a biological sample from.

As used herein, the term "effective" means adequate to accomplish a desired, expected, or intended result. For example, an "effective amount" may be an amount of a compound sufficient to produce a therapeutic benefit.

As used herein, the terms "therapeutically effective" or "therapeutically beneficial" refers to anything that promotes or enhances the well-being of the subject with respect to the medical treatment of a condition. This includes, but is not limited to, a reduction in the onset, frequency, duration, or severity of the signs or symptoms of a disease.

As used herein, the term "therapeutically effective amount" is meant an amount of a composition as described herein effective to yield the desired therapeutic response.

As used herein, the terms "diagnostic," "diagnose" and "diagnosed" mean identifying the presence or nature of a pathologic condition.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used as described herein.

The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, the term "alkyl" (alone or in combination with another term(s)) refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. When the lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, or tert-butyl, and the like. The alkyl group may be substituted or unsubstituted. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl)thio, arylthio optionally substituted with one or more groups, preferably one, two or three groups which are independently of each other halo, hydroxy, unsubstituted lower alkyl or alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $RS(O)$—, $RS(O)_2$—, —C(O)OR, RC(O)O—, and —$NR_{13}R_{14}$, wherein $R_{13}$ and $R_{14}$ are independently selected from the group consisting of hydrogen, unsubstituted lower alkyl, trihalomethyl, cycloalkyl, heterocyclic and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heterocyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —$NR_{13}R_{14}$, wherein $R_{13}$ and $R_{14}$ are independently selected from the group consisting of hydrogen and alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, triazinyl, and the like.

As used herein, the term "aromatic", "ar" or "aryl" (alone or in combination with another term(s)) refer to aromatic cyclic groups (for example 6 membered monocyclic, 10 membered bicyclic or 14 membered tricyclic ring systems) which contain 6 to about 14 carbon atoms. Exemplary aromatic groups include phenyl, naphthyl, biphenyl, indenyl, and anthracene.

As used herein, the term "halogen" (alone or in combination with another term(s)) refers to a fluorine substituent ("fluoro," which may be depicted as —F), chlorine substituent ("chloro," which may be depicted as —Cl), bromine substituent ("bromo," which may be depicted as —Br), or iodine substituent ("iodo," which may be depicted as —I).

As used herein, the term "cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heterocyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl)thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$ are as defined above.

As used herein, the term "alkenyl" (alone or in combination with another term(s)) refers to a lower alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like.

As used herein, the term "alkynyl" (alone or in combination with another term(s)) refers to a lower alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Heterocyclic" refers to a monocyclic or fused ring group having in the ring(s) of 5 to 9 ring atoms in which one or two ring atoms are heteroatoms selected from N, O, or S(O)n (where n is an integer from 0 to 2), the remaining ring atoms being C. The rings may also have one or more double bonds. However, the rings do not have a completely conjugated pi-electron system. Examples, without limitation, of unsubstituted heterocyclic groups are pyrrolidino, piperidino, piperazino, morpholino, thiomorpholino, homopiperazino, and the like. The heterocyclic ring may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl) thio, cyano, acyl, thioacyl, O-carbamyl, N-carbamyl, O-thiocarbamyl, N-thiocarbamyl, C-amido, N-amido, nitro, N-sulfonamido, S-sulfonamido, RS(O)—, RS(O)$_2$—, —C(O)OR, RC(O)—, and —NR$_{13}$R$_{14}$, with R$_{13}$ and R$_{14}$ as defined above. Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

Preferably, the heterocyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

As used herein, the term "Hydroxy" refers to an —OH group.

As used herein, the term "Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

As used herein, the term "Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

The terms "heterocycle", "heterocyclic" or "heterocyclo" (alone or in combination with another term(s)) refer to fully saturated (i.e., "heterocycloalkyl"), non-aromatic partially-saturated (i.e., "heterocycloalkenyl"), or heterocyclic aromatic (i.e. "heteroaryl") ring structure, typically having 3 to about 20 carbon atoms, more typically having 3 to about 14 carbon atoms. For example, the heterocyclic group may a 4 to about 7 membered monocyclic ring systems, a 7 to about 11 membered bicyclic ring systems, or a 10 to about 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyi"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

A heterocyclyl alternatively may be from 2 to 5 (more typically from 2 or 3) rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the multi-ring heterocyclyls are indolizinyl, pyranopyrrolyl, purinyl, pyridopyridinyl, pyrindinyl, and 4H-quinolizinyl.

Exemplary bicyclic heterocyclic groups include indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl," "thionaphthenyl," and "benzothiofuranyl"), isobenzothienyl (also known as "isobenzothiophenyl," "isothionaphthenyl," and "isobenzothiofuranyl"), benzothiazolyl, benzoisothiazolyl, benzothiadiazolyl, benzoxadiazolyl, indolyl, isoindazolyl (also known as "benzopyrazolyl"), benzoimidazolyl, benzotriazolyl, benzazinyl (including quinolinyl (also known as "l-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

As used herein, the term "heteroaryl" (alone or in combination with another term(s)) refers to an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the 5-membered rings include furanyl, thienyl, oxazolyl, isoxazolyl, thiazolyl, isothiazolyl, oxadiazolyl, pyrazolyl, and imidazolyl; the 6-membered rings include pyridinyl, pyrazinyl, pyrimidinyl, pyridazinyl, and triazinyl; the 6/5-membered fused-ring systems include benzoxazolyl, benzoisoxazolyl, anthranilyl, benzothienyl, isobenzothienyl, and purinyl; and the 6/6-membered fused-ring systems include quinolinyl, isoquinolinyl, and benzodiazinyl.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

As used herein, the term "hydrogen" (alone or in combination with another term(s)) refers to a hydrogen substituent and may be depicted as —H.

As used herein, the term "hydroxy" (alone or in combination with another term(s)) refers —OH.

As used herein, the term "nitro" (alone or in combination with another term(s)) refers to —NO$_2$.

As used herein, the term "substitution" refers to a compound having a substituent comprising at least one carbon, nitrogen, oxygen, or sulfur atom that is bonded to one or more hydrogen atoms. If a substituent is described as being "substituted," a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

As used herein, the terms "contacted" and "exposed" when applied to a cell, are used to describe the process by which a compound of the present invention is administered or delivered to a target cell or are placed in direct juxtaposition with the target cell. The terms "administered" and "delivered" are used interchangeably with "contacted" and "exposed".

If a substituent is described as being "optionally substituted," the substituent is either (1) substituted, or (2) not substituted. When the members of a group of substituents are described generally as being optionally substituted, any atom capable of substitution in each member of such group may be (1) substituted, or (2) not substituted. Such a characterization contemplates that some members of the group are not substitutable. Atoms capable of substitution include, for example, carbon bonded to at least one hydrogen, oxygen bonded to at least one hydrogen, sulfur bonded to at least one hydrogen, or nitrogen bonded to at least one hydrogen. On the other hand, hydrogen alone, halogen, oxo, and cyano do not fall within the definition of being capable of substitution.

Although methods and compositions similar or equivalent to those described herein can be used in the practice or testing of the present invention, suitable methods and compositions are described below.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The particular embodiments discussed below are illustrative only and not intended to be limiting.

TMPK and TMPK Inhibitors

The present invention is directed to novel compositions and therapeutics comprising TMPK inhibitors and methods of use in treating or preventing cancers. Thymidylate kinase (TMPK) is important for dTDP formation, while dADP, dGDP, dCDP and dUDP can be directly produced in reactions catalyzed by ribonucleotide reductase (RNR). Cancer cells express high level of RNR, which is composed of R1 and R2 subunit or R1/p53R2 subunit, and require the coupling of TMPK reaction to provide a balanced four dNTP pool for DNA synthesis. The present invention is based on that inhibition of TMPK decreases dTTP formation, thereby suppressing tumor growth and cell survival from genotoxic insult due to the deficiency in DNA repair.

Using RNA interference, the present invention provides that TMPK knockdown significantly increases the doxorubicin sensitivity of HCT-116 colon cancer cells regardless of p53 status (Hu and Chang, 2008). Doxorubisin is a topoisomerase II inhibitor that induces DNA (DSBs), In comparison, TS knockdown has a rather limiting effect in sensitizing p53-deficient cells to doxorubicin because of the complementation of TK-mediated dTMP formation. Importantly, the present invention provides that TMPK knockdown does not, on its own, activate DNA damage responses. It thus functions in a way that is quite distinct from that of anti-metabolites used in conventional anti-cancer therapies, which directly induce genotoxicity (Garg et al., 2010).

TMPK knockdown causes some cancer cells with slower growth rate, but the effect is not obvious for non-tumorigenic cells. Thus, the present invention provides that the context of R2 elevation makes TMPK as the Achilles heel in tumor cells.

The present invention provides the identification of novel inhibitors of TMPK, which suppresses the growth and sensitizes tumor cells to doxorubicin without expanding the extent of genotoxicity. Thus, the novel inhibitors described in the present invention provide a new opportunity in developing mild anti-cancer therapies that can prime tumor cells to sublethal doses of doxorubicin treatment to achieve lethality while having minimal side effects in normal cycling cells.

Accordingly, the present invention provides novel TMPK inhibitors that are useful in the treatment or prevention of cancer.

In one embodiment of the present invention, a composition for inhibiting thymidylate kinase (TMPK) comprising a therapeutically effective amount of Formula (I) is provided:

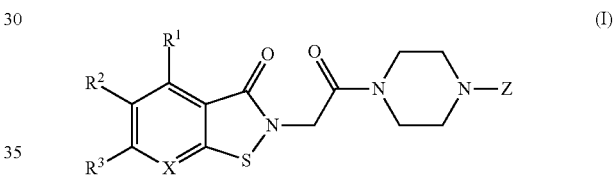

or a pharmaceutically acceptable salt thereof,
wherein
X is independently N or $CR^4$;
Z is H or Y-G
wherein
Y is $-C(=O)O$ or $-C(=O)CH_2$;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, $-NHR^B$, $-NHC(=O)NHR^B$, $-N=C=O$, or $-N=C=S$;
$R^1$, $R^2$, $R^3$ and $R^4$ is independently hydrogen, halogen, $-CN$, $-NO_2$, $-N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, $-OR^A$, $-SR^A$, $-NHR^B$, $-N(R^B)_2$, $-C(=O)R^A$, $-C(=O)OR^A$, $-OC(=O)R^A$, $-OCH_2C(=O)N(R^B)_2$, $-C(=O)NHR^B$, $-C(=O)N(R^B)_2$, $-NR^BC(=O)R^A$, $-OC(=O)N(RB)_2$, $-NR^BC(=O)OR^A$, $-NR^BC(=O)N(RB)_2$, $-S(=O)R^A$, $-OS(=O)_2R^A$, $-SO_2R^A$, $-NR^BSO_2R^A$, $-SO_2N(R^B)_2$, or optionally substituted triazole;
wherein
$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
or two $R^B$ taken together with the intervening nitrogen form optionally substituted heterocyclyl;
providing
Z is not —C(=O)OC$_2$H$_5$ or —C(=O)OC(CH$_3$)$_3$ when X, $R^1$, $R^2$, $R^3$ and $R^4$ are simultaneously N, CH$_3$, H, CH$_3$ and H, respectively.

In some embodiments of the present invention, the compound is of Formula (I-a):

(I-a)

or a pharmaceutically acceptable salt thereof,
wherein
G, $R^1$, $R^2$ and $R^3$ are defined herein.

In some embodiments of the present invention, the compound is of Formula (I-b):

(I-b)

or a pharmaceutically acceptable salt thereof,
wherein
G, $R^1$, $R^2$ and $R^3$ are defined herein.

In some embodiments of the present invention, the compound is of Formula (I-c):

(I-c)

or a pharmaceutically acceptable salt thereof,
wherein
$R^1$, $R^2$ and $R^3$ are defined herein.

In some embodiments of the present invention, the compound is of Formula (I-d):

(I-d)

or a pharmaceutically acceptable salt thereof,
wherein
G, $R^1$, $R^2$, $R^3$ and $R^4$ are defined herein.

In some embodiments of the present invention, the compound is of Formula (I-e):

(I-e)

or a pharmaceutically acceptable salt thereof,
wherein
G, $R^1$, $R^2$, $R^3$ and $R^4$ are defined herein.

In some embodiments of the present invention, the compound is of Formula (I-f):

(I-f)

or a pharmaceutically acceptable salt thereof,
wherein
$R^1$, $R^2$, $R^3$ and $R^4$ are defined herein.

In some embodiments of the present invention, the compound comprises the structures shown in Table 1:

TABLE 1

G is C$_n$H$_{2n+1}$, CH$_2$Ph, CH$_2$CH=CH$_2$; wherein n = 1-6.

TABLE 1-continued

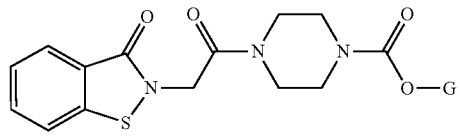

G is $C_nH_{2n+1}$, $CH_2Ph$, $CH_2CH=CH_2$; wherein n = 1-6

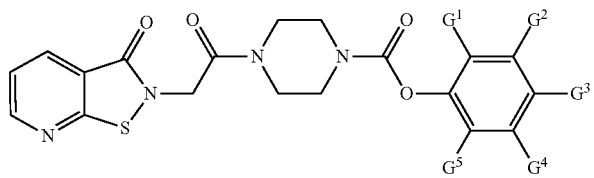

$G^1$, $G^2$, $G^3$, $G^4$ and $G^5$ is independently F, Cl, Br, I, CN, $NO_2$, $N_3$, $C_nH_{2n+1}$, $OC_nH_{2n+1}$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$; wherein n = 0-4.

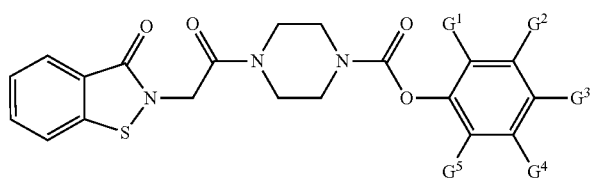

$G^1$, $G^2$, $G^3$, $G^4$ and $G^5$ is independently F, Cl, Br, I, CN, $NO_2$, $N_3$, $C_nH_{2n+1}$, $OC_nH_{2n+1}$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$; wherein n = 0-4.

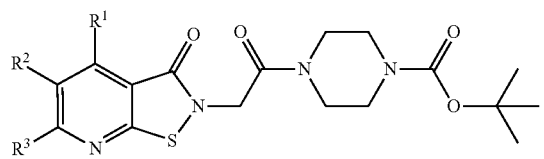

$R^1$, $R^2$ and $R^3$ is independently F, Cl, Br, I, CN, $NO_2$, $N_3$, $C_nH_{2n+1}$, $OC_nH_{2n+1}$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$; wherein n = 0-4.

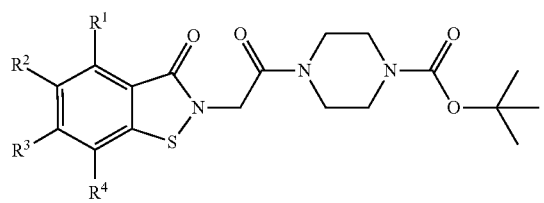

$R^1$, $R^2$, $R^3$, $R^4$ is independently F, Cl, Br, I, CN, $NO_2$, $N_3$, $C_nH_{2n+1}$, $OC_nH_{2n+1}$, $OSi(C_nH_{2n+1})_3$, $OSiMe_2(t-Bu)$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$; wherein n = 0-4.

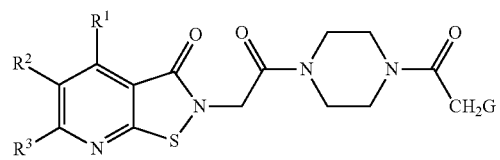

$R^1$, $R^2$ and $R^3$ is independently F, Cl, Br, I, CN, $NO_2$, $N_3$, $C_nH_{2n+1}$, $OC_nH_{2n+1}$, $NHC_nH_{2n+1}$, $N(C_nH_{2n+1})_2$; G is F, Cl, Br, I, $N_3$, $NH_2$, $N=C=S$, $N=C=O$, $NH(C=O)C_nH_{2n+1}$, $NH(C=O)Ar$, $NH(C=O)OC_nH_{2n+1}$, $NH(C=O)OAr$, $NH(C=O)NHC_nH_{2n+1}$, $NH(C=O)NHAr$; wherein Ar is optionally substituted phenyl; n = 0-4.

TABLE 1-continued

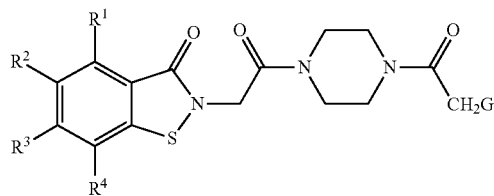

R¹, R², R³, R⁴ is independently F, Cl, Br, I, CN, NO₂, N₃, $C_nH_{2n+1}$, $OC_nH_{2n+1}$, $NHC_2H_{2n+1}$, $N(C_nH_{2n+1})_2$; G is F, Cl, Br, I, N₃, NH₂, N=C=S, N=C=O, NH(C=O)$C_nH_{2n+1}$, NH(C=O)Ar, NH(C=O)O$C_nH_{2n+1}$, NH(C=O)OAr, NH(C=O)NH$C_nH_{2n+1}$, NH(C=O)NHAr; wherein Ar is optionally substituted phenyl; n = 0-4.

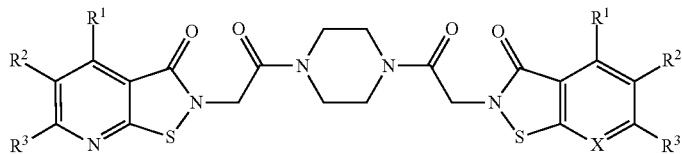

X is N or CR⁴;
R¹, R², R³, R⁴ is independently F, Cl, Br, I, N₃, $C_nH_{2n+1}$, $OC_nH_{2n+1}$, $NHC_nH_{2n+1}$, $N(C_nH_{2n+1})_2$; wherein n = 0-4.

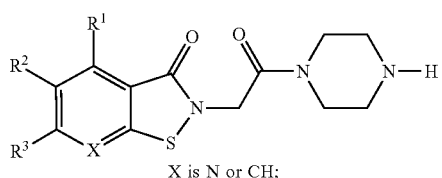

X is N or CH;
R¹, R² and R³ is independently F, Cl, Br, I, CN, NO₂, N₃, $C_nH_{2n+1}$, $OC_nH_{2n+1}$, $OSi(C_nH_{2n+1})_3$, $OSiMe_2$(t-Bu), $SC_nH_{2n+1}$, $NHC_nH_{2n+1}$, $N(C_nH_{2n+1})_2$, $O(C=O)C_nH_{2n+1}$, NH(C=O)$C_nH_{2n+1}$, C(=O)$C_nH_{2n+1}$, C(=O)O$C_nH_{2n+1}$, C(=O)NH$C_nH_{2n+1}$, $SO_2C_nH_{2n+1}$; wherein n = 0-4.

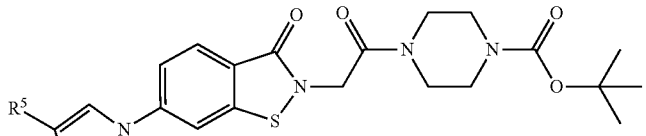

R⁵ is $C_nH_{2n+1}$, C(=O)$C_nH_{2n+1}$, C(=O)O$C_nH_{2n+1}$, C(=O)NH$C_nH_{2n+1}$, $SO_2C_nH_{2n+1}$ or optionally substituted phenyl; wherein n = 0-4.

In some embodiments of the present invention, the compound comprises at least one of the following structures:

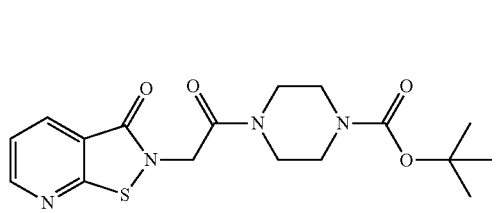

I-a-1

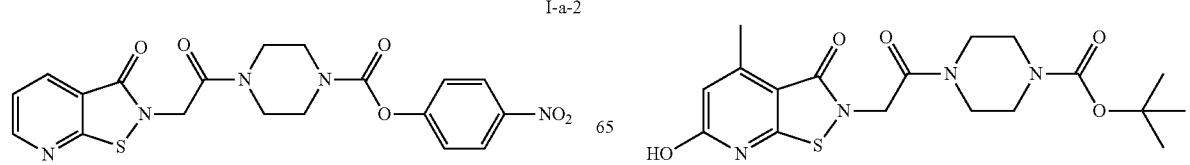

I-a-2

-continued

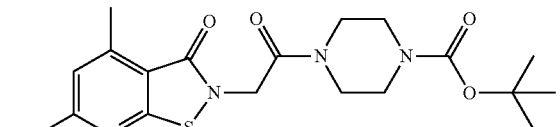

I-a-3

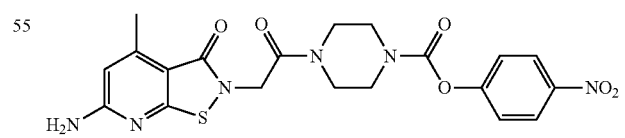

I-a-4

I-a-5

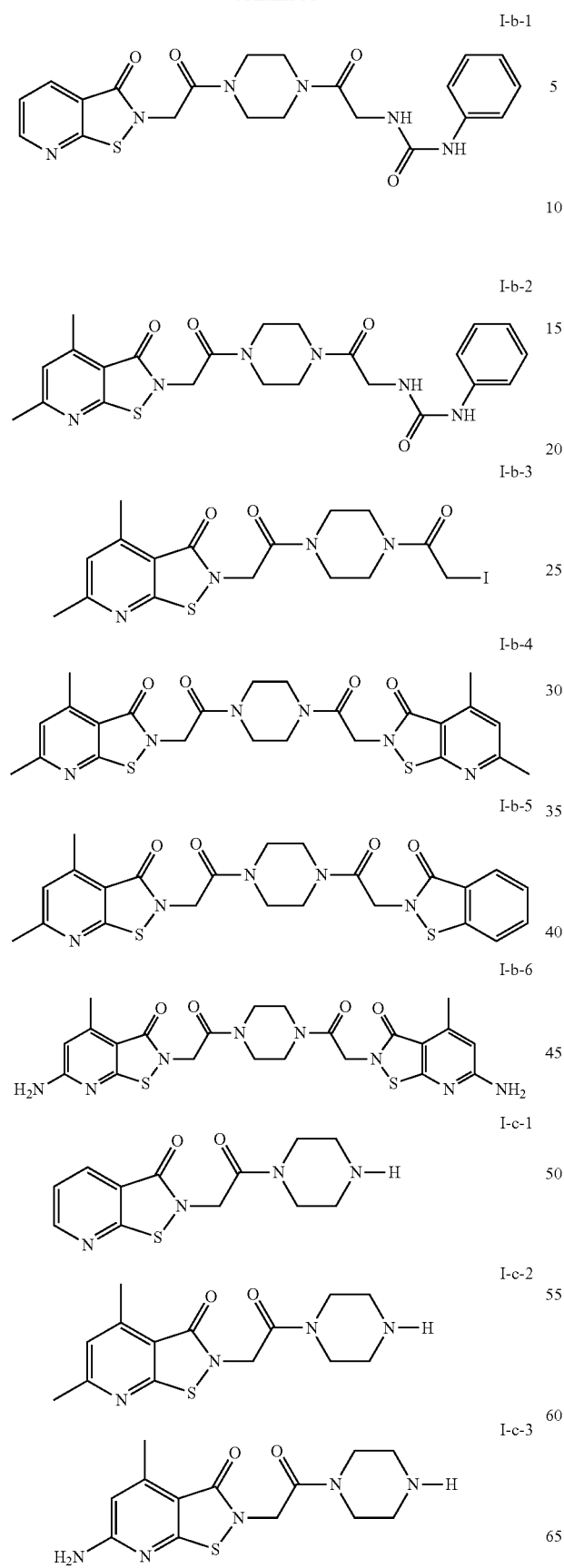

-continued
I-d-10
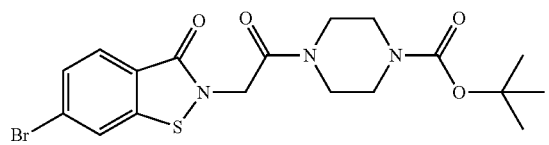
I-d-11
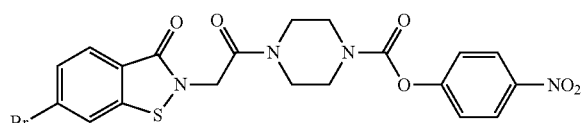
I-d-12
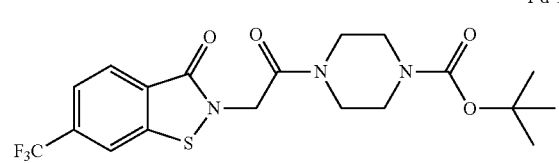
I-d-13
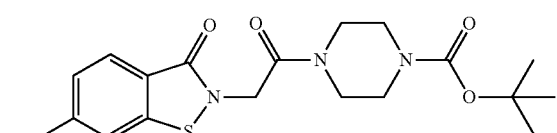
I-d-14
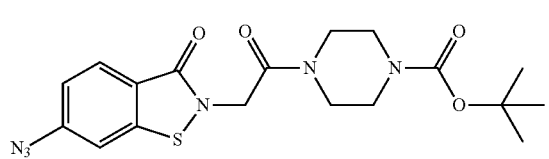
I-d-15
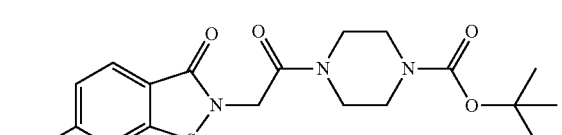
I-d-16
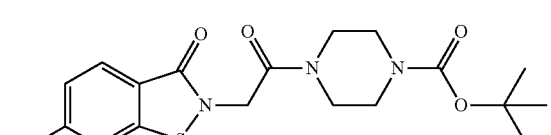
I-d-17
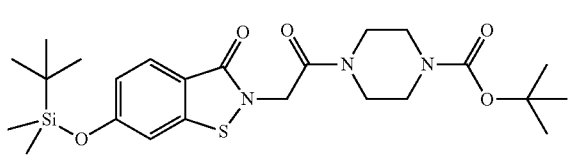
I-d-18
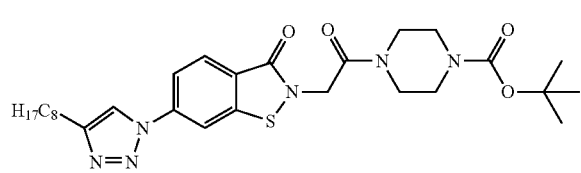
-continued
I-d-19
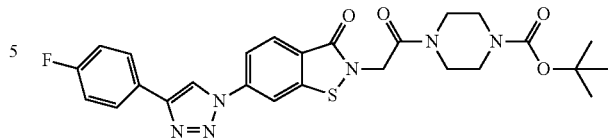
I-e-1
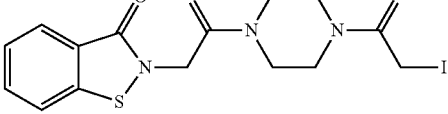
I-e-2
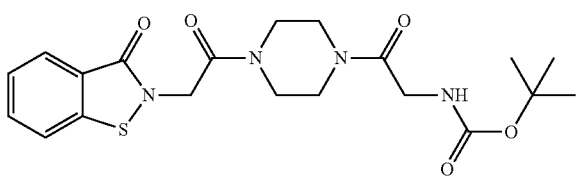
I-e-3
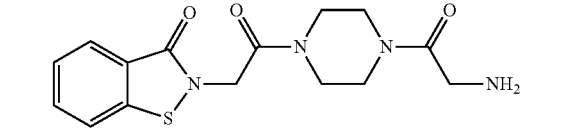
I-e-4
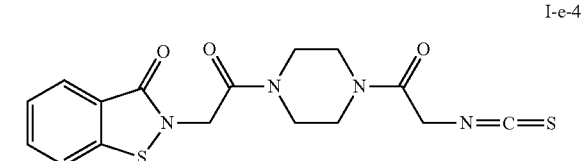
I-e-5
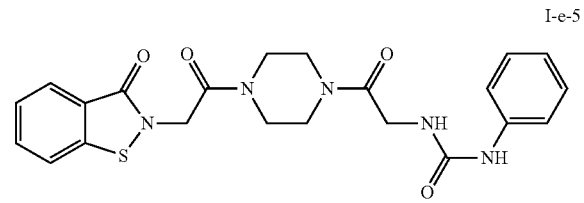
I-e-6
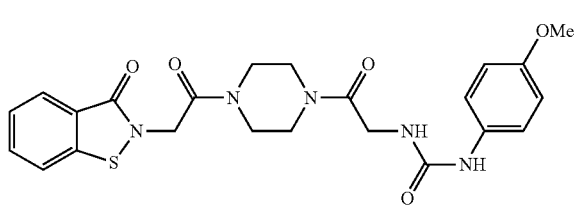
I-e-7
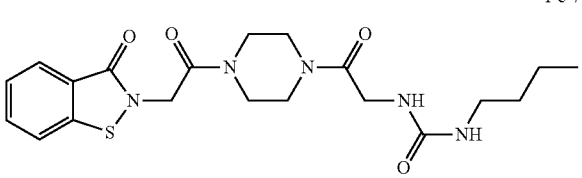
I-e-8
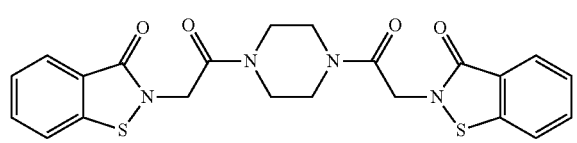

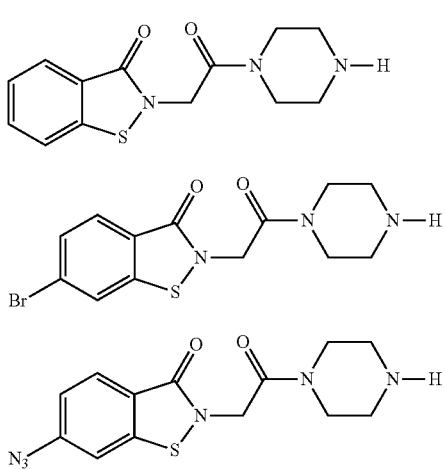

In some embodiments, the compounds of the present invention are capable of inhibiting TMPK activity.

In other embodiments, the compounds of the present invention are capable of inhibiting cellular dTTP formation. In some embodiments, the compounds of the present invention are capable of inhibiting tumor growth, DNA double-strand break repair, DNA mismatch repair, nucleotide excision repair, cell cycle control or apoptosis.

In particular, the double-strand break repair may be associated with chemotherapy.

In some cases, the chemotherapy involves treatment with doxorubicin.

In some embodiments, the compounds of the present invention selectively target toxicity to cancer cells with DNA lesions.

In other embodiments, the compounds of the present invention are capable of sensitizing cancer cells to chemotherapy. In some embodiments, the chemotherapy involves treatment with doxorubicin.

In some embodiments, the compounds of the present invention do not result in genotoxic side effects.

In some embodiments, the compounds of the present invention exhibit an $IC_{50}$ value of about 10 µM or less. In some embodiments, they exhibit an $IC_{50}$ value of about 5 µM or less. In some embodiments, the compositions exhibit an $IC_{50}$ value of about 1 µM or less. In some embodiments, the compounds exhibit an $IC_{50}$ value of about 0.5 µM or less. In still other embodiments, the compositions exhibit an $IC_{50}$ value of about 0.25 µM or less. In other embodiments, the compositions exhibit an $IC_{50}$ value of about 0.1 µM or less.

As illustrated in the Examples section, the present application provides new insights into the functional requirement of TMPK for DNA repair in tumor cells. This requirement specifically involves elevation of R2 expression in tumor cells after DNA damage.

Accordingly, the present application provides that blocking TMPK reduces the rate of dTTP formation. Since tumor cells contain elevated function of RNR, blocking of TMPK function causes the unbalanced dTTP formation, thus specifically sensitizing tumor cells to doxorubicin.

Expression of R2 subunit of RNR is cell-cycle regulated, peaking in the S and G2/M phases (Ladner and Caradonna, 1997; Nordlund and Reichard, 2006). It is well established that malignant cells have cell cycle checkpoint defects (Kastan and Bartek, 2004). Therefore, these tumor cells during recovery from DNA damage have more population distribution in S and G2/M phase and the level of R2 is high.

The high RNR function requires TMPK for dTTP formation to give a balanced dNTP pool for DNA repair. Inhibition of TMPK thereby upsets the dNTP balance, thus inhibiting DNA repair in tumor cells. In contrast, the S phase population was decreased in normal cycling H184B5F5/M10 cells during recovery from DNA damage probably due to the presence of intact checkpoint. As a result, these normal cycling cells expressed even less amount R2, which might further limit dUDP formation and inhibition of TMPK has less effect on the balanced dNTP pool and DNA repair. It should be mentioned that expression of R2 up-regulated in many types of cancer cells in patients (Jensen et al., 1994; Okumura et al., 2005; Yanamoto et al., 2003; Zhang et al., 2009). Therefore, the use of TMPK inhibition in sensitizing tumors to genotoxic agents is promising.

The present findings rationalize that the context of R2 elevation makes TMPK as Achilles heel in tumor for doxorubicin sensitization. The present application provides that TMPK inhibition does not produce genotoxic effects in cells. 5-FU and 5-FdUrd, the most commonly used chemotherapeutic agents, inhibit TS, which converts dUMP to dTMP in the de novo synthesis pathway, and further impair cell function through erroneous nucleotide misincorporation into RNA and DNA (Longley et al., 2003). Although TS inhibitors and other nucleotide metabolite blockers have also been used as chemosensitizers (Garg et al., 2010), it should be emphasized that these anti-cancer agents are toxic to genomic DNA in normal cycling cells. Their therapeutic effect stems solely from their ability to cause extensive DNA damage, so they produce non-specific toxicity. We propose that the therapeutic advantage of TMPK inhibitors of the present invention over these conventional compounds is their specific toxicity to malignant cells with DNA lesions.

Therapeutic Uses

The present invention provides a method of suppressing the cellular growth, sensitizing cancer cells to chemotherapy comprising exposing the cancer cells to an effective amount of a TMPK inhibitor of the present invention. In some embodiments, the TMPK inhibitor of the present invention selectively target toxicity to cancer cells with DNA lesions. In some embodiments, the TMPK inhibitor of the present invention does not result in genotoxic side effects.

The present invention also provides a method for sensitizing cancer cells to the therapeutic effects of chemotherapy comprising exposing the cancer cells to an effective amount of an agent that inhibits TMPK activity. In some embodiments, the agent is a TMPK inhibitor of the present invention.

The present invention also provides a method of preventing double-strand break repair of cancer cells comprising exposing the cancer cells to an effective amount of a TMPK inhibitor of the present invention.

The present invention also provides a method of selectively targeting toxicity to cancer cells with DNA lesions comprising exposing the cancer cells to an effective amount of a TMPK inhibitor of the present invention.

In some embodiments, the cancer cell is selected from the group consisting of a breast cancer cell, a hepatoma cell, a colorectal cancer cell, pancreatic carcinoma cell, an esophageal carcinoma cell, a bladder cancer cell, an ovarian cancer cell, a skin cancer cell, a liver carcinoma cell, a gastric cancer cell, a prostate cancer cell, a colon cancer cell, a lung cancer cell, a rectal cancer cell, a renal cancer cell, a thyroid cancer cell, a brain cancer cell, melanoma, sarcoma, leukemia, a bone cancer cell and endometrial cancer cell.

In some embodiments, the present invention provides that the cancer cells are further exposed to at least one additional therapeutic agent selected from the group consisting of anti-cancer agents, antiviral agents, anti-inflammatory agents and immunosuppressive agents.

Anti-cancer agents contemplated within the present invention include, but are not limited to, microtubule interference agents, topoisomerase inhibitors, alkylating agents, thymidylate synthase inhibitors, anti-metabolites, pyrimidine antagonists, purine antagonists, ribonucleotide reductase inhibitors, and kinase inhibitors. In some embodiments, microtubule interference agents are those agents which induce disorganized microtubule formation, disrupting mitosis and DNA synthesis and include the taxanes, for example, paclitaxel and docetaxel; vinca alkyloids such as vinblastine, vincristine and vindesine. In some embodiments, topoisomerase inhibitors which act by breaking DNA, include two types, topoisomerase I and topoisomerase II inhibitors. Topoisomerase I inhibitors include but are not limited to irinotecan (CPT-11). Topoisomerase II inhibitors include, e.g., doxorubicin and epirubicin. Other topoisomerase inhibitors useful in the present invention include but are not limited to etopside, teniposide, idarubicin and daunorubicin. In some embodiments, alkylating agents, which act by damaging DNA, such as chlorambucil, melphalan, cyclophosphamide, ifosfamide, temozolomide, thiotepa, mitomycin C, busulfan, carmustine (BCNU) and lomustine (CCNU) have been shown to be useful chemotherapy agents. The alkylating agents also include the platins such as carboplatin and cisplatin which have been shown to be useful chemotherapy agents, even though they are not alkylators, but rather act by covalently bonding DNA. In some embodiments, thymidylate synthase inhibitors, which interfere with transcription by metabolizing to false bases of DNA and RNA, include, e.g., 5-fluorouracil and capecitabine. In some embodiments, anti-metabolites such as folate antagonists, methotrexate and trimetrexate have been found to be useful as chemotherapeutic agents. In some embodiments, pyrimidine antagonists such as fluorouracil, fluorodeoxyuridine and azacytidine have been found to be useful as chemotherapeutic agents. In some embodiments, purine antagonists have been found to be useful as chemotherapeutic agents and include agents such as mercaptopurine, thioguanine and pentostatin. Sugar modified analogs also useful as chemotherapeutic agents include cytarabine and fludarabine. In some embodiments, ribonucleotide reductase inhibitors have been found to be useful as chemotherapeutic agents and include agents such as hydroxyurea.

The present invention also provides a method of treating or preventing cancer in a subject in need thereof, comprising administering to the subject a therapeutically effective amount of a TMPK inhibitor derivative compound of the present invention. In some embodiments, the TMPK inhibitor derivative compounds of the present invention selectively target toxicity to cancer cells with DNA lesions. In some embodiments, the TMPK inhibitor derivative compounds of the present invention do not result in genotoxic side effects.

In some embodiments, the cancer is selected from the group consisting of breast cancer, hepatoma, colorectal cancer, pancreatic carcinoma, esophageal carcinoma, bladder cancer, ovarian cancer, skin cancer, liver carcinoma, gastric cancer, prostate cancer, colon cancer, lung cancer, rectal cancer, renal cancer, thyroid cancer, brain cancer, melanoma, sarcoma, leukemia, bone cancer and endometrial cancer.

Administration and Pharmaceutical Compositions

The claimed methods involve administration of a TMPK inhibitor composition of the present invention to a subject, either alone or in combination with an additional therapy such as chemotherapy.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compositions of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compositions can be formulated by combining the active compounds with pharmaceutically acceptable carriers well known in the art. Such carriers enable the compositions of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

For administration by inhalation, the compositions for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the composition and a suitable powder base such as lactose or starch.

The compositions may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle.

Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

In addition to the formulations described previously, the compositions may also be formulated as depot preparations. Such long acting formulations may be administered by implantation (for example, subcutaneously or intramuscularly) or by intramuscular injection. A compositions of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Alternatively, other delivery systems for hydrophobic pharmaceutical compositions may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compositions may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an amount sufficient to achieve the intended purpose, e.g., treatment of cancer patients.

More specifically, a "therapeutically effective amount" means an amount of compound effective to prevent, alleviate or ameliorate symptoms of cancer or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of TMPK). Such information can then be used to more accurately determine useful doses in humans.

Toxicity and therapeutic efficacy of the compositions described herein can be determined by standard pharmaceutical procedures in cell cultures or experimental animals, e.g., by determining the $IC_{50}$ and the $LD_{50}$, wherein the $LD_{50}$ is the concentration of test compound which achieves a half-maximal inhibition of lethality, for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to maintain the intended modulating effect. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

The amount of a composition administered will, of course, be dependent on the subject being treated, the severity of the affliction, the manner of administration, the judgment of the prescribing physician, etc.

Accordingly, the present invention provides that the TMPK inhibitor compositions may be administered once daily for 3 consecutive days. In some embodiments, the present invention provides that the TMPK inhibitor compositions may be administered one to two times per day. In other embodiments, the present invention provides that the TMPK inhibitor compositions may be administered at a dose of about 5 mg/kg to about 30 mg/kg.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

The present invention is further illustrated by the following specific examples. The examples are provided for illustration only and should not be construed as limiting the scope of the invention in any way.

Methods of the Invention

Antibodies

Anti-hTMPK polyclonal antibody was prepared as described previously (Chang et al., 1994; Ke et al., 2005). Anti-R2 (sc-10844), anti-p53 R2 and anti-ATM (sc-23921) antibodies were from Santa Cruz. Anti-hTS antibody (clone 4H4B1) was purchased from Zymed Laboratories inc., Anti-DH2AX (Ser139) antibody was purchased from. Anti-β-tubulin, anti-β-actin, anti-rabbit IgG-FITC, anti-mouse IgG-FITC and anti-mouse IgG-TRITC antibodies were from Sigma.

Reagents

G418 and nanofectin were obtained from Invitrogen and PAA laboratories Inc., respectively. ATP, TMP, NADH, phosphoenol pyruvate, 5,5'-dithio-bis(2-nitrobenzoic acid) (DTNB), D-Luciferin, *Photinus pyralis* (firefly) Luciferase, human thrombin, bovine serum albumin (BSA), doxorubicin and H33342 were purchased from Sigma. Lactate dehydrogenase and pyruvate kinase were obtained from Roche.

Glutathione 4B beads were from Amersham Pharmacia, and Annexin V-PE apoptosis kit (CBA-060) and MTS reagent were purchased from Calbiochem and Promega, respectively. hTMPK siRNA was obtained from Dharmacon siGenome SMART pools (MQ-006720), synthesis of R2 siRNA and Lipofectamin 2000 from Invitrogen. Dialyzed serum was purchased from GIBCO™. pLKO-UNG shRNA and pLKO-dUTPase shRNA were purchased from national RNAi core facility in Taiwan.

Cell Culture and Establishment of Stable Cell Lines

HCT-116 p53+/+ and p53−/− cells were kindly provided by Bert Vogelstein at the Johns Hopkins University Medical Institution (Bunz et al., 1998). The growth medium supplemented with 10% FBS were: McCoy's 5A for HCT-116 and U20S, DMEM for MDA-MB231, MEM-α for H184B5F5/M10 cells from Bioresource Collection and Research Center (Hsinchu, Taiwan) (Yang et al., 1996). For establishment of MDA-MB231 cells stably expressing TMPK shRNA and HCT-116 p53−/− cells stably expressing TMPK shRNA, cells were infected with lentiviral TMPK shRNA, after which cells were selected with 2 μg/ml blasticidine.

General Material for Chemical Synthesis of Compounds

All reagents and solvents were reagent grade and used without further purification unless otherwise specified. All solvents were anhydrous grade unless indicated otherwise. Dichloromethane ($CH_2Cl_2$) was distilled from $CaH_2$. All air or moisture sensitive experiments were performed under nitrogen. Reactions were monitored by thin-layer chromatography (TLC) on 0.25 mm E. Merck silica gel 60 $F_{254}$ glass plates. Compounds were visualized by UV, or using p-anisaldehyde, ninhydrine and phosphomolybdic acid (PMA) as visualizing agent. E. Merck silica gel 60 (0.040-0.063 mm particle sizes) were used for flash chromatography.

Instrumentation

Melting points were recorded on a Yanaco micro apparatus. Absorbance spectra were measured on PerkinElmer Lamda 35 UV-Vis spectrometer. Nuclear magnetic resonance (NMR) spectra were obtained on Varian Unity Plus-400 (400 MHz) and chemical shifts (δ) were recorded in parts per million (ppm) relative to $δ_H$ 7.24/$δ_C$ 77.0 (central line of t) for $CHCl_3/CDCl_3$, $δ_H$ 3.31/$δ_C$ 49.0 for $CH_3OH/CD_3OD$, and $δ_H$ 2.50 (m)/$δ_C$ 39.5 (m) for $(CH_3)_2SO/(CD_3)_2SO$. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. High-performance liquid chromatography (HPLC) was performed on Agilent 1100 Series instrument equipped with a degasser, Quat pump, and UV detector.

Luciferase-Coupled TMPK Assay

The TMPK reaction was started by adding purified hTMPK in 50 μl of TMPK assay buffer (100 mM Tris-HCl, pH 7.5, 100 mM KCl, 10 mM MgCl2, 50 μM ATP and 100 μM dTMP) in 96 wells plate at 25° C. for 10 min and terminated by adding 200 μl of DTNB (100 μM), followed by transferring 10 μl of reaction solution to a white 96-wellplate containing 90 μl of luciferase assay buffer (50 mM Glycine, 0.5 mM EDTA and 5 mM EDTA, pH 7.0, 0.1 μg of luciferase, 50 μM luciferin and 0.1% BSA). The luminescence was measured with a luminescence counter (Packard).

NADH-Coupled TMPK Assay

All reactions were performed in 96-well plates in an assay volume of 100 μl. The activity of hTMPK was measured at 25° C. using a modified NADH coupled colorimetric assay as described (Agarwal et al., 1978; Miyata et al., 2003; Ostermann et al., 2003), in which purified hTMPK was added to the buffer containing 100 mM Tris-HCl, pH 7.5, 100 mM KCl, 10 mM MgCl2, 0.5 mM phosphoenol pyruvate, 0.25 mM NADH, 5 units of lactate dehydrogenase, 4 units of pyruvate kinase, 1 mM ATP, and 200 μM dTMP. The change of NADH was measured by reading the absorbance at 340 nm. One unit of TMPK activity is defined as the conversion of 1 mole of TMP to TDP per minute.

Construction of Lentiviral Vector

Using BLOCK-iT™ Lentiviral RNAi Expression System (Invitrogen) constructs lentiviral-based small hairpin RNA (shRNA). Nucleotides 509 to 527 of hTMPK open reading frame and nucleotides 1017 to 1036 in the 3'UTR of hTS gene were chosen as the target sequence. We synthesized one strand of oligonucleotide containing the target sequence followed by a 7-nucleotide short loop and sequence that was the reverse complement of the initial target sequence. The oligonucleotides in pairs were annealed and inserted into pENTR™/U6 RNAi cassette to generate an entry construct. The LacZ double-stranded control oligo supplied in the kit was also cloned as a non-silencing (negative) control siRNA. The lentiviral constructs were then individually cloned by recombination of the U6 RNAi cassette into the pLenti6/BLOCK-iT™-DEST vector.

Lentiviral shRNA Production for Infection

293 FT producer cells (6×$10^6$ cells) were co-transfected with 9 μg of the ViraPower™ packaging Mix (containing a mixture of the pLP1, pLP2, and pLP/VSVG plasmid) and 3 μg of pLenti6 $LacZ^{shRNA}$, $TMPK^{shRNA}$, and $TS^{shRNA}$ by lipofectamine 2000 (Invitrogene). At 72 h after transfection, 10 ml of supernatants containing lentivirus were collected and concentrated with Millipore concentration column to a final volume of 5 ml. The lentiviral $LacZ^{shRNA}$, $TMPK^{shRNA}$, $TS^{shRNA}$ stocks in 1 ml of medium containing 8 μg/ml polybrene were used to infect 2.5×$10^5$ cells overnight, after which the supernatant were replaced with complete medium for the subsequent assays.

Luciferase-Coupled TK Assay

The TK reaction was started by adding purified hTMPK in 50 μl of TK assay buffer (50 mM Tris-HCl, pH 7.5, 1 mM CHAPS, 3 mg/ml BSA, 2.5 mM $MgCl_2$, 50 μM ATP and 100 μM thymidine) in 96 wells plate at 25° C. for 10 min and terminated by adding 200 μl of thymidine (1.25 mM), followed by transferring 10 μl of reaction solution to a white 96-wellplate containing 90 μl of luciferase assay buffer (50 mM Glycine, 0.5 mM EDTA and 5 mM EDTA, pH 7.0, 0.1 μg of luciferase, 50 μM luciferin and 0.1% BSA). The luminescence was measured with a luminescence counter (Packard).

Whole-Cell dTTP Extraction and Quantification $10^6$ cells were extracted with 1 ml of ice-cold 60% methanol at −20° C. overnight, followed by centrifugation for 30 min at 16,000×g. The supernatant was immersed at 100° C. in dry bath for 3 min and dried under vacuum. The dry residue was dissolved in 80 μl of nuclease free water and used for cellular dNTP measurement according to the method described by Ferraro et al. (Ferraro et al., 2010).

Protein Extraction and Western Blotting Analysis

Cell extracts were prepared as described previously (Chang et al., 1998). Equal amounts of protein were resolved on SDS-PAGE (11% (w/v) gel) followed by electrophoretic transfer to PVDF membranes (Millipore). After blocking with 5% (w/v) powdered non-fat milk, the membrane was incubated with different antibodies for overnight at 4° C. and treated for 1 h with horseradish peroxidase-conjugated goat anti-rabbit IgG, goat anti-mouse, and donkey anti-goat antibodies (Santa Cruz). ECL detection for the horseradish peroxidase reaction was performed according to the manufacturer's instructions (PerkinElmer Life Sciences). Protein signal was determined by UVP BioSpectrum 500 Imaging System. Protein expression level was determined by GEL-PRO software.

TABLE 2 shRNA and siRNA targeting sequence

Targeting Sequence

| | | |
|---|---|---|
| LacZ shRNA | CTACACAAATCAGCGATTT | SEQ ID NO: 1 |
| TMPK shRNA | ACACGACTTTGAACTGGAA | SEQ ID NO: 2 |
| TS shRNA | GGATATTGTCAGTCTTTAGG | SEQ ID NO: 3 |
| R2 siRNA | ACCGGAAAAGAAAATGCT | SEQ ID NO: 4 |
| GAPDH gene | 5'-CCAGGGGTGCTAAGCAGTT-3' | SEQ ID NO: 5 |

Immunofluorescence Staining Analysis

For γH2AX staining, cells were fixed with 4% paraformaldehyde for 30 min at room temperature and were incubated with TBS (50 mM Tris-HCl, pH 7.4, 150 mM NaCl) plus 0.3% Triton X-100 for 5 min. The coverslips were blocked with MAXblock™ (Active Motif) for 1 h at 37° C., followed by staining with primary antibodies: anti-γH2AX monoclonal antibody (1:1000), anti-Rad51 polyclonal Cells were seeded at the appropriated density on glass-bottomed dishes. Cells stained with 2 μg/ml Hochest 33342 for 10 min. Laser micro-irradiation was carried out with a FluoView 1000 confocal microscope (Olympus) and a 405 nm laser diode (fast mode, SIM scanner, 250 msec). For γH2AX, endogenous TMPK and R2 co-staining, cells were washed with CSK buffer (100 mM NaCl, 300 mM sucrose, 10 mM PIPES pH 7.0, 3 mM $MgCl_2$) containing 0.1% of Triton X-100 for 5 min prior to fixation with 2% of paraformaldehyde for 15 min.

Luciferase-coupled TMPK assay (Hu and Chang, 2010) was modified and used to screen 21,120 structurally diversified compounds selected from ChemDiv library (San Diego, USA). These compounds were dissolved in DMSO and 10 μM of each was transferred to a well of 1536-well plates containing 0.25 μg of purified hTMPK protein in a final volume of 4 μl. 5,5-dithio-bis(2-nitrobenzoic acid) (DTNB) at final concentration of 10 μM was used as the positive control for TMPK inhibition (Huang et al., 1994). After pre-incubation for 30 min, TMPK reaction was initiated by adding 4 μl of assay buffer containing 100 mM Tris-HCl, pH 7.5, 100 mM KCl, 10 mM MgCl2, 5 μM ATP and 20 μM dTMP for 10 min, followed by addition of 4 μl of luciferase assay buffer (50 mM Glycine, 0.5 mM EDTA and 5 mM EDTA, pH 7.0, 0.1 μg of luciferase, 25 μM luciferin and 0.1% BSA) to each well. Luminescence was acquired by ViewLux detectors (PerkinElmer) and actives of TMPK inhibition were judged by comparing with the positive control.

Cytotoxicity, Apoptosis Assay

Cells plated into a 96-well plate ($10^3$ cells/well) were treated and cell viability was measured by MTS assay (Promega) (Cory et al., 1991). An annexin V-fluorescein isothiocyanate (FITC) apoptosis kit (Calbiochem) was used to detect apoptosis.

Colony Formation Assay

Cells were seeded to 100 mm-dish at 5,000 cells per dish. After 14 days, colonies were fixed and stained by crystal violet and counted.

EXAMPLES

Example 1

TMPK Knockdown has No Genotoxicity but Promoting Doxorubicin-Induced Cell Death in p53 Proficient and Deficient Colon Cancer Cells To understand the differential DNA damage effect of blocking thymidylate kinase (TMPK) and thymidylate synthase (TS) in colon cancer cells. TMPK or TS expression was depleted in colon cancer cells, HCT-116 $p53^{-/-}$, by infection with lentivirus expressing corresponding shRNA. By γH2AX immunofluorescence staining to indicate DNA lesions in nuclei, we found that TS but not TMPK depletion led to genotoxicity. In agreement, cells treated with TS inhibitor, 5-fluoro-2'deoxyuridine (FdUrd) but not an hTMPK inhibitor, YMU1, also gave DNA lesions in nuclei (FIG. 1A). Thus, unlike targeting TS, TMPK inhibition on its own has no genotoxicity. We further tested the effect of TMPK and TS depletion on chemosensitization. Low dose of Doxorubicin treatment was used a chemotherapeutic agent that generates DNA double-strand breaks. TMPK depletion caused apoptosis after low dose of Doxorubicin treatment regardless of the p53 status of HCT-116 cells, while control cells had no apoptotic response (FIG. 1B). In contrast, TS depletion caused HCT-116 p53(+/+) but not HCT-116 p53 (−/−) apoptosis in response to low dose of doxorubicin. This is probably due to the well-established fact that p53 deficiency confers cancer cells drug resistance (FIG. 1C). Therefore, TMPK suppression, even though without genotoxicity by itself, is sufficient to induce the apoptotic response of doxorubicin in cancer cells independent of p53 status.

Example 2

Figure 2:
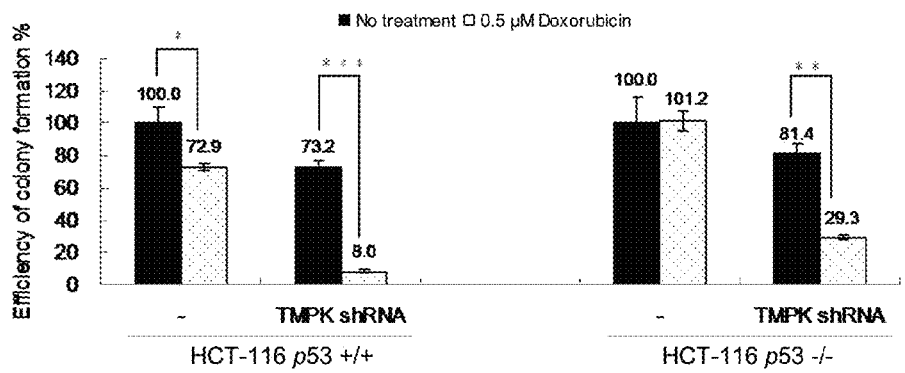
FIG. 2. TMPK knockdown increases doxorubicin sensitivity and suppresses DNA repair, cell growth and dTTP pool in colon cancer cells. (A) p53(+/+) and p53(−/−) HCT-116 cells infected with or without lentiviral TMPK$^{shRNA}$ for 72 hr, seeded to 100 mm-dish at 4,000 cells/dish. Following treatment with or without 0.5 μM doxorubicin for 24 hr, cells were washed with PBS and refreshed with growth medium. After 14 days of culture, surviving colonies were fixed, stained by crystal violet and counted (data represent mean±s.e.m of 3 independent experiments). (B) p53(+/+) and p53(−/−) HCT-116 cells were infected with or without lentivirus delivering TMPK$^{shRNA}$ for 72 hr with a subsequent 0.5 μM doxorubicin treatment as indicated. Cells were fixed with 3% paraformaldehyde and immunostained with anti-γH2AX antibody (1:500) and anti-mouse-TRITC (1:100). The formation of γH2AX foci indicates DNA damage. (C) The cellular level of dTTP in p53(−/−) HCT-116 cells after TMPK knockdown for 3 days. (D) p53(+/+) HCT-116 cells were infected with or without TMPK$^{shRNA}$ lentivirus for cell number counting at the indicated day.
Figure 2:
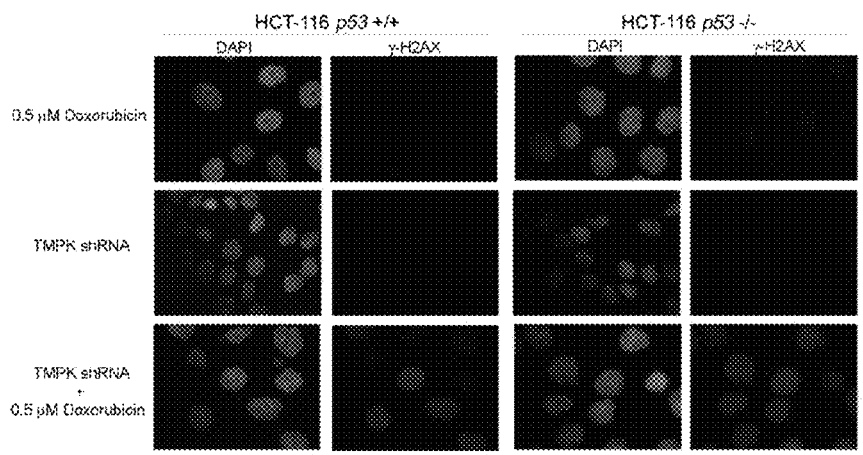
Figure 2:
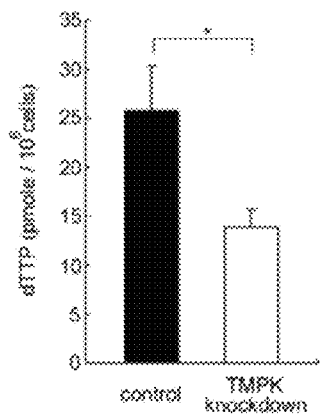
Figure 2:
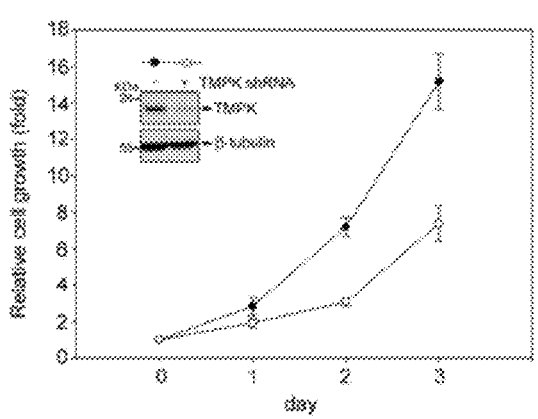

TMPK Knockdown Increases Doxorubicin Sensitivity and Suppresses DNA Repair, Cell Growth and dTTP Pool in Colon Cancer Cells We then tested the effect of TMPK knockdown in combination with low dose of doxorubicin treatment on cell viability. Consistent with the apoptotic effect, the viability of HCT-116 $p53^{-/-}$ and $p53^{+/+}$ cells was significantly reduced by the combination of TMPK depletion with low dose of doxorubicin (FIG. 2A). To understand the chemosensitization effect of TMPK depletion is due to suppressing the repair of Doxorubicin-induced DNA lesion. We performed γH2AX immunofluorescence staining to indicate the repair of doxorubicin-induced DNA lesions. After recovering cells from doxorubicin exposure for 24 hr, the results showed that DNA lesions as indicated by γH2AX in control cells disappeared, in contrast, DNA lesions were sustained in TMPK depleted cells (FIG. 2B). Herein, we conclude that blocking TMPK inhibits DNA repair, thus promoting genotoxic stress-induced cells death in cancer cells regardless of the p53 status of cancer cells. Furthermore, we measured the dTTP level in cells after TMPK depletion. As expected, the results indicated the reduction of dTTP level by TMPK depletion (FIG. 2C). Moreover, the growth of these cells was retarded (FIG. 2D). Given that over 50% of tumors have p53 mutation and the unwanted general toxicity of chemotherapeutic agent, these results reveal the importance of TMPK as a target for treating cancer with low dose of chemotherapeutic agents. The treatment has a minimal general side-effect, because unlike TS inhibitor, TMPK inhibition on its own does not generate genotoxicity. Its effect on chemosensitization is via inhibiting DNA repair in cancer cells.

Example 3

Figure 3:
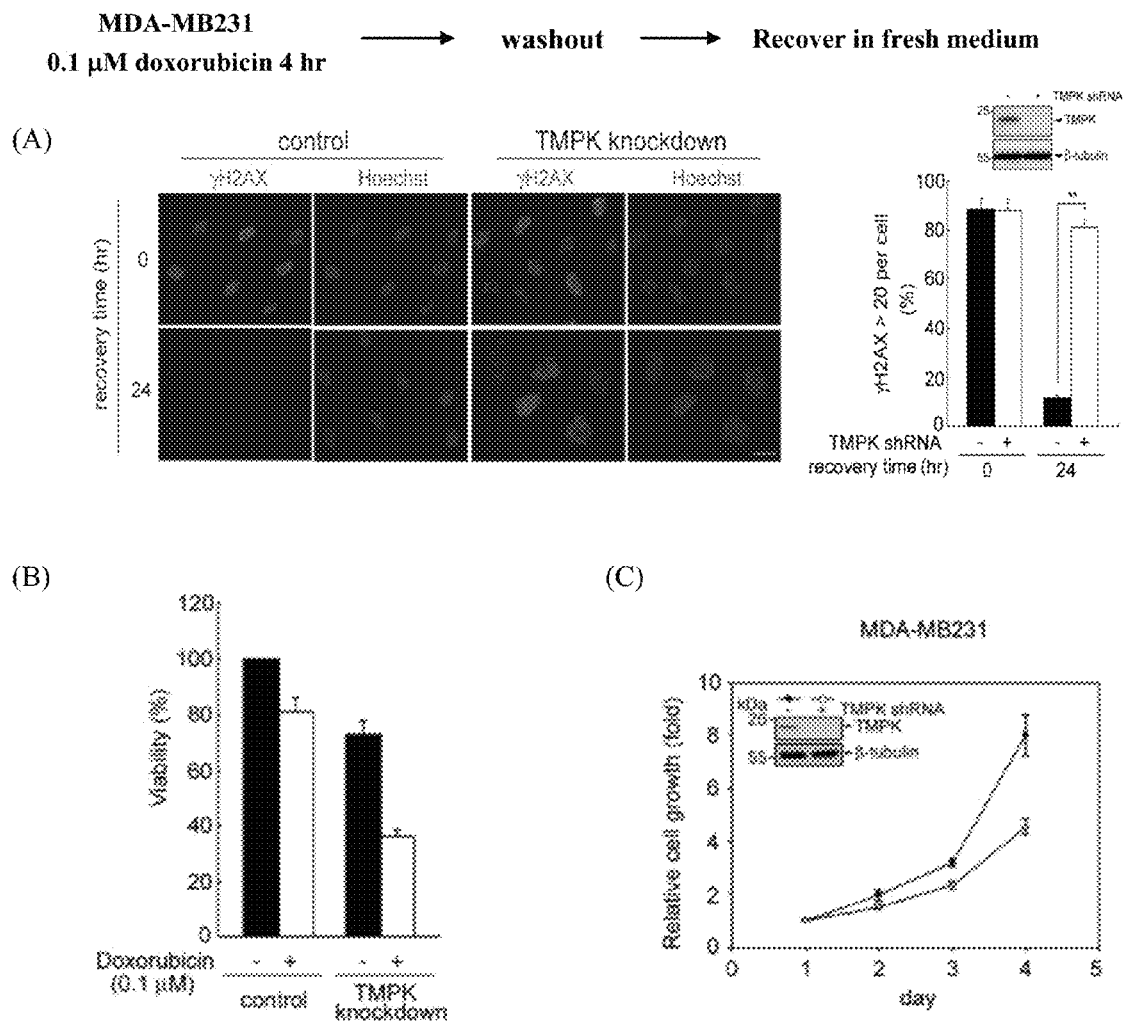
FIG. 3. TMPK depletion inhibits the repair of doxorubicin-induced DNA damage and the cell growth in breast cancer cells. (A) Parental breast cancer MDA-MB231 and stable clone expressing TMPK shRNA were exposed to doxorubicin (0.1 μM) for 4 h, after which drug was removed by washing with fresh medium for recovery 24 hr. (A) Cells were fixed for γH2AX foci staining at the indicated time. Nuclei were visualized with Hoechst 33342 staining. Left panel shows representative images during recovery. Right panel indicates the percentage of cells with >10 γH2AX foci per cell (mean±s.d., n=3; **, P<0.01, two-tailed Student's t-test). For each experiment, more than 100 cells were counted. (B) A parallel set of cells were incubated for another 48 hs, cell viability was determined by MTS assay. Data represent mean±s.d. of 4 experiments. (C) Parental breast cancer MDA-MB231 and stable clone expressing TMPK shRNA plated in a 96-well plate at 1,000 cell per well for cell growth analysis by MTS assay.

TMPK Depletion Inhibits the Repair of Doxorubicin-Induced DNA Damage and the Cell Growth in Breast Cancer Cells Doxorubicin is a major chemotherapeutic agene in breast cancer treatment. We further tested the effect of TMPK depletion on sensitizing breast cancer cells to doxorubicin. MDA-MB231 breast cancer cell line represents a triple-negative breast cancer model. The effect of TMPK depletion on DNA repair of low dose of doxorubicin-induced DNA double-strands breaks was examined. Similar to colon cancer cells, TMPK depletion also impaired DNA repair as revealed by sustained γH2AX staining in MDA-MB231 breast cancer cells recovered from doxorubicin exposure (FIG. 3A). In agreement, the combination of TMPK with low dose of doxorubicin significantly reduced cell viability (FIG. 3B). Since TMPK deletion decreased the dTTP synthesis, the growth rate of TMPK depleted cells was slower (FIG. 3C). In summary, TMPK suppression inhibits the repair of DNA double-strand breaks in breast cancer cells, thereby increasing the therapeutic window of doxorubicin.

Example 4

Figure 4:
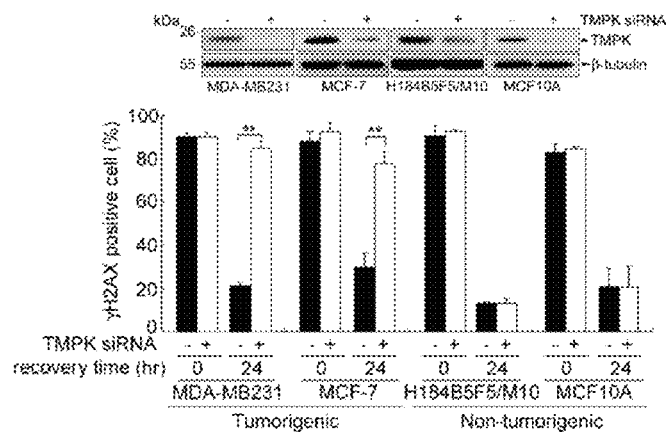
FIG. 4. R2 expression level causes tumorigenic and non-tumorigenic mammary cells different in the sensitivity to TMPK depletion in repairing DNA damage (A) MCF-7, tumorigenic breast cancer cells, H184B5F5/M10 and MCF-10A cells, non-tumorigenic mammary epithelial cells, were transfected with TMPK siRNA. These cells were exposed to doxorubicin and recovered for 24 hr, followed by γH2AX foci staining. Data are expressed the percentage of cells with >10 γH2AX foci per cell (mean±s.d., n=3; **, P<0.01, two-tailed Student's t-test). For each experiment, 100 cells were counted. (B) Cells were exposed to doxorubicin and then underwent recovery. Cells were harvested at the indicated time points for Western blot. (C) MCF-7 cells were transfected with siRNA of TMPK, R2, or TMPK/R2 for 36 hr. A proportion of cells were harvested for Western blot (right panel) and the rest of cells were exposed to doxorubicin (0.1 μM) for 4 hr. Cells at the indicated time points were analyzed by γH2AX foci staining, and 150 cells were counted to indicate the percentage of γH2AX foci-positive cells (left panel). (D) MCF10A clones stably expressing mCherry or mCherry-R2 were selected and transfected with TMPK siRNA for 36 hr. Western blot analysis of the cells (right panel). These cells were exposed to doxorubicin treatment (0.1 μM) and recovery for 24 hr, cells were fixed for γH2AX foci staining. For each experiment, more than 150 cells were counted. All error bars represent SD (n=3). (E) A proposed model to explain why DNA repair in tumor cell is more sensitive to TMPK blockage than non-tumorigenic. Therefore, TMPK inhibition has a chemosensitization effect in cancer cells and is non-toxic to non-tumorigenic cells.
Figure 4:
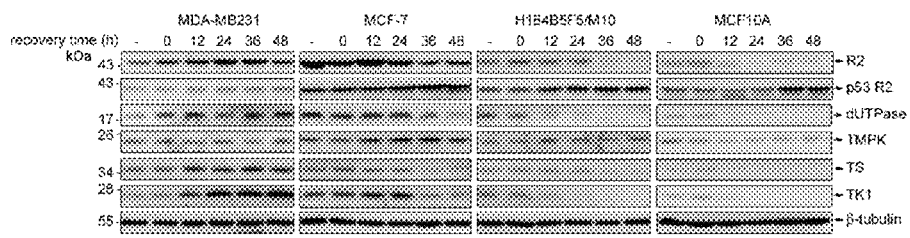
Figure 4:
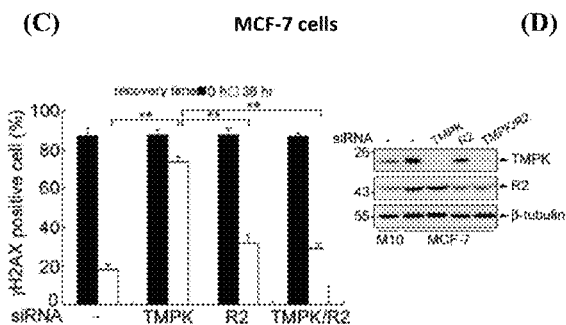
Figure 4:
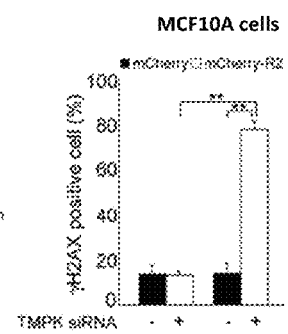
Figure 4:
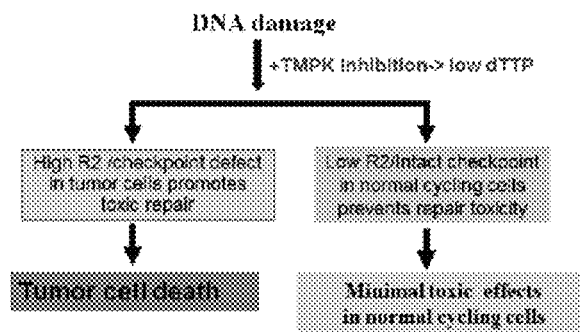

R2 Expression Level Causes Tumorigenic and Non-Tumorigenic Mammary Cells Different in the Sensitivity to TMPK Depletion in Repairing DNA Damage To know whether the combination of TMPK suppression with low dose of doxorubicin is also toxic to proliferating non-tumorigenic cells. We compared the effect of the combination treatment on DNA repair in other breast cancer and non-tumorigenic mammary breast epithelial cells. Similar to MDA-MB231 breast cancer cells, DNA repair in MCF-7, tumorigenic breast cancer cells was inhibited by TMPK depletion. In contrast, DNA repair in H184B5F5/M10 and MCF-10A cells, non-tumorigenic mammary epithelial cells, were insensitive to TMPK depletion (FIG. 4A). By Western blot analysis, we found that tumorigenic and non-tumorigenic cells are very different in the expression of R2 subunit of RNR. The high level of R2 was increased in breast cancer cells during recovery from DNA damage, while decreasing in non-tumorigenic cells (FIG. 4B). It is known that DNA damage causes growth arrest to reduce R2 level. Tumor cells are defective in checkpoint control. Sublethal level of doxorubicin-induced DNA damage does not cause growth arrest and R2 expression continues to be elevated. Non-tumorigenic cells are intact in checkpoint, thereby having DNA damage-responsive growth arrest and reducing R2 expression. We tested the contribution of R2 elevation to sensitivity of TMPK depletion in DNA repair. MCF-7 cells contain p53R2 expression. Therefore, these cells still have RNR function even after R2 depletion. We then transfected MCF7 cells with siRNA of TMPK, R2, or TMPK/R2 for 36 hr for evaluation of the repair of DNA lesions. As shown in FIG. 4C, R2 knockdown caused MCF-7 cells insensitive to TMPK deficiency in DNA repair. This indicates that the high level of RNR causes cancer cells highly dependent on the function of TMPK for DNA repair. To verify this hypothesis, we further overexpressed R2 in MCF10a, a non-tumorigenic breast epithelial cell line and tested the effect of R2 overexpression on sensitivity to TMPK suppression on DNA repair. The results showed that overexpression of R2 suppressed DNA repair in TMPK knockdown MCF10a cells (FIG. 4D). We proposed that tumor cells defective in checkpoint express high level of R2 in response to DNA damage, which require TMPK function for DNA repair. In contrast, non-tumorigenic cells intact in checkpoint express low level of R2, thereby the requirement for TMPK in DNA repair is much less. Therefore, TMPK inhibition has a chemosensitization effect in cancer cells and is non-toxic to non-tumorigenic cells.

Example 5

Figure 5:
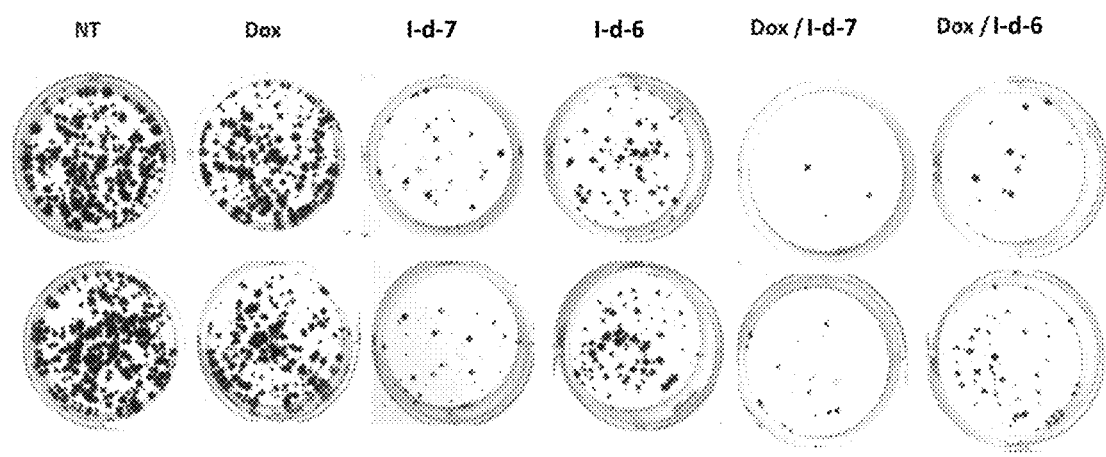
FIG. 5. The effect of TMPK inhibitors alone or in combination with a chemotherapeutic agent on viability of osteosarcoma cells. (A) Human RM osteosarcoma cells (a representative bone cancer cells) were seeded at $2\times10^4$/35 mm dish and treated with Doxorubicin (20 nM), compound I-d-7 (5 μM), compound I-d-6 (5 μM) as indicated. After 2 days, medium was replaced with fresh medium without drug and cells were replated to a 24-well plate at 600 cells/well for 1 week for colony formation analysis.

The Effect of TMPK Inhibitors Alone or in Combination with a Chemotherapeutic Agent on Viability of Osteosarcoma Cells Osteosarcoma cancer uses doxorubicin as a major chemotherapeutic agent. We treated human RM osteosarcoma cells (a representative bone cancer cells) with hTMPK inhibitor, compound I-d-7 (5 µM), compound I-d-6 (5 µM) as indicated in combination with Doxorubicin (20 nM). Such a low dose of doxorubicin had no effect on suppressing the colony formation of osteosarcoma cells. Two hTMPK inhibitors had a significant effect on suppressing colony formation. The combination of doxorubicin (20 nM) with these two compounds further decreased colony formation (FIG. 5). Thus, these two compounds have a therapeutic effect on suppressing the growth and promoting doxorubicin effect on survival of osteosarcoma cells.

Example 6

Figure 6:
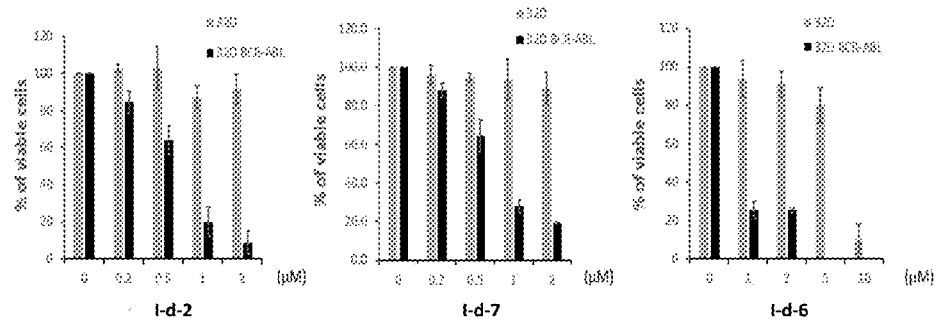
FIG. 6. The selective growth inhibition by TMPK inhibitors in myeloid cells transformed by BCR-ABL oncogene. (A) Myeloid 32D normal progenitor cells and BCR-ABL-transformed 32D cells in log phase at $1\times10^5$ cells/ml were incubated with the compounds I-d-2, I-d-6 and I-d-7 at the concentration as indicated. After 3 days, cell viability was measured by WST1 assay. (B) 32D and 32D-BCR-ABL myeloid cells were treated with vehicle, I-d-2 and I-d-6 at 5 μM for 6 hr, after which cells were harvested for dTTP measurement.
Figure 6:
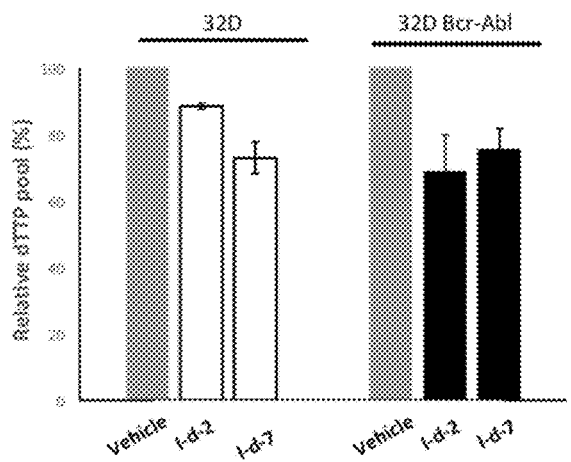

The Selective Growth Inhibition by TMPK Inhibitors in Myeloid Cells Transformed by BCR-ABL Oncogene It is well accepted that oncogenic transformation involves DNA damage. Chronic myeloid leukemia is known to arise due to chromosome translocation to give a BCR-ABL fusion gene, which encodes an oncogenic protein BCR-ABL. FIG. 6A showed that TMPK inhibitor treatment had a selective effect on suppressing the growth of BCR-ABL-transformed 32D myeloid cells but not normal myeloid progenitor cells. Thus, TMPK inhibitors have a therapeutic potential in treating chronic myeloid leukemia. FIG. 6B showed that these inhibitor treatments in 6 hr were sufficient to reduced cellular level of dTTP, indicating their in vivo effect on inhibiting the function of TMPK in dTTP formation.

Example 7

TMPK Inhibitor Derivatives

Tert-butyl 4-(2-(3-oxoisothiazolo[5,4-b]pyridin-2(3H)-yl)acetyl)piperazine-1-carboxylate (I-a-1)

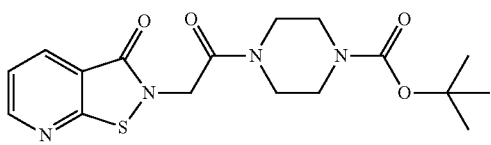

I-a-1

A mixture of 2-chloronicotinonitrile (200 mg, 1.44 mmol) and thiourea (310 mg, 4.33 mmol) in n-butanol (5 mL) was heated at reflux (118° C.) for 4 h. After cooling to room temperature, the solution turned to a suspension containing light yellow solids. The solids were collected by filtration, rinsed with n-butanol, and dried under reduced pressure to give 2-mercaptonicotinonitrile (144 mg, 73% yield). $C_6H_4N_2S$; yellow powder; mp 202-203° C. $^1$H NMR (400 MHz, $CD_3OD$); δ 7.96 (1H, dd, J=7.6, 2.0 Hz), 7.81 (1H, dd, J=6.4, 2.0 Hz), 6.83 (1H, td, J=7.2, 1.2 Hz); $^{13}$C NMR (100 MHz, DMSO-$d_6$) δ 177.3, 145.5, 142.7, 116.8, 116.6, 112.3; ESI-HRMS (negative mode) calcd for $C_6H_3N_2S$: 135.0017. found: m/z 135.0016 [M−H]$^-$.

A solution of 2-mercaptonicotinonitrile (1000 mg, 7.34 mmol) in conc. $H_2SO_4$ (8 mL) was stirred at 100° C. for 4 h. The mixture was cooled and adjusted to pH 5-6 by addition of saturated $NaHCO_{3(aq)}$ to produce yellow solids in suspension. The solids were collected by filtration, rinsed with $H_2O$, and dried under reduced pressure to give isothiazolo[5,4-b]pyridin-3(2H)-one (333 mg, 30% yield). $C_6H_4N_2OS$; yellow powder; mp 170-171° C.; IR $v_{max}$ (neat) 3415, 2916, 2872, 2345, 2304, 1659, 1585, 1560, 1377, 1102, 952, 770, 500 cm$^{-1}$; $^1$H NMR (400 MHz, CDCl$_3$); δ 8.81 (1H, dd, J=4.8, 1.6 Hz), 8.33 (1H, dd, J=7.6, 1.6 Hz), 7.40 (1H, m); $^{13}$C NMR (100 MHz, DMSO-$d_6$) δ163.7, 153.2, 133.8, 120.9 (2×), 118.9; ESI-HRMS (negative mode) calcd for $C_6H_3N_2OS$: 150.9966. found: m/z 150.9965 [M−H]$^-$.

A mixture of piperazine (6.8 g, 78.9 mmol) and diisopropylethylamine (DIEA, 13.6 mL, 78.9 mmol) in anhydrous $CH_2Cl_2$ (150 mL) was stirred at room temperature, and a solution of di-tert-butyl dicarbonate (8.6 mL, 39.4 mmol) in anhydrous $CH_2Cl_2$ (200 mL) was added slowly via a separatory funnel over a period of 18 h. The mixture was extracted with $CH_2Cl_2$ and $H_2O$. The organic phase was dried over $MgSO_4$, filtered, and concentrated to give mono-Boc protected piperazine (7.38 g, 99% yield). $C_9H_{18}N_2O_2$; white solid; mp 47-48° C.; $^1$H NMR (400 MHz, CDCl$_3$) δ 3.36-3.34 (5H, m), 2.78-2.76 (3H, m), 1.43 (9H, s); $^{13}$C NMR (100 MHz, CDCl$_3$) δ 155.1, 79.8, 46.1 (4×), 28.6 (3×); ES-HRMS calcd for $C_9H_{19}N_2O_2$: 187.1447. found: m/z 187.1446 [M+H]$^+$.

A mixture of the above-prepared mono-Boc protected piperazine (2.26 g, 12.1 mmol) and DIEA (6.3 mL, 36.4 mmol) in anhydrous $CH_2Cl_2$ was stirred in ice-bath, and chloroacetyl chloride (1.1 mL, 13.3 mmol) was slowly added. The mixture was stirred at room temperature for 4 h and extracted with $CH_2Cl_2$ and $H_2O$. The organic phase was dried over $MgSO_4$, filtered, and purified by flash chromatography on a silica gel column with elution of EtOAc/hexane (1:2) to give tert-butyl 4-(2-chloroacetyl)piperazine-1-carboxylate (2.87 g, 89% yield). $C_{11}H_{19}ClN_2O_3$; Yellowish solid; mp 91-93° C.; $^1$H NMR (400 MHz, CDCl$_3$) δ 4.06 (2H, s), 3.58-3.57 (2H, m), 3.48 (4H, s), 3.44-3.42 (2H, m), 1.45 (9H, s); $^{13}$C NMR (100 MHz, CDCl$_3$) δ 165.3, 154.5, 80.5, 46.2 (2×), 42.0 (2×), 40.7, 28.3 (3×); ES-HRMS calcd for $C_{11}H_{20}ClN_2O_3$: 263.1162. found: m/z 263.1153 [M+H]$^+$.

A mixture of the above-prepared 4-(2-chloroacetyl)piperazine-1-carboxylate (1.41 g, 5.38 mmol) and sodium iodide (2.42 g, 16.14 mmol) in acetone (30 mL) was stirred at room temperature for 18 h. The mixture was concentrated under reduced pressure, and extracted with $CH_2Cl_2$ and $H_2O$. The organic phase was dried over $MgSO_4$, filtered, and concentrated to give tert-butyl 4-(2-iodoacetyl)piperazine-1-carboxylate (1.71 g, 90% yield). $C_{11}H_{19}IN_2O_3$; brown solid; mp 90-92° C.; $^1$H NMR (400 MHz, CDCl$_3$) δ 3.73 (2H, s), 3.58-3.56 (2H, m), 3.52-3.50 (2H, m), 3.42-3.39 (4H, m), 1.45 (9H, s); $^{13}$C NMR (100 MHz, CDCl$_3$) δ 166.7, 154.4, 80.4, 47.0 (2×), 41.9 (2×), 28.3 (3×), −4.4; ES-HRMS calcd for $C_{11}H_{20}IN_2O_3$: 355.0519. found: m/z 355.0519 [M+H]$^+$.

A mixture of the-above prepared isothiazolo[5,4-b]pyridin-3(2H)-one (500 mg, 3.29 mmol), tert-butyl 4-(2-iodoacetyl)piperazine-1-carboxylate (1.17 mg, 3.29 mmol), $Cs_2CO_3$ (1.07 mg, 3.29 mmol) and $Et_3N$ (2.28 mL, 16.45 mmol) in $CH_2Cl_2$ (20 mL) was stirred for 5 h at room temperature. The mixture was concentrated under reduced pressure, and then purified by flash chromatography on a silica gel column with elution of EtOAc/hexane (1:1) and EtOAc to give compound I-a-1 (910 mg, 40% yield). The purity of product I-a-1 was 98.3% as shown by HPLC on DIKMA column (Agilent, 4.6×250 mm, 5 μm), $t_R$=9.5 min by elution of EtOAc at a flow rate of 1.0 ml/min for 20 min. $C_{17}H_{22}N_4O_4S$; yellow solid; mp 168-169° C.; IR $v_{max}$ (neat) 3515, 2976, 2929, 2865, 2390, 2353, 1665, 1586, 1564, 1462, 1415, 1395, 1365, 1286, 1235, 1168, 1127, 1028, 996, 863, 761, 557 cm$^{-1}$; $^1$H NMR (400 MHz, CDCl$_3$) δ 8.77 (1H, dd, J=4.4, 1.6 Hz), 8.28 (1H, dd, J=8.0, 2.0 Hz), 7.35 (1H, dd, J=7.6, 4.4 Hz), 4.71 (2H, s), 3.62-3.59 (2H, m), 3.52-3.42 (6H, m) 1.45 (9H, s); $^{13}$C NMR (100 MHz, CDCl$_3$) δ 164.8, 164.2, 163.3, 154.4, 154.0, 134.9, 120.6, 118.3, 80.6, 45.0 (2×), 44.5, 42.0 (2×), 28.3 (3×); ESI-HRMS calcd for $C_{17}H_{23}N_4O_4S$: 379.1440. found: m/z 379.1438 [M+H]$^+$.

4-Nitrophenyl 4-(2-(3-oxoisothiazolo[5,4-b]pyridin-2(3H)-yl)acetyl)piperazine-1-carboxylate (I-a-2)

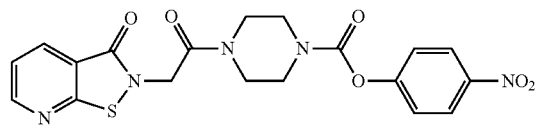

I-a-2

A mixture of 2-(2-oxo-2-(piperazin-1-yl)ethyl)isothiazolo[5,4-b]pyridin-3(2H)-one (I-c-1) (750 mg, 1.00 mmol), 4-nitrophenyl chloroformate (770 mg, 3.82 mmol) and DMAP (400 mg, 3.25 mmol) in $CH_2Cl_2$ (10 mL) was stirred for 16 h at room temperature. The mixture was concentrated under reduced pressure, and it was purified by a silica gel column chromatography with elution of EA/Hex (1:1 to EtOAc) to 10% MeOH/CH$_2$Cl$_2$ to give compound I-a-2 (19 mg, 4% yield). C$_{19}$H$_{17}$N$_5$O$_6$S; yellow solid; mp 218-219° C.; IR $v_{max}$ (neat) 3314, 2927, 2860, 2857, 2360, 2341, 1722, 1657, 1519, 1394, 1345, 1254, 1211, 1058, 1030, 747 cm$^{-1}$; $^1$H NMR (400 MHz, CDCl$_3$) δ 8.79 (1H, d, J=4.4 Hz), 8.29 (3H, m), 7.38 (1H, dd, J=8, 4.8 Hz), 7.30 (2H, d, J=7.2 Hz), 4.75 (2H, s), 3.74-3.67 (8H, m); $^{13}$C NMR (100 MHz, CDCl$_3$) δ 165.2, 164.5, 163.4, 156.0, 154.3, 145.3, 135.2, 127.0, 125.4 (2×), 122.5 (2×), 121.0, 118.5, 45.1, 44.7, 44.1, 42.0 (2×); ESI-HRMS calcd for C$_{19}$H$_{18}$N$_5$O$_6$S: 444.0978. found: m/z 444.0981 [M+H]$^+$.

Tert-butyl 4-[(6-amino-4-methyl-3-oxoisothiazolo[5,4-b]pyridin-2(3H)-2-yl)acetyl]piperazine-1-carboxylate (I-a-3)

I-a-3

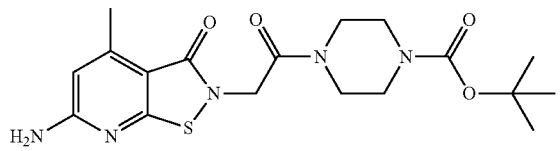

A mixture of 2-cyanothioacetamide (3.0 g, 30 mmol), 3-aminocrotononitrile (2.46 g, 30 mmol) in 1,4-dioxane (30 mL) was stirred at 100° C. for 2 h. After cooling to room temperature, the solids were collected and recrystallized from EtOH to give 6-amino-2-mercapto-4-methylnicotinonitrile (1.18 g, 24% yield). C$_7$H$_7$N$_3$S; light yellow solid; $^1$H NMR (400 MHz, DMSO-d$_6$); δ 5.89 (1H, s), 2.18 (3H, s); $^{13}$C NMR (100 MHz, DMSO-d$_6$) δ 175.4, 155.2, 153.5, 118.1, 100.2, 99.0, 20.8; ESI-HRMS calcd for C$_7$H$_8$N$_3$S: 166.0439. found: m/z 166.0437 [M+H]$^+$.

A mixture of the-above prepared 6-amino-2-mercapto-4-methylnicotinonitrile (145 mg, 0.88 mmol) and conc. H$_2$SO$_4$ (1.5 mL) was stirred at 100° C. for 5 h. The mixture was cooled and adjusted to pH 5-6 by addition of NaHCO$_{3(s)}$, producing white solids in suspension. The solids were collected by filtration, rinsed with H$_2$O, and dried in vacuo to give 6-amino-4-methylisothiazolo[5,4-b]pyridine-3-(2H)-one (156 mg, 98% yield). C$_7$H$_7$N$_3$OS; pale yellow solid; mp 204-206° C.; TLC (CH$_2$Cl$_2$/MeOH=9:1) R$_f$=0.2; IR $v_{max}$ (neat) 3421, 3344, 3069, 1632, 1600, 1550, 1453, 1375, 1209, 1170, 1028, 983, 838, 619, 550, 500 cm$^{-1}$; $^1$H NMR (400 MHz, DMSO-d$_6$); δ 6.82 (2H, s), 6.19 (1H, s), 2.45 (3H, s); $^{13}$C NMR (100 MHz, DMSO-d$_6$) δ 168.0, 166.0, 161.8, 147.5, 107.2, 106.9, 17.4; ESI-HRMS calcd for C$_7$H$_8$N$_3$OS: 182.0388. found: m/z 182.0395 [M+H]$^+$.

A mixture of the-above prepared 6-amino-4-methylisothiazolo[5,4-b]pyridine-3-(2H)-one (100 mg, 0.55 mmol), tert-butyl 4-(2-iodoacetyl)piperazine-1-carboxylate (98 mg, 0.28 mmol) and DIEA (0.38 mL, 2.27 mmol) in anhydrous DMF (3.8 mL) was stirred for 3 h at room temperature. The solution was concentrated under reduced pressure, and then purified by flash chromatography on a silica gel column with elution of EtOAc/hexane (1:1 to 3:1) to give compound I-a-3 (78 mg, 68% yield). C$_{18}$H$_{25}$N$_5$O$_4$S; white solid; mp 226-228° C.; TLC (EtOAc/hexane=1:1) R$_f$=0.1; IR $v_{max}$ (neat) 3260, 3109, 2944, 2887, 1708, 1603, 1568, 1495, 1379, 1298, 1219, 1142, 1080, 928, 795, 667, 432 cm$^{-1}$; $^1$H NMR (400 MHz, CD$_3$OD) δ 6.29 (1H, s), 4.70 (2H, s), 3.56-3.57 (4H, m), 3.53 (2H, br, s), 3.45 (2H, s), 2.54 (3H, s), 1.48 (9H, s); $^{13}$C NMR (100 MHz, CDCl$_3$) δ 167.8, 167.7, 166.5, 163.8, 156.4, 150.9, 109.1, 108.1, 81.9, 45.9, 45.3, 43.2, 28.8 (3×), 18.1; ESI-HRMS calcd for C$_{18}$H$_{26}$N$_5$O$_4$S: 408.1706. found: m/z 408.1706 [M+H]$^+$.

4-Nitrophenyl 4-[2-(6-amino-4-methyl-3-oxoisothiazolo[5,4-b]pyridin-2(3H)-yl)acetyl]piperazine-1-carboxylate (I-a-4)

I-a-4

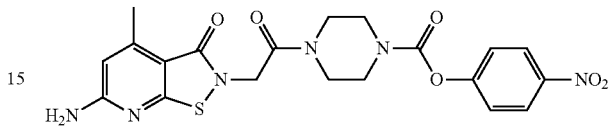

A mixture of 6-amino-4-methyl-2-[2-oxo-2-(piperazin-1-yl)ethyl]isothiazolo[5,4-b]pyridin-3(2H)-one (I-c-3) as the TFA salt (55 mg, 0.10 mmol), 4-nitrophenyl chloroformate (22 mg, 0.11 mmol) and DMAP (37 mg, 0.30 mmol) in anhydrous DMF (0.5 mL) was stirred for 72 h at room temperature. The solution was concentrated under reduced pressure, and washed with MeOH to give brown solids. The solids were removed and the supernatant was purified by flash chromatography on a silica gel column with elution of CH$_2$Cl$_2$/MeOH (30:1 to 20:1) to give compound I-a-4 (10 mg, 21% yield). C$_{20}$H$_{20}$N$_6$O$_6$S; white solid; mp 232-234° C.; TLC (EA) R$_f$=0.3; IR $v_{max}$ (neat) 3321, 3211, 2923, 2852, 2486, 1731, 1638, 1593, 1523, 1442, 1422, 1344, 1028, 1158, 1109, 1018, 858, 746, 542 cm$^{-1}$; $^1$H NMR (400 MHz, DMSO-d$_6$) δ 8.29 (2H, d, J=8.8 Hz), 7.47 (2H, d, J=8.8 Hz), 6.93 (2H, br, s), 6.22 (2H, s), 4.67 (2H, s), 2.46 (3H, s); $^{13}$C NMR (100 MHz, DMSO-d$_6$) δ 165.3, 164.9, 164.3, 161.7, 155.9, 151.6, 147.9, 144.3, 125.0 (2×), 122.8 (2×), 107.1, 105.6, 43.8, 17.2; ESI-HRMS calcd for C$_{20}$H$_{21}$N$_6$O$_6$S: 473.1243. found: m/z 473.1237 [M+H]$^+$.

Tert-butyl 4-[(6-hydroxy-4-methyl-3-oxoisothiazolo[5,4-b]pyridin-2(3H)-2-yl)acetyl]piperazine-1-carboxylate (I-a-5)

I-a-5

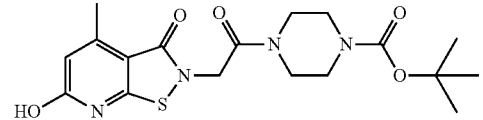

Tert-butyl 4-[(6-amino-4-methyl-3-oxoisothiazolo[5,4-b]pyridin-2(3H)-2-yl)acetyl]piperazine-1-carboxylate (I-a-3) (133 mg, 0.33 mmol) was added to a solution of conc. H$_2$SO$_4$ (0.04 mL, 0.7 mmol) and H$_2$O (0.5 mL) below 0° C. The resultant solution was treated with a solution of NaNO$_2$ (24.1 mg, 0.35 mmol) in H$_2$O (0.5 mL) below 5° C. and stirred for 45 min. After then, the mixture was heated to 95° C. for 1 h and turned into transparent solution. Once cooling, the solution was neutralized by NaHCO$_{3(aq)}$ to pH 6-7, and dried under reduced pressure to give pale solids.

The crude solids were then treated with di-tert-butyl dicarbonate (0.1 mL, 0.5 mmol) and DIEA (0.3 mL, 1.63 mmol) in anhydrous DMF (1 mL), and stirred at room temperature for 2 h. The solution was concentrated under reduced pressure and purified by flash chromatography on a silica gel column with elution of CH$_2$Cl$_2$/MeOH (40:1 to 9:1) to give compound I-a-5 (10 mg, 8% yield). C$_{18}$H$_{24}$N$_4$O$_5$S; white solid; mp 195-197° C.; TLC (EtOAc/hexane=4:1) R$_f$=0.1; IR v$_{max}$ (neat) 3455, 3241, 2975, 2928, 2855, 1703, 1644, 1546, 1464, 1418, 1384, 1287, 1230, 1170, 1127, 1030, 860, 765, 556 cm$^{-1}$; $^1$H NMR (400 MHz, CD$_3$OD) δ 6.25 (1H, s), 4.73 (2H, s), 3.54-3.60 (6H, m), 3.46 (2H, s), 2.56 (3H, s), 1.48 (9H, s); $^{13}$C NMR (100 MHz, CD$_3$OD) δ 167.3 (2×), 166.4, 156.1, 153.1, 115.3, 81.8, 45.9, 45.3, 44.1 (2×), 43.2, 28.8 (3×), 18.6; ESI-HRMS calcd for C$_{18}$H$_{25}$N$_4$O$_5$S: 409.1546. found: m/z 409.1547 [M+H]$^+$.

1-(2-Oxo-2-(4-(2-(3-oxoisothiazolo[5,4-b]pyridin-2(3H)-yl)acetyl)piperazin-1-yl)ethyl)-3-phenylurea (I-b-1)

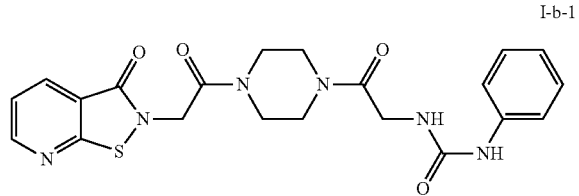

Et$_3$N (1.1 mL, 7.88 mmol) was added to a solution of glycine methyl ester hydrochloride (1.00 g, 7.96 mmol) in anhydrous CH$_2$Cl$_2$ (37 mL) at 0° C. The mixture was stirred at room temperature for 15 min to neutralization. Phenyl isocyanate (1.15 g, 6.64 mmol) was added dropwise into the solution. The mixture was stirred at room temperature under Ar atmosphere for 22 h, and then washed with 1 M HCl$_{(aq)}$ and brine. Methyl 2-(3-phenylureido)acetate (560 mg, 34%) was obtained after flash column chromatography (silica gel, hexane/EtOAc (1:1)). C$_{10}$H$_{12}$N$_2$O$_3$; white solid, mp 134-135° C.; $^1$H NMR (400 MHz, CDCl$_3$) δ 8.79 (1H, s), 7.39 (2H, d, J=7.9 Hz), 7.22 (2H, t, J=7.9 Hz), 6.90 (1H, td, J=7.9, 1.2 Hz), 6.45 (1H, t, J=5.7 Hz), 3.88 (2H, d, J=5.7 Hz), 3.65 (3H, s); $^{13}$C NMR (100 MHz, CDCl$_3$) δ 171.4, 155.2, 140.2, 128.7 (2×), 121.3, 117.7 (2×), 51.6, 41.3; ESI-HRMS calcd for C$_{10}$H$_{13}$N$_2$O$_3$: 209.0926. found m/z 209.0927 [M+H]$^+$.

The above-prepared urea compound (60 mg, 0.29 mmol) was dissolved in MeOH (2 mL), and 1 M NaOH$_{(aq)}$ was added into the solution at room temperature. The mixture was stirred for 90 min, adjusted to pH=6-7 by adding Dowex resin. After filtration and concentration, 2-(3-phenylureido)acetic acid (50 mg, 87%) was obtained. C$_9$H$_{10}$N$_2$O$_3$; white solid, mp 195-196° C.; IR v$_{max}$ (neat) 3351, 2925, 1651, 1630, 1596, 1584, 1551, 1441, 1246, 1230 cm$^{-1}$; $^1$H NMR (400 MHz, DMSO-d$_6$) δ 12.58 (1H, br), 8.76 (1H, s), 7.38 (2H, d, J=7.8 Hz), 7.22 (2H, t, J=7.8 Hz), 6.89 (1H, t, J=7.8 Hz), 6.35 (1H, t, J=5.8 Hz), 3.79 (2H, d, J=5.8 Hz); $^{13}$C NMR (100 MHz, DMSO-d$_6$) δ 172.2, 155.2, 140.3, 128.7 (2×), 121.2, 117.6 (2×), 41.3; ESI-HRMS (negative mode) calcd for C$_9$H$_9$N$_2$O$_3$: 193.0613. found m/z 193.0612 [M−H]$^-$.

To a solution of the above-prepared 2-(3-phenylureido)acetic acid (14 mg, 0.07 mmol) in DMF (1.7 mL) were added compound 12 (17 mg, 0.06 mmol), EDC (10 mg, 0.06 mmol), DMAP (2 mg, 0.02 mmol) and DIEA (0.03 mL, 0.17 mmol) at room temperature. The mixture was stirred for 21 h, and then concentrated under reduced pressure. The residue was extracted with CH$_2$Cl$_2$ and 1 M HCl$_{(aq)}$ and saturated NaHCO$_{3(aq)}$. The combined organic phase was washed with brine, dried over MgSO$_4$ and concentrated under reduced pressure. After flash column chromatography (silica gel, CH$_2$Cl$_2$/MeOH=98:2), the product I-b-1 (7 mg, 25% yield) was obtained. The purity of product I-b-1 was 96% as shown by HPLC on an HC-C18 column (Merck, 4.6×100 mm, 5 m porosity), t$_R$=2.04 min (MeOH/H$_2$O=1:1, flow rate=1 mL/min). C$_{21}$H$_{22}$N$_6$O$_4$S; white solid, mp 220-223° C.; IR v$_{max}$ (neat) 3378, 3318, 1668, 1640, 1544 cm$^{-1}$; $^1$H NMR (400 MHz, DMSO-d$_6$) δ 8.92 (1H, br s), 8.87 (1H, m), 8.32 (1H, dt, J=7.7 Hz), 7.54 (1H, m), 7.40 (2H, d, J=7.3 Hz), 6.89 (1H, t, J=7.3 Hz), 6.37 (1H, br s), 4.88 (2H, s), 4.04 (2H, d, J=4.4 Hz), 3.57-3.48 (8H, m); $^{13}$C NMR (100 MHz, DMSO-d$_6$) δ167.8, 164.8, 163.7, 162.4, 155.0, 154.2, 140.4, 134.7, 128.7, 121.2, 121.1, 118.0, 117.5, 44.5, 43.8 (2×), 43.7 (2×), 40.1; ESI-HRMS calcd for C$_{21}$H$_{23}$N$_6$O$_4$S: 455.1502. found m/z 455.1524 [M+H]$^+$.

1-(2-(4-(2-(4,6-Dimethyl-3-oxoisothiazolo[5,4-b]pyridin-2(3H)-yl)acetyl)piperazin-1-yl)-2-oxoethyl)-3-phenylurea (I-b-2)

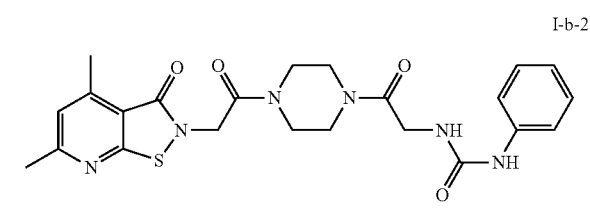 [SMILES: Cc1cc(C)c2c(=O)n(CC(=O)N3CCN(C(=O)CNC(=O)Nc4ccccc4)CC3)sc2n1]

A solution of 2-(3-phenylureido)acetic acid (38 mg, 0.20 mmol) in DMF (4.6 mL) were added 4,6-dimethyl-2-(2-oxo-2-(piperazin-1-yl)ethyl)isothiazolo[5,4-b]pyridin-3(2H)-one (I-c-2) (50 mg, 0.16 mmol), EDC (42 mg, 0.18 mmol), DMAP (6 mg, 0.05 mmol) and DIEA (0.09 mL, 0.49 mmol) at room temperature. The mixture was stirred for 21 h, and then concentrated under reduced pressure. The residue was extracted with CH$_2$Cl$_2$ and 1 M HCl$_{(aq)}$ and saturated NaHCO$_{3(aq)}$. The combined organic phase was washed with brine, dried over MgSO$_4$ and concentrated under reduced pressure. After flash column chromatography (silica gel, CH$_2$Cl$_2$/MeOH=98:2), the product I-b-2 (18 mg, 23% yield) was obtained. The purity of product I-b-2 was 91% as shown by HPLC on an HC-C18 column (Merck, 4.6×100 mm, 5 m porosity), t$_R$=4.99 min (MeOH/H$_2$O=1:1, flow rate=1 mL/min). C$_{23}$H$_{26}$N$_6$O$_4$S; white solid, mp 224-227° C.; IR v$_{max}$ (neat) 3491, 3350, 3301, 2921, 1657, 1641, 1552, 1478, 1425 cm$^{-1}$; $^1$H NMR (400 MHz, DMSO-d$_6$) δ 8.90 (1H, br s), 7.39 (2H, d, J=7.7 Hz), 7.22 (2H, t, J=7.7 Hz), 7.15 (1H, s), 6.89 (1H, t, J=7.7 Hz), 6.36 (1H, m), 4.79 (2H, s), 4.04 (2H, d, J=4.4 Hz), 3.57 (2H, br s), 3.53-3.48 (6H, m), 2.64 (3H, s), 2.54 (3H, s); $^{13}$C NMR (100 MHz, CD$_3$OD) δ 167.8, 165.0, 164.4, 162.8, 162.6, 155.0, 149.1, 140.4, 128.7 (2×), 122.4, 121.1, 117.5 (2×), 113.6, 44.2, 43.8 (2×), 41.2 (2×), 40.1, 24.1, 16.7; ESI-HRMS calcd for C$_{23}$H$_{27}$N$_6$O$_4$S: 483.1815. found m/z 483.1808 [M+H]$^+$.

4,6-Dimethyl-2-[2-(4-(2-iodoacetyl)piperazin-1-yl)-2-oxoethyl]-isothiazolo[5,4-b]pyridin-3(2H)-one (I-b-3)

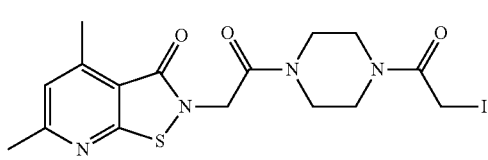

A solution of 4,6-dimethylisothiazolo[5,4-b]pyridine-3(2H)-one (105 mg, 0.58 mmol) in anhydrous $CH_2Cl_2$ (2.4 mL) was added via syringe pump over a period of 2 h to a suspension of 1,4-bis(iodoacetyl)piperazine (245 mg, 0.58 mmol) and DIEA (0.5 mL, 2.90 mmol) in anhydrous $CH_2Cl_2$ (1.6 mL) at room temperature. The mixture was washed with 1 M $HCl_{(aq)}$, and extracted with $CH_2Cl_2$ and $H_2O$. The organic phase was dried over $MgSO_4$, filtered, and concentrated under reduced pressure. The residual were then purified by chromatography on a silica gel column with elution of EtOAc/hexane (4:1) to $CH_2Cl_2$/MeOH (40:1) to give compound I-b-3 (72 mg, 26% yield). $C_{16}H_{19}IN_4O_3S$; white solid; mp 100-102° C.; TLC (EtOAc/hexane=8:1) $R_f$=0.2; IR $v_{max}$ (neat) 2923, 2857, 1644, 1584, 1568, 1441, 1332, 1284, 1244, 1021, 789, 681 $cm^{-1}$; $^1H$ NMR (400 MHz, $CDCl_3$) δ 6.93 (1H, s), 4.66 (2H, s), 3.74 (2H, s), 3.63-3.67 (4H, m), 3.55-3.56 (2H, m), 3.46-3.48 (2H, m), 2.71 (3H, s), 2.59 (3H, s); $^{13}C$ NMR (100 MHz, $CDCl_3$) δ 166.8, 165.3, 165.0, 163.4, 163.3, 150.1, 122.7, 114.0, 46.8, 44.6, 44.2, 41.8, 41.6, 24.6, 17.4, −4.7; ESI-HRMS calcd for $C_{16}H_{20}IN_4O_3S$: 475.0301. found: m/z 475.0299 $[M+H]^+$.

1,4-Bis[(3-oxo-4,6-dimethylisothiazolo[5,4-b]pyridin-2-yl)acetyl]piperazine (I-b-4)

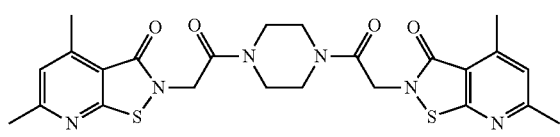

A mixture of 4,6-dimethylisothiazolo[5,4-b]pyridine-3(2H)-one (83 mg, 0.46 mmol), 1,4-bis(iodoacetyl)piperazine (89 mg, 0.21 mmol) and DIEA (0.22 mL, 1.3 mmol) in anhydrous $CH_2Cl_2$ (2.2 mL) was stirred at room temperature for 1.5 h to give a suspension containing brown solids. The suspension was concentrated under reduced pressure and washed with MeOH. The residual solids were collected by centrifugation, rinsed successively with $Et_2O$, $CH_2Cl_2$, EtOAc, $CH_3CN$, and dried in vacuo to give compound I-b-4 (52 mg, 47% yield). $C_{24}H_{26}N_6O_4S_2$; pale yellow solid; mp 258-261° C. (decomposed); TLC (EtOAc/hexane=1:1) $R_f$=0.1; IR $v_{max}$ (neat) 2922, 1656, 1649, 1562, 1478, 1441, 1356, 1236, 1033, 798 $cm^{-1}$; $^1H$ NMR (400 MHz, DMSO-$d_6$); δ 7.17 (2H, s), 4.81-4.79 (4H, m), 3.61 (2H, br, s), 3.55 (4H, br, s), 3.48 (2H, br, s), 2.65 (6H, s), 2.56 (6H, s); ESI-HRMS calcd for $C_{24}H_{27}N_6O_4S_2$: 527.1535. found: m/z 527.1531 $[M+H]^+$.

4-[(3-Oxo-benzo[d]isothiazol-2-yl)acetyl]-1-[(4,6-dimethyl-3-15 oxoisothiazolo[5,4-b]pyridin-2-yl)acetyl]piperazine (I-b-5)

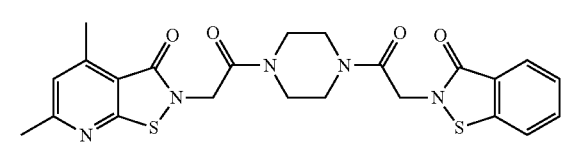

A mixture of 4,6-dimethylisothiazolo[5,4-b]pyridine-3(2H)-one (19.5 mg, 0.11 mmol), 2-[2-(4-(2-iodoacetyl)piperazin-1-yl)-2-oxoethyl]benzo[d]isothiazol-3(2H)-one (I-e-1) (44 mg, 0.98 mmol) and DIEA (0.1 mL, 0.54 mmol) in anhydrous $CH_2Cl_2$ (1 mL) was stirred for 3 h at room temperature. The mixture was washed with 1 M $HCl_{(aq)}$ and extracted with $CH_2Cl_2$ and $H_2O$. The organic phase was dried over $MgSO_4$, filtered, and concentrated to give crude product as brown solids. The solids were washed with MeOH. The supernatant was recrystallized from MeOH and combined to give compound I-b-5 (32 mg, 63% yield); $C_{23}H_{23}N_5O_4S_2$; white solid; mp 127-129° C.; TLC (EtOAc/hexane=8:1) $R_f$=0.1; IR $v_{max}$ (neat) 2926, 2855, 1651, 1446, 1340, 1283, 1225, 986, 829, 781, 741, 669 $cm^{-1}$; $^1H$ NMR (400 MHz, $CDCl_3$) δ 8.01 (1H, dd, J=8.0 Hz), 7.61 (1H, t, J=7.4 Hz), 7.53-7.55 (1H, m), 7.39 (1H, t, J=7.6 Hz), 6.92 (1H, s), 4.69 (2H, s), 4.64 (2H, s), 3.58-3.65 (8H, m), 2.71 (3H, s), 2.59 (3H, s); $^{13}C$ NMR (100 MHz, $CDCl_3$) δ 165.5, 165.2, 165.0, 164.8, 163.1, 163.0, 150.0, 141.0, 132.2, 126.7, 125.5, 123.1, 122.6, 120.3, 114.0, 45.3, 44.8 (2×), 44.3, 42.0 (2×), 24.7, 17.6; ESI-HRMS calcd for $C_{23}H_{24}N_5O_4S_2$: 498.1270 found: m/z 498.1269 $[M+H]^+$.

1,4-Bis[(6-amino-4-methyl-3-oxoisothiazolo[5,4-b]pyridin-2-yl)acetyl]piperazine (I-b-6)

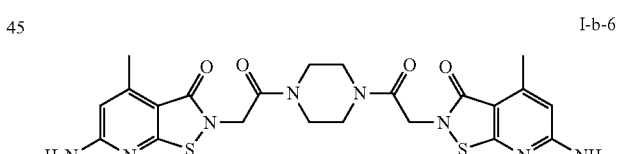

A mixture of 2-mino-4-methylisothiazolo[5,4-b]pyridine-3(2H)-one (55 mg, 0.30 mmol), 1,4-bis(iodoacetyl)piperazine (59 mg, 0.14 mmol) and DIEA (0.15 mL, 0.84 mmol) in anhydrous DMF (1.5 mL) was stirred for 1 h at room temperature. The solution was concentrated under reduced pressure and washed with MeOH to give brown solids. The solids were then purified by C18 reverse-phase chromatography on a silica gel column ($H_2O$/MeOH=70:30) to give compound I-b-6. $C_{22}H_{24}N_8O_4S_2$; white solid; mp 266-268° C.; TLC ($CH_2Cl_2$/MeOH=9:1) $R_f$=0.4; IR $v_{max}$ (neat) 3452, 3348, 3214, 2920, 1649, 1594, 1544, 1444, 1340, 1228, 1123, 1029, 980, 854, 792, 544 $cm^{-1}$; $^1H$ NMR (400 MHz, DMSO-$d_6$) δ 6.92 (4H, s), 6.20 (2H, s), 4.64 (4H, s), 2.46 (6H, s); ESI-HRMS calcd for $C_{22}H_{25}N_8O_4S_2$: 529.1440. found: m/z 529.1444 $[M+H]^+$.

2-(2-Oxo-2-(piperazin-1-yl)ethyl)isothiazolo[5,4-b]pyridin-3(2H)-one (I-c-1)

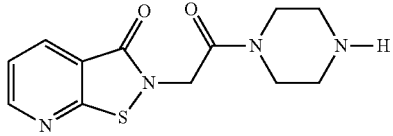

Tert-butyl 4-(2-(3-oxoisothiazolo[5,4-b]pyridin-2(3H)-yl)acetyl)piperazine-1-carboxylate (I-a-1) (363 mg, 1.31 mmol) and TFA (3 mL) was dissolved in anhydrous $CH_2Cl_2$ (10 mL), and then stirred for 0.5 h at 25° C. TFA was removed under reduced pressure, and the residue was extracted with ammonia solution (35%) and $CH_2Cl_2$. The organic layer was dried over $MgSO_4$, filtered, and concentrated to give compound I-c-1 (16 mg, quant. yield). $C_{12}H_{15}N_4O_2S$; white solid; mp 200-201° C.; IR $\nu_{max}$ (neat) 3444, 2925, 2390, 2345, 1667, 1589, 1569, 1471, 1401, 1250, 1201, 1172, 1131, 1038, 837, 801, 760, 719 $cm^{-1}$; $^1H$ NMR (400 MHz, $CD_3OD$) δ 8.83 (1H, dd, J=4.8, 2.0 Hz), 8.34 (1H, dd, J=8.0, 1.6 Hz), 7.53 (1H, dd, J=8.4, 4.8 Hz), 4.89 (2H, s), 3.87 (4H, m), 3.31-3.25 (4H, m); $^{13}C$ NMR (100 MHz, $CD_3OD$) δ 167.1, 166.4, 164.3, 155.6, 136.2, 122.6, 119.9, 45.8, 44.4 (2×), 43.1, 40.3; ESI-HRMS calcd for $C_{12}H_{15}N_4O_2S$: 279.0916. found: m/z 279.0916 $[M+H]^+$.

4,6-Dimethyl-2-(2-oxo-2-(piperazin-1-yl)ethyl)isothiazolo[5,4-b]pyridin-3(2H)-one (I-c-2)

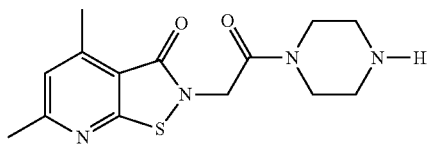

Tert-butyl 4-[4,6-dimethyl-2-(3-oxoisothiazolo[5,4-b]pyridin-2(3H)-yl)acetyl]piperazine-1-carboxylate (66.5 mg, 0.16 mmol) and TFA (1.5 mL) was dissolved in $CH_2Cl_2$ (10 mL), and then stirred for 2 h at 25° C. TFA was removed under reduced pressure, and purified by flash chromatography on a silica gel column with elution of $MeOH/CH_2Cl_2$ (1:5) to give compound I-c-2 (37 mg, 75% yield). $C_{14}H_{18}N_4O_2S$; white solid; $^1H$ NMR (400 MHz, $CD_3OD$) δ 7.01 (1H, s), 4.71 (2H, s), 3.24-3.22 (2H, m), 3.19-3.18 (2H, m), 3.14 (4H, m), 2.58 (3H, s), 2.46 (3H, s); $^{13}C$ NMR (100 MHz, $CD_3OD$) δ 167.4, 166.9, 165.0, 164.5, 152.0, 124.1, 115.6, 48.5, 45.4, 44.4, 43.1, 40.2, 24.5 (2×), 17.7; ESI-HRMS calcd for $C_{14}H_{19}N_4O_2S$: 307.1229. found: m/z 307.1215 $[M+H]^+$.

6-Amino-4-methyl-2-[2-oxo-2-(piperazin-1-yl)ethyl]isothiazolo[5,4-b]pyridin-3(2H)-one (I-c-3)

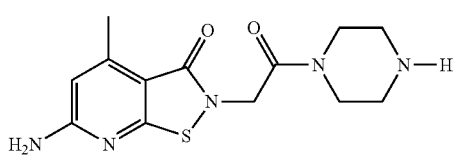

Tert-butyl 4-[(6-amino-4-methyl-3-oxoisothiazolo[5,4-b]pyridin-2(3H)-2-yl)acetyl]piperazine-1-carboxylate (I-a-3) (48 mg, 0.12 mmol) and TFA (1.9 mL, 24.40 mmol) in anhydrous $CH_2Cl_2$ (14 mL) was stirred for 2 h at room temperature. The solution was concentrated under reduced pressure and washed successively with $Et_2O$ and MeOH to give compound I-c-3 as the TFA salt (55 mg, 86% yield). $C_{13}H_{17}N_5O_2S$; white powder; mp 214-216° C.; TLC ($CH_2Cl_2$/MeOH=9:1) $R_f$=0.1; IR $\nu_{max}$ (neat) 3414, 3335, 3228, 2924, 1680, 1648, 1598, 1543, 1444, 1375, 1340, 1249, 1203, 1145, 1026, 799, 723, 545, 465 $cm^{-1}$; $^1H$ NMR (400 MHz, $CD_3OD$) δ 6.31 (1H, s), 4.72 (2H, s), 3.84 (4H, s, br), 3.37-3.84 (2H, m), 3.25-3.26 (2H, m), 2.55 (3H, s); $^{13}C$ NMR (100 MHz, $CD_3OD$) δ 167.9 (2×), 166.4, 163.9, 151.0, 109.2, 108.0, 45.1, 44.5 (2×), 43.1, 40.2, 18.0; ESI-HRMS calcd for $C_{13}H_{18}N_5O_2S$: 308.1181. found: m/z 308.1179 $[M+H]^+$.

Ethyl 4-(2-(3-oxobenzo[d]isothiazol-2(3H)-yl)acetyl)piperazine-1-carboxylate (I-d-1)

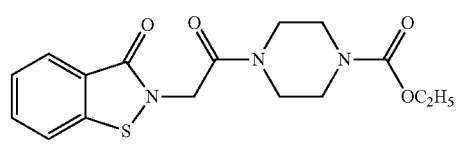

Ethyl 4-(2-iodoacetyl)piperazine-1-carboxylate (200 mg, 0.61 mmol) was added to a suspension of benzo[d]isothiazol-3(2H)-one (102 mg, 0.67 mmol), $Et_3N$ (233 mg, 1.83 mmol) and $Cs_2CO_3$ (198 mg, 0.61 mmol) in anhydrous $CH_2Cl_2$ (8 mL) at room temperature. The mixture was stirred for 26 h, and washed with 1 M $HCl_{(aq)}$. The organic phase was dried over $MgSO_4$, filtered, concentrated, and purified by flash chromatography on a silica gel column with elution of EtOAc/hexane (1:2) to give compound I-d-1 (134 mg, 63% yield). The purity of product I-d-1 was 99.3% as shown by HPLC on an HC-C18 column (Agilent, 4.6×250 mm, 5 μM), $t_R$=11.87 min (gradients of 20-90% aqueous $CH_3CN$ in 20 min). $C_{16}H_{19}N_3O_4S$; white solid; mp 158-160° C.; $^1H$ NMR (400 MHz, $CDCl_3$) δ 8.09 (1H, dd, J=7.2 Hz, 0.8 Hz), 7.59 (1H, m), 7.53 (1H, dd, J=7.2, 0.8 Hz), 7.38 (1H, m), 4.69 (2H, s), 4.13 (2H, q, J=7.2 Hz), 3.60 (2H, m), 3.55 (2H, m), 3.48 (4H, m), 1.25 (3H, t, J=7.2 Hz); $^{13}C$ NMR (100 MHz, $CDCl_3$) δ 164.6, 154.6, 140.8, 131.8, 130.0, 126.4, 125.1, 122.9, 120.0, 61.9, 45.3, 45.0, 43.5 (2×), 42.2, 15.0; ESI-HRMS calcd for $C_{16}H_{19}N_3O_4S$: 372.0994. found: m/z 372.0992 $[M+H]^+$.

Tert-butyl 4-(2-(3-oxobenzo[d]isothiazol-2(3H)-yl)acetyl)piperazine-1-carboxylate (I-d-2)

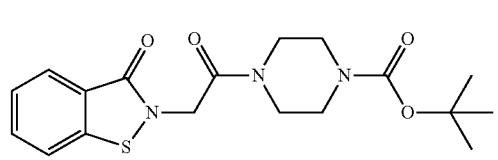

Benzo[d]isothiazol-3(2H)-one (1.20 g, 7.94 mmol) was added to a solution of benzo[d]isothiazol-3(2H)-one (2.80 g, 7.95 mmol), Et$_3$N (5.4 mL, 38.7 mmol) and Cs$_2$CO$_3$ (3.88 g, 11.9 mmol) in CH$_2$Cl$_2$ (123 mL) at room temperature. The mixture was stirred for 4 h, and then extracted with CH$_2$Cl$_2$ and H$_2$O. The combined organic phase was washed with brine, dried over MgSO$_4$ and concentrated under reduced pressure. After flash column chromatography (silica gel, hexane/EtOAc (1:1 to 1:2)), the product I-d-2 was obtained (1.60 g, 60% yield). The purity of product I-d-2 was 96.9% as shown by HPLC on an HC-C18 column (Agilent, 4.6× 250 mm, 5 μM), $t_R$=16.6 min (gradients of 20-90% aqueous CH$_3$CN in 20 min). C$_{18}$H$_{23}$N$_3$O$_2$S; white solid, mp 169-170° C.; IR $v_{max}$ (neat) 2974, 2925, 1655, 1460, 1418, 1364, 1339, 1285, 1171, 1128, 1068, 1028 740 cm$^{-1}$; $^1$H NMR (400 MHz, CDCl$_3$) δ 8.01 (1H, d, J=7.7 Hz), 7.60 (1H, td, J=7.7, 0.8 Hz), 7.53 (1H, d, J=7.7 Hz), 7.38 (1H, t, J=7.7 Hz), 4.68 (2H, s), 3.58 (2H, m), 3.52 (2H, m), 3.42-3.40 (4H, m), 1.43 (9H, s); $^{13}$C NMR (100 MHz, CDCl$_3$) δ 165.6, 165.1, 154.3, 141.2, 132.1, 126.7, 125.4, 123.2, 120.3, 80.3, 45.0, 44.7 (2×), 41.9 (2×), 28.2 (3×); ESI-HRMS calcd for C$_{18}$H$_{24}$N$_3$O$_4$S: 378.1488. found m/z 378.1488 [M+H]$^+$.

Benzyl 4-(2-(3-oxobenzo[d]isothiazol-2(3H)-yl)acetyl)piperazine-1-carboxylate (I-d-3)

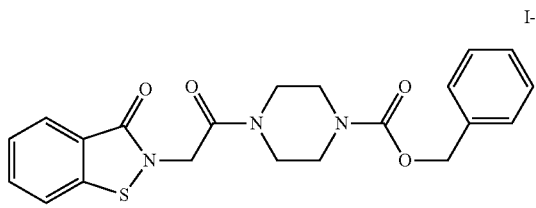

I-d-3

Benzyl chloroformate (75 mg, 0.44 mmol) was added into a mixture of 2-(2-oxo-2-(piperazin-1-yl)ethyl)benzo[d]isothiazol-3(2H)-one (I-f-1) 100 mg, 0.36 mmol) and DIEA (140 mg, 1.10 mmol) in anhydrous CH$_2$Cl$_2$ (5 mL) and DMF (1 mL) at room temperature for 4 h. CH$_2$Cl$_2$ and DMF were removed in reduced pressure. The mixture was washed successional with 1 M HCl$_{(aq)}$ and saturated NaHCO$_{3(aq)}$. The organic phase was dried over MgSO$_4$, filtered, concentrated, and the product I-d-3 was obtained after purification on a thin-layer plate (20 cm×20 cm×2 mm) using CH$_2$Cl$_2$/MeOH (9:1) as the developing solution. C$_{21}$H$_{21}$N$_3$O$_4$S; white solid; mp 138-142° C.; IR $v_{max}$ (neat) 2923, 2854, 1700, 1655, 1428, 1354, 1286, 1227, 1125, 1075, 1027, 984, 861, 741 cm$^{-1}$; $^1$H NMR (400 MHz, CDCl$_3$) δ 8.01 (1H, d, J=8.0 Hz), 7.60 (1H, t, J=7.2 Hz), 7.53 (1H, d, J=8.0 Hz), 7.36 (6H, m), 5.12 (2H, s), 4.69 (2H, s), 3.62 (8H, m); $^{13}$C NMR (100 MHz, CDCl$_3$) δ 165.1, 154.8, 141.1, 136.1, 132.1, 128.5, 128.1, 127.9, 126.7 (2×), 126.3 (2×), 125.4, 123.2, 120.2, 67.6, 45.2, 44.9, 43.6 (2×), 42.0; ESI-HRMS calcd for C$_{21}$H$_{21}$N$_3$O$_4$NaS: 434.1150. found: m/z 434.1149 [M+H]$^+$.

4-Nitrophenyl 4-(2-(3-oxobenzo[d]isothiazol-2(3H)-yl)acetyl)piperazine-1-carboxylate (I-d-4)

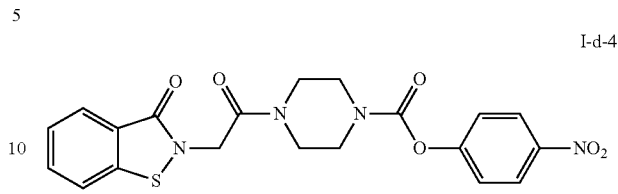

I-d-4

4-Nitrophenyl carbonochloridate (213 mg, 1.06 mmol) was added to a mixture of 2-(2-oxo-2-(piperazin-1-yl)ethyl)benzo[d]isothiazol-3(2H)-one (I-f-1) (81.5 mg, 0.29 mmol) and DMAP (108 mg, 0.88 mmol) in anhydrous CH$_2$Cl$_2$ (4 mL) at room temperature for 16 h. The mixture was washed successional with saturated NaHCO$_{3(aq)}$ and 1 M HCl$_{(aq)}$ until the solution became transparent. The organic phase was dried over MgSO$_4$, filtered, concentrated, and purified by flash chromatography on a silica gel column with elution of CH$_2$Cl$_2$/MeOH (100:0.5 to 9:1) to give product I-d-4 (70 mg, 56% yield). C$_{20}$H$_{18}$N$_4$O$_6$S; pale yellow solid; mp 114-118° C.; IR $v_{max}$ (neat) 2923, 2854, 1725, 1655, 1520, 1346, 1259, 1163, 1111, 1056, 1024, 862, 748 cm$^{-1}$; $^1$H NMR (400 MHz, CDCl$_3$) δ 8.22 (2H, d, J=10.2 Hz), 8.02 (1H, d, J=8.0 Hz), 7.62 (2H, t, J=8.0 Hz), 7.55 (1H, d, J=8.0 Hz), 7.40 (1H, t, J=8.0 Hz), 7.27 (1H, d, J=10.2 Hz), 4.73 (2H, s), 3.70 (6H, br s), 3.62 (2H, br s); $^{13}$C NMR (100 MHz, CDCl$_3$) δ 165.4, 165.1, 155.5, 151.7, 144.7, 141.0, 132.1, 126.5, 125.4, 124.9 (2×), 123.0, 122.0 (2×), 120.2, 44.7, 44.5, 44.2, 43.8, 43.6; ESI-HRMS calcd for C$_{20}$H$_{19}$N$_4$O$_6$S: 443.1025. found: m/z 443.1042 [M+H]$^+$.

Tert-butyl 4-(2-(4-fluoro-3-oxobenzo[d]isothiazol-2(3H)-yl)acetyl)piperazine-1-carboxylate (I-d-5)

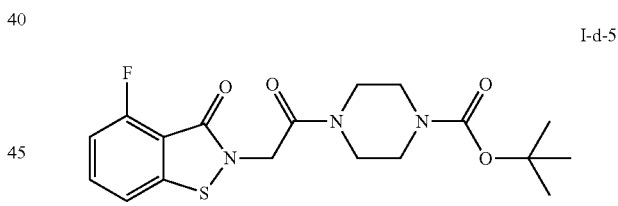

I-d-5

A mixture of 2,6-difluorobenzonitrile (380 mg, 2.74 mmol) and Na$_2$S (0.22, 2.88 mmol) in DMF (8 mL) was stirred at room temperature for 17 h. The residue was extracted by 1 M HCl and Et$_2$O. The organic phase was concentrated under reduced pressure to afford the crude product 6-fluoro-2-mercaptobenzonitrile (387 mg, 92% yield).

The above-prepared thiol compound (300 mg, 1.96 mmol) was added to conc. H$_2$SO$_4$ (2 mL). The mixture was immersed in a preheated oil bath at 100° C. for 5 h, and then cooled. The mixture was modulated to pH 5-6 by addition of saturated NaHCO$_{3(aq)}$ to produce insoluble substance in suspension. The solids were collected by filtration, and dried in vacuo to give a crude product of 4-fluorobenzo[d]isothiazol-3[2H]-one (77 mg, 23% yield). C$_7$H$_4$FNOS; off-white solid.

A mixture of the above-prepared isothiazolone compound (0.077 g, 0.46 mmol), tert-butyl 4-(2-iodoacetyl)piperazine-1-carboxylate (0.184, 0.52 mmol) and DIEA (0.16 mL, 0.95 mmol) in THF (3 mL) was stirred for 5 h at room temperature. The mixture was concentrated under reduced pressure. The residue was extracted with $CH_2Cl_2$ and $H_2O$. The organic phase was dried over $MgSO_4$, filtered, concentrated, and purified by flash chromatography on a silica gel column with elution of EtOAc/hexane (1:1, 2:1, and EtOAc) to give compound I-d-5 (41 mg, 22% yield). The purity of product I-d-5 was 95.1% as shown by HPLC on DIKMA column (Agilent, 4.6×250 mm, 5 m), $t_R$=7.1 min with elution of EtOAc at a flow rate of 1.0 mL/min for 30 min. $C_{18}H_{22}N_3O_4FS$; white solid; mp 201-203° C.; IR $v_{max}$ (neat) 2979, 2926, 2862, 1660, 1608, 1472, 1418, 1365, 1286, 1252, 1236, 1169, 461, 450, 442, 430, 418, 407, 403 cm$^{-1}$; $^1$H NMR (400 MHz, CDCl$_3$) δ 7.55 (1H, m), 7.29 (1H, m), 6.99 (1H, m), 4.65 (2H, s), 3.60-3.58 (2H, m), 3.56-3.54 (2H, m), 3.47-3.41 (4H, m), 1.45 (9H, s); $^{13}$C NMR (100 MHz, CDCl$_3$) δ 165.1, 162.5, 159.9, 154.4, 143.7 (d, $J_{F-C}$=13.2 Hz), 133.6 (d, $J_{F-C}$=32 Hz), 116.3 (d, $J_{F-C}$=18.8 Hz), 111.8 (d, $J_{F-C}$=77.6 Hz), 80.5, 45.2, 44.5 (2×), 42.0 (2×), 28.3 (3×); ESI-HRMS calcd for $C_{18}H_{22}FN_3NaO_4S$: 418.1208. found: m/z 418.1207 [M+Na]$^+$.

Tert-butyl 4-(2-(5-fluoro-3-oxobenzo[d]isothiazol-2 (3H)-yl)acetyl)piperazine-1-carboxylate (I-d-6)

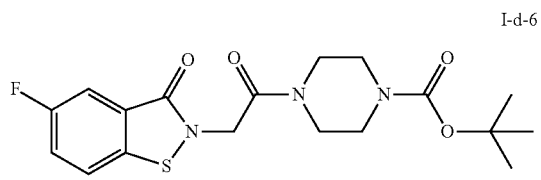 [SMILES: CC(C)(C)OC(=O)N1CCN(C(=O)Cn2sc3ccc(F)cc3c2=O)CC1]

I-d-6

Sodium sulfide nonahydrate (220 mg, 2.82 mmol) was added into a solution of 2,5-difluorobenzonitrile (400 mg, 2.88 mmol) in DMF and stirred at 25° C. for 13 h. The solvent was removed and washed with $CH_2Cl_2$ and 1 M $NaOH_{(aq)}$. The aqueous layer was slowly added 1 M $HCl_{(aq)}$ and monitored to pH=1-2. The suspension containing light yellow solids was filtered, rinsed with water, and dried under reduced pressure to give 5-fluoro-2-mercaptobenzonitrile (220 mg, 50%).

Concentrated $H_2SO_4$ (0.9 mL) was added to the above-prepared thiol compound (120 mg, 0.78 mmol) in a round-bottomed flask. The mixture was immersed into a pre-heated oil bath at 100° C. for 4 h. The mixture was cooled to 0° C. and modulated to pH=5-6☐ by batch-wise addition of $NaHCO_{3(s)}$, producing insoluble substance in suspension. The solids were collected by filtration, dried under reduced pressure to give 5-fluorobenzo[d]isothiazol-3[2H]-one (31 mg, 23% yield).

The above-prepared isothiazolone compound (107 mg, 0.63 mmol) was added to a solution of tert-butyl 4-(2-iodoacetyl)piperazine-1-carboxylate (246 mg, 0.63 mmol) and DIEA (0.22 ml, 1.26 mmol) in THF (3.1 ml) at room temperature. The mixture was stirred for 4 h, and the solvent was removed. The residue was extracted with $CH_2Cl_2$ and $H_2O$, and the combined organic phase was washed with brine, dried over $MgSO_4$, filtered, concentrated to afford the crude product. After flash column chromatography (silica gel, hexane/EtOAc (1:1) to EtOAc), the desired product I-d-6 (110 mg, 44% yield) was obtained. $C_{18}H_{22}FN_3O_4S$; white solid; $^1$H NMR (400 MHz, CDCl$_3$) δ 7.69 (1H, dd, J=8.3, 2.9 Hz), 7.50 (1H, dd, J=8.3, 2.9 Hz), 7.37 (1H, td, J=8.3, 2.9 Hz), 4.68 (2H, s), 3.61-3.51 (4H, m), 3.47-3.41 (4H, m), 1.44 (9H, s); $^{13}$C NMR (100 MHz, CDCl$_3$) δ 165.0, 162.3, 159.9, 154.4, 136.6, 124.8 (d, J=33.6 Hz), 121.9 (d, J=15.2 Hz), 121.1 (d, J=50.0 Hz), 112.7 (d, J=97.2 Hz) 80.5, 45.1, 44.9, 43.6 (2×), 42.0, 28.3 (3×); ESI-HRMS calcd for $C_{18}H_{23}N_3O_4FS$: 396.1393. found m/z 396.1375 [M+H]$^+$.

Tert-butyl 4-(2-(6-fluoro-3-oxobenzo[d]isothiazol-2 (3H)-yl)acetyl)piperazine-1-carboxylate (I-d-7)

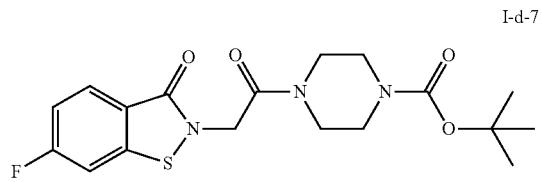 [SMILES: CC(C)(C)OC(=O)N1CCN(C(=O)Cn2sc3cc(F)ccc3c2=O)CC1]

I-d-7

A mixture of 2,3-difluorobenzonitrile (400 mg, 2.88 mmol) and $Na_2S$ (0.22, 2.88 mmol) in DMF (8 mL) was stirred at room temperature for 17 h. After addition of 1 M NaOH (30 mL), the mixture was washed with $CH_2Cl_2$ (4×30 mL). The aqueous layer was acidified with 1 M HCl to pH 1-2 to produce insoluble substance in suspension. The solids were collected by filtration, and dried in vacuo to give a crude product of 4-fluoro-2-mercaptobenzonitrile (363 mg, 83% yield).

The above-prepared thiol compound (107 mg, 0.70 mmol) was added to conc. $H_2SO_4$ (1 mL). The mixture was immersed in a preheated oil bath at 100° C. for 4 h, and then cooled. The mixture was modulated to pH 5-6 by addition of saturated $NaHCO_3$ to produce insoluble substance in suspension. The solids were collected by filtration, and dried in vacuo to give a crude product of 6-fluorobenzo[d]isothiazol-3[2H]-one (67 mg, 57% yield). $C_7H_4FNOS$; off-white solid; ES-HRMS calcd for $C_7H_3NOFS$: 167.9919. found: m/z 167.9926 [M–H]$^-$.

A mixture of the above-prepared isothiazolone compound (0.10 g, 0.65 mmol), tert-butyl 4-(2-iodoacetyl)piperazine-1-carboxylate (0.25, 0.72 mmol) and DIEA (0.21 mL, 1.3 mmol) in THF (4 mL) was stirred for 4 h at room temperature. The mixture was concentrated under reduced pressure. The residue was extracted with $CH_2Cl_2$ and $H_2O$. The organic phase was dried over $MgSO_4$, filtered, concentrated, and purified by flash chromatography on a silica gel column with elution of EtOAc/hexane (1:1, 2:1, and EtOAc) to give compound I-d-7 (0.14 g, 61% yield). The purity of product I-d-7 was 96.8% as shown by HPLC on DIKMA column (Agilent, 4.6×250 mm, 5 m), $t_R$=9.04 min with elution of EtOAc at a flow rate of 1.0 mL/min for 40 min. $C_{18}H_{22}N_3O_4FS$; white solid; mp 229-231° C.; IR $v_{max}$ (neat) 2985, 2938, 2862, 1695, 1655, 1614, 1468, 1421, 1368, 1287, 1176, 1124, 1030, 1001, 908, 861, 762 cm$^{-1}$; $^1$H NMR (400 MHz, CDCl$_3$) δ 8.02 (1H, m), 7.22 (1H, m), 7.13 (1H, m), 4.67 (2H, s), 3.61-3.59 (2H, m), 3.53-3.52 (2H, m), 3.46-3.41 (4H, m), 1.45 (9H, s); $^{13}$C NMR (100 MHz, CDCl$_3$) δ 180.4, 166.6 ($J_{F-C}$=252.3 Hz), 154.4, 143.4, 129.8, 128.9 (d, $J_{F-C}$=10.0 Hz), 119.7, 114.6 (d, $J_{F-C}$=24.0 Hz), 107.1 (d, $J_{F-C}$=26.7 Hz), 80.5, 45.1 (2×), 44.8, 42.0 (2×), 28.3 (3×); ESI-HRMS calcd for $C_{18}H_{23}N_3O_4FS$: 396.1393. found: m/z 396.1393 [M+H]$^+$.

Tert-butyl 4-(2-(7-fluoro-3-oxobenzo[d]isothiazol-2 (3H)-yl)acetyl)piperazine-1-carboxylate (I-d-8)

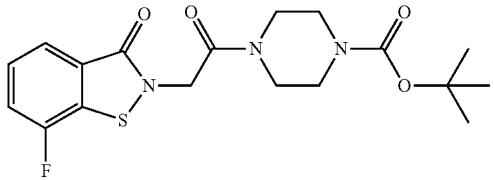

I-d-8

A mixture of 2,3-difluorobenzonitrile (400 mg, 2.88 mmol) and Na$_2$S (0.22, 2.88 mmol) in DMF (8 mL) was stirred at room temperature for 19 h. The residue was extracted with H$_2$O and CH$_2$Cl$_2$. The organic phase was concentrated to afford the crude product of 3-fluoro-2-mercaptobenzonitrile (377 mg, 86% yield).

The above-prepared thiol compound (300 mg, 1.96 mmol) was added to conc. H$_2$SO$_4$ (2 mL). The mixture was immersed in a preheated oil bath at 100° C. for 5 h, and then cooled. The mixture was modulated to pH 5-6 by addition of saturated NaHCO$_{3(aq)}$ to produce insoluble substance in suspension. The solids were collected by filtration, and dried in vacuo to give a crude product of 7-fluorobenzo[d]isothiazol-3[2H]-one (188 mg, 56% yield). C$_7$H$_4$FNOS; off-white solid.

A mixture of the above-prepared isothiazolone compound (0.11 g, 0.65 mmol), tert-butyl 4-(2-iodoacetyl)piperazine-1-carboxylate (0.25, 0.72 mmol) and DIEA (0.54 mL, 3.3 mmol) in THF (3.5 mL) was stirred for 6 h at room temperature. The mixture was concentrated under reduced pressure. The residue was extracted with CH$_2$Cl$_2$ and H$_2$O. The organic phase was dried over MgSO$_4$, filtered, concentrated, and purified by flash chromatography on a silica gel column with elution of EtOAc/hexane (1:1, 2:1, and EtOAc) to give compound I-d-8 (0.075 g, 29% yield). The purity of product I-d-8 was 95.5% as shown by HPLC on DIKMA column (Agilent, 4.6×250 mm, 5 μm), t$_R$=6.8 min with elution of EtOAc at a flow rate of 1.0 mL/min for 30 min. C$_{18}$H$_{22}$N$_3$O$_4$FS; white solid; mp 169-170° C.; IR ν$_{max}$ (neat) 2977, 2930, 2865, 1671, 1577, 1481, 1459, 1420, 1366, 1344, 1286, 1252, 1236, 1169, 1128, 1022, 996, 863, 803, 787, 771, 743, 581, 528, 458, 446 cm$^{-1}$; $^1$H NMR (400 MHz, CDCl$_3$) δ 7.86 (1H, m), 7.40 (1H, m), 7.33 (1H, m), 4.71 (2H, s), 3.64-3.61 (2H, m), 3.56-3.53 (2H, m), 3.50-3.44 (4H, m), 1.47 (9H, s); $^{13}$C NMR (100 MHz, CDCl$_3$) δ 164.9, 156.5, 154.2 (d, J$_{F-C}$=139.6 Hz), 128.8 (J$_{F-C}$=80.4 Hz), 127.2 (J$_{F-C}$=24.0 Hz), 126.3 (d, J$_{F-C}$=13.6 Hz), 122.5 (d, J$_{F-C}$=13.2 Hz), 117.7 (d, J$_{F-C}$=69.6 Hz), 80.5, 45.1 (2×), 44.9, 42.0 (2×), 28.3 (3×); ESI-HRMS calcd for C$_{18}$H$_{23}$N$_3$O$_4$FS: 396.1393. found: m/z 396.1394 [M+H]$^+$.

Tert-butyl 4-(2-(6-chloro-3-oxobenzo[d]isothiazol-2 (3H)-yl)acetyl)piperazine-1-carboxylate (I-d-9)

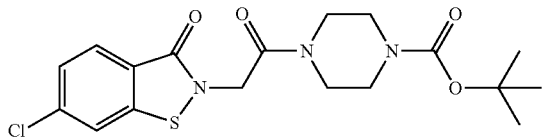

I-d-9

A mixture of 4-chloro-2-fluorobenzonitrile (400 mg, 2.57 mmol) and Na$_2$S (0.20, 2.57 mmol) in DMF (8 mL) was stirred at room temperature for 19 h. After addition of H$_2$O, the mixture was participated with CH$_2$Cl$_2$. The organic layer was concentrated under reduced pressure to give a crude product of 4-chloro-2-mercaptobenzonitrile (268 mg, 62% yield).

The above-prepared thiol compound (183 mg, 1.08 mmol) was added to conc. H$_2$SO$_4$ (1 mL). The mixture was immersed in a preheated oil bath at 100° C. for 4 h, and then cooled. The mixture was modulated to pH 5-6 by addition of saturated NaHCO$_3$ to produce insoluble substance in suspension. The solids were collected by filtration, and dried in vacuo to give a crude product of 6-chlorobenzo[d]isothiazol-3[2H]-one (59 mg, 43% yield).

A mixture of the above-prepared isothiazolone compound (0.05 g, 0.27 mmol), tert-butyl 4-(2-iodoacetyl)piperazine-1-carboxylate (0.11, 0.30 mmol) and DIEA (0.09 mL, 0.54 mmol) in THF (2 mL) was stirred for 6 h at room temperature. The mixture was concentrated under reduced pressure. The residue was extracted with CH$_2$Cl$_2$ and H$_2$O. The organic phase was dried over MgSO$_4$, filtered, concentrated, and purified by flash chromatography on a silica gel column with elution of EtOAc/hexane (1:1) to give compound I-d-9 (0.05 g, 42% yield). The purity of product I-d-9 was 97.7% as shown by HPLC on DIKMA column (Agilent, 4.6×250 mm, 5 m), t$_R$=7.51 min with elution of EtOAc at a flow rate of 1.0 mL/min for 15 min. C$_{18}$H$_{22}$N$_3$O$_4$SCl; white solid; $^1$H NMR (400 MHz, CDCl$_3$) δ 7.94 (1H, d, J=8.8 Hz), 7.54 (1H, d, J=1.6 Hz), 7.36 (1H, dd, J=8.8, 2.0 Hz), 4.67 (2H, s), 3.59-3.58 (2H, m), 3.52-3.51 (2H, m), 3.46-3.41 (4H, m), 1.44 (9H, s); $^{13}$C NMR (100 MHz, CDCl$_3$) δ 165.0, 164.9, 154.4, 142.8, 138.9, 127.8, 126.5, 121.8, 120.1, 80.5, 45.1 (2×), 44.8, 42.0 (2×), 28.3 (3×); ESI-HRMS calcd for C$_{18}$H$_{23}$N$_3$O$_4$SCl: 412.1098. found: m/z 412.1083 [M+H]$^+$.

Tert-butyl 4-(2-(6-bromo-3-oxobenzo[d]isothiazol-2 (3H)-yl)acetyl)piperazine-1-carboxylate (I-d-10)

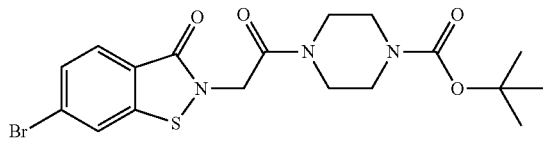

I-d-10

A mixture of 4-bromo-2-fluorobenzonitrile (2.00 g, 10 mmol) and Na2S (0.93, 12 mmol) in DMF (10 mL) was stirred at room temperature for 15 h. After addition of 1 M NaOH (70 mL), the mixture was washed with CH2Cl2 (4×30 mL). The aqueous layer was acidified with 6 M HCl to pH 1-2 and extracted with CH2Cl2. The combined organic layer was washed with brine, dried over MgSO4, filtered, and concentrated under reduced pressure to give 4-bromo-2-mercaptobenzonitrile (2.01 g, 93% yield). C7H4BrNS; yellow solid; mp 106-107° C.; 1H NMR (400 MHz, CDCl3): δ 7.57 (1H, d, J=1.6 Hz), 7.44 (1H, d, J=8.4 Hz), 7.36 (1H, dd, J=8.0, 1.6 Hz), 4.11 (1H, s); 13C NMR (100 MHz, CDCl3): δ 139.4, 134.2, 131.9, 129.1, 127.9, 116.8, 110.5; MS (m/z); ESI-HRMS calcd for C7H3BrNS: 211.9170. found: m/z 211.9179 [M−H]$^-$.

The above-prepared thiol compound (600 mg, 2.80 mmol) was added to conc. H$_2$SO$_4$ (5 mL). The mixture was immersed in a preheated oil bath at 100° C. for 5 h, and then cooled. The mixture was modulated to pH 5-6 by addition of saturated NaHCO$_3$ to produce insoluble substance in suspension. The solids were collected by filtration, and dried in vacuo to give 6-bromobenzo[d]isothiazol-3(2H)-one (603 mg, 94% yield). C$_7$H$_4$BrNOS; yellow powder; mp 194-196° C.; IR $v_{max}$ (neat) 2922, 2851, 1716, 1575, 1541, 1368, 1286, 1267, 1245, 1087, 1048, 978, 816, 663 cm$^{-1}$; $^1$H NMR (400 MHz, CD$_3$OD) δ 7.98 (1H, s), 7.75 (1H, d, J=8 Hz), 7.49 (1H, dd, J=8.4, 1.6 Hz) 7.86 (1H, d, J 8.4 Hz), 7.71 (1H, d, J 1.2 Hz); $^{13}$C NMR (100 MHz, DMSO-d$_6$) δ 164.0, 150.0, 128.0, 125.5, 124.1, 123.9 (2×); ESI-HRMS (negative mode) calcd for C$_7$H$_3$BrNOS: 227.9119. found: m/z 227.9130 [M−H]$^−$.

A mixture of the above-prepared isothiazolone compound (760 mg, 3.32 mmol), tert-butyl 4-(2-iodoacetyl)piperazine-1-carboxylate (1293 mg, 3.65 mmol) and DIEA (1.72 mL, 9.96 mmol) in THF (20 mL) was stirred for 4 h at room temperature. The mixture was concentrated under reduced pressure. The residue was extracted with CH$_2$Cl$_2$ and H$_2$O. The organic phase was dried over MgSO$_4$, filtered, concentrated, and purified by flash chromatography on a silica gel column with elution of EtOAc/hexane (1:1) to give compound I-d-10 (622 mg, 41% yield). The purity of product I-d-10 was 95.3% as shown by HPLC on DIKMA column (Agilent, 4.6×250 mm, 5 m), t$_R$=29.2 min with elution of EtOAc/Hex (1:1) at a flow rate of 1.5 mL/min for 50 min. C$_{18}$H$_{22}$BrN$_3$O$_4$S; yellow solid; mp 193-195° C.; IR $v_{max}$ (neat) 2975, 2925, 2860, 1654, 1588, 145 7, 1418, 1365, 1286, 1235, 1168, 1127, 1028, 996, 666 cm$^{-1}$; $^1$H NMR (400 MHz, CDCl$_3$) δ7.86 (1H, d, J 8.4 Hz), 7.71 (1H, d, J 1.2 Hz), 7.50 (1H, dd, J 8.4, 1.2 Hz), 4.66 (2H, s), 3.58-3.57 (2H, m), 3.51-3.50 (2H, m), 3.46-3.41 (4H, m), 1.46 (9H, s); $^{13}$C NMR (100 MHz, CDCl$_3$) δ 165.0 (2×), 154.4, 143.0, 129.1, 127.9, 127.1, 123.0, 122.2, 80.5, 45.1 (2×), 44.8, 42.0 (2×), 28.3 (3×); ESI-HRMS calcd for C$_{18}$H$_{23}$BrN$_3$O$_4$S: 456.0593. found: m/z 456.0591 [M+H]$^+$.

4-Nitrophenyl 4-(2-(6-bromo-3-oxobenzo[d]isothiazol-2(3H)-yl)acetyl)piperazine-1-carboxylate (I-d-11)

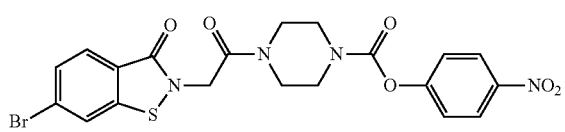

I-d-11

A mixture of 6-bromo-2-(2-oxo-2-(piperazin-1-yl)ethyl)benzo[d]isothiazol-3(2H)-one (I-f-2) (128 mg, 0.25 mmol), 4-nitrophenyl chloroformate (170 mg, 0.86 mmol) and DMAP (90 mg, 0.74 mmol) in CH$_2$Cl$_2$ (0.5 mL) was stirred for 18 h at room temperature. The mixture was concentrated under reduced pressure, and the residue was extracted with CH$_2$Cl$_2$ and saturated NaHCO$_{3(aq)}$. The organic phase was dried over MgSO$_4$, filtered, concentrated, and purified by flash chromatography on a silica gel column with elution of MeOH/CH$_2$Cl$_2$ (1:100 to 1:9) to give compound I-d-11 (10 mg, 21% yield). C$_{20}$H$_{17}$N$_4$O$_6$SBr; yellow solid; mp 216-218° C.; $^1$H NMR (400 MHz, CDCl$_3$) δ 8.26 (2H, dd, J=7.2, 2.4 Hz), 7.89 (1H, d, J=8.4 Hz), 7.73 (1H, d, J=0.8 Hz), 7.53 (1H, dd, J=8.4, 1.6 Hz), 7.30 (2H, dd, J=6.8, 2.0 Hz), 4.71 (2H, s), 3.73 (8H, m); 13C NMR (100 MHz, CDCl$_3$) δ 165.2 (2×), 155.8, 145.1 (2×), 142.9, 129.3, 128.0, 127.3, 125.2 (2×), 123.1, 122.2 (2×), 122.1, 44.7, 43.9 (2×), 41.8 (2×); ES-HRMS calcd for C$_{20}$H$_{18}$N$_4$O$_6$SBr: 521.0140. found: m/z 521.0140 [M+H]$^+$.

Tert-butyl4-(2-(3-oxo-6-(trifluoromethyl)benzo[d]isothiazol-2(3H)-yl)acetyl)-piperazine-1-carboxylate (I-d-12)

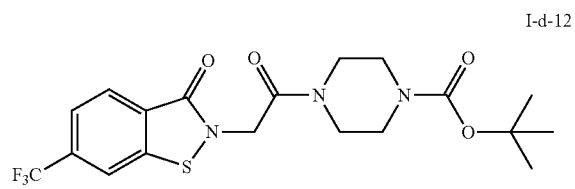 [SMILES: CC(C)(C)OC(=O)N1CCN(C(=O)Cn2sc3cc(C(F)(F)F)ccc3c2=O)CC1]

I-d-12

A mixture of 2-fluoro-4-trifluoromethylbenzonitrile (1.00 g, 5.29 mmol) and Na$_2$S (0.41, 5.29 mmol) in DMF (5 mL) was stirred at room temperature for 5 h. After addition of 1 M NaOH (30 mL), the mixture was washed with CH$_2$Cl$_2$ (4×30 mL). The aqueous layer was acidified with 6 M HCl to pH 1-2 and extracted with CH$_2$Cl$_2$. The combined organic layer was washed with brine, dried over MgSO$_4$, filtered, and concentrated under reduced pressure to a crude product of 2-mercapto-4-(trifluoromethyl)benzonitrile (0.47 g, 43% yield). C$_8$H$_4$F$_3$NS; yellow oil; ES-HRMS calcd for C$_8$H$_3$NF$_3$S: 201.9938. found: m/z 201.9946 [M−H]$^−$.

The above-prepared thiol compound (450 mg, 2.21 mmol) was added to conc. H$_2$SO$_4$ (2 mL). The mixture was immersed in a preheated oil bath at 100° C. for 4 h, and then cooled. The mixture was modulated to pH 5-6 by addition of saturated NaHCO$_3$ to produce insoluble substance in suspension. The solids were collected by filtration, and dried in vacuo to give a crude product of 6-(trifluoromethyl)benzo[d]isothiazol-3(2H)-one (443 mg, 91% yield). C$_8$H$_4$F$_3$NOS; yellow solid; ES-HRMS calcd for C$_8$H$_3$F$_3$NOS: 217.9887. found: m/z 217.9887 [M−H]$^−$.

A mixture of the above-prepared isothiazolone compound (I-f-4) (97 mg, 0.65 mmol), tert-butyl 4-(2-iodoacetyl)piperazine-1-carboxylate (30 mg, 0.85 mmol) and DIEA (0.21 mL, 1.3 mmol) in THF (4 mL) was stirred for 4 h at room temperature. The mixture was concentrated under reduced pressure. The residue was extracted with CH$_2$Cl$_2$ and H$_2$O. The organic phase purified by flash chromatography on a silica gel column with elution of EtOAc/hexane (1:1) to give compound I-d-12 (150 mg, 66% yield). The purity of product I-d-12 was 97.2% as shown by HPLC on DIKMA column (Agilent, 4.6×250 mm, 5 μm), t$_R$=28.4 min with elution of EtOAc/hexane (1:1) at a flow rate of 1.0 mL/min for 40 min. C$_{19}$H$_{22}$F$_3$N$_3$O$_4$S; yellow solid; mp 139-141° C.; IR $v_{max}$ (neat) 2985, 2932, 2867, 1703, 1659, 1634, 1461, 1421, 1324, 1287, 1229, 1169, 1124, 1084, 1032, 996, 838, 770, 722, 688 cm$^{-1}$; $^1$H NMR (400 MHz, CDCl$_3$) δ 8.14 (1H, d, J=8.4 Hz), 7.84 (1H, s), 7.62 (1H, d, J=8.4 Hz), 4.71 (2H, s), 3.60-3.58 (2H, m), 3.52 (2H, brs), 3.48-3.47 (2H, m), 3.48-3.47 (2H, m), 3.44-3.42 (2H, m), 1.44 (9H, s); $^{13}$C NMR (100 MHz, CDCl$_3$) δ 164.8 (J$_{F-C}$=6.0 Hz), 154.4, 141.9, 134.4 (J$_{F-C}$=32.6 Hz), 127.5, 125.9, 124.8, 122.3 (J$_{F-C}$=31.1 Hz), 122.0, 118.0 (d, J$_{F-C}$=3.8 Hz), 80.6, 45.1 (2×), 44.8, 42.0 (2×), 28.3 (3×); ESI-HRMS calcd for C$_{19}$H$_{22}$N$_3$O$_4$F$_3$SNa: 468.1181. found: m/z 468.1176 [M+Na]$^+$.

Tert-butyl 4-(2-(6-amino-3-oxobenzo[d]isothiazol-2 (3H)-yl)acetyl)piperazine-1-carboxylate (I-d-13) and tert-butyl 4-(2-(6-azido-3-oxobenzo[d]isothiazol-2 (3H)-yl)acetyl)piperazine-1-carboxylate (I-d-14)

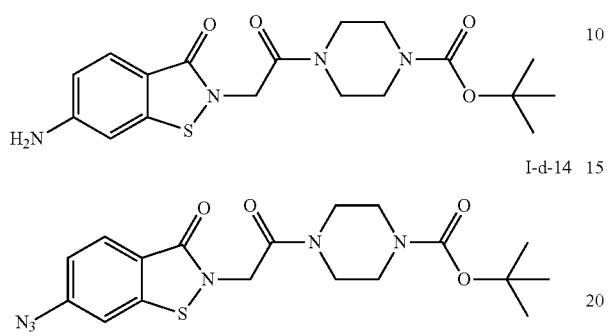

Under an atmosphere of Ar, a mixture of tert-butyl 4-(2-(6-bromo-3-oxobenzo[d]isothiazol-2(3H)-yl)acetyl)piperazine-1-carboxylate (I-d-10) (200 mg, 0.44 mmol), NaN$_3$ (57 mg, 0.88 mmol), CuI (33 mg, 0.18 mmol) and sodium ascorbate (17 mg, 0.09 mmol) in EtOH/H$_2$O (7:3, 4 mL) was stirred at room temperature. After addition of DMEDA (0.03 mL, 0.26 mmol), the temperature was elevated to 100° C. for 2 h, and then concentrated under reduced pressure. The residue was extracted with EtOAc and H$_2$O. The organic phase was dried over MgSO$_4$, filtered, concentrated, and separated by chromatography on a silica gel column with elution of EtOAc/hexane (1:1 to EtOAc) to give the azido compound I-d-14 (23 mg, 12% yield) along with the aniline compound I-d-13 (100 mg, 58% yield).

Aniline compound I-d-13 (316 mg, 0.81 mmol) and N-methyl-2-pyrrolidonium bisulfate (0.79 g, 4.00 mmol) was dissolved in H$_2$O (2 mL), and stirred for 10 min. To this solution was added sodium nitrite (0.18 g, 2.5 mmol) over a period of 3 min at 0° C. Upon completion of the addition, the mixture was stirred for an additional 15 min. Sodium azide (0.16 g, 2.5 mmol) was added over a period of 5 min. After 1 h, the solids were collected by filtration, rinsed with 10% HCl, and dried under reduced pressure to give the azido compound I-d-14 (15 mg; 45%).

Compound I-d-13: The purity of product I-d-13 was 95.2% as shown by HPLC on DIKMA column (Agilent, 4.6×250 mm, 5 m), $t_R$=14.2 min by elution of EtOAc at flow rate of 1.5 ml/min for 30 min. C$_{18}$H$_{24}$N$_4$O$_4$S; yellow solid; mp 178-180 OC; $^1$H NMR (400 MHz, CDCl$_3$) δ 7.73 (1H, d, J=8.4 Hz), 6.64 (2H, m), 4.60 (2H, s), 3.57-3.56 (2H, m), 3.52-3.49 (2H, m), 3.44-3.39 (4H, m), 1.44 (9H, s); $^{13}$C NMR (100 MHz, CDCl$_3$) δ 165.8, 165.7, 154.4, 150.7, 143.7, 127.9, 114.1 (2×), 103.1, 80.4, 45.2 (2×), 44.8, 42.0 (2×), 28.3 (3×); ESI-HRMS calcd for C$_{18}$H$_{24}$N$_4$O$_4$S: 393.1597. found: m/z 393.1597 [M+H]$^+$.

Compound I-d-14: The purity of product I-d-14 was 95.0% as shown by HPLC on DIKMA column (Agilent, 4.6×250 mm, 5 m), $t_R$=39.2 min with elution of EtOAc/hexane (1:1) at a flow rate of 1.5 ml/min for 48 min. C$_{18}$H$_{22}$N$_6$O$_4$S; yellow solid; mp 174-176° C.; IR ν$_{max}$ (neat) 2977, 2929, 2866, 2110, 1697, 1655, 1601, 1467, 1420, 1366, 1287, 1237, 1169, 1126, 1029, 996, 735, 671 cm$^{-1}$; $^1$H NMR (400 MHz, CDCl$_3$) δ7.99 (1H, d, J=8.4 Hz), 7.15 (1H, d, J=2.0 Hz), 7.05 (1H, dd, J=8.4, 2.0 Hz), 4.66 (2H, s), 3.60-3.58 (2H, m), 3.53-3.51 (2H, m), 3.45-3.42 (4H, m), 1.46 (9H, s); $^{13}$C NMR (100 MHz, CDCl$_3$) δ 165.2, 165.0, 154.4, 144.8, 143.3, 128.3, 120.2, 117.2, 110.0, 80.5, 45.1 (2×), 44.8, 42.0 (2×), 28.3 (3×); ESI-HRMS calcd for C$_{18}$H$_{23}$N$_6$O$_4$S: 419.1503. found: m/z 419.1502 [M+H]$^+$.

Tert-butyl 4-(2-(6-methoxy-3-oxobenzo[d]isothiazol-2(3H)-yl)acetyl)piperazine-1-carboxylate (I-d-15)

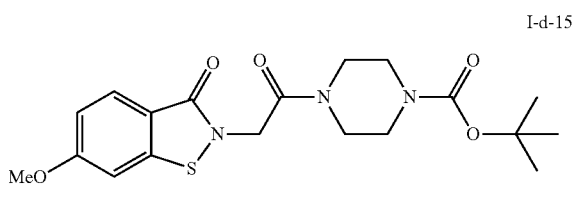 [SMILES: COc1ccc2c(=O)n(CC(=O)N3CCN(C(=O)OC(C)(C)C)CC3)sc2c1]

A mixture of 4-methoxy-2-nitrobenzonitrile (4.0 g, 1.39 mmol) and 10% Pd/C (0.4 g) was suspended in EtOH (40 mL) and stirred under an atmosphere of hydrogen for 18 h. The mixture was filtered over Celite, and the filtrate was concentrated under reduced pressure to give a crude product. After flash chromatography (silica gel, EtoAc/hexane=1:8 to 1:1), the product of 2-amino-4-methoxybenzonitrile was obtained (3.57 g, 95%). C$_8$H$_8$N$_2$O; yellow solid; mp: 75-76 OC; IR ν$_{max}$ (neat) 3481, 3379, 3105.3080, 3047, 2991, 2235, 2210, 1614, 1569, 1536, 1507, 1442, 1462, 1290, 1250, 1221, 1074, 1025, 899, 841, 808, 760, 682 cm$^{-1}$; $^1$H NMR (400 MHz, CDCl$_3$) δ 7.29 (1H, d, J=8.8 Hz), 6.31 (1H, dd, J=8.8 and 2.4 Hz), 6.19 (1H, d, J=2.4 Hz), 3.77 (3H, s); $^{13}$C NMR (100 MHz, CDCl$_3$) δ 164.2, 151.4, 133.8, 118.1, 105.8, 99.3, 88.7, 55.3; ESI-HRMS calcd for C$_8$H$_9$N$_2$O: 149.0715. found: m/z 149.0719 [M+H]$^+$.

The above-prepared aniline compound (1.0 g, 6.75 mmol) was dissolved in 8 M H$_2$SO$_{4(aq)}$ (15 mL), and NaNO$_2$ (0.7 g, 10.1 mmol) was added in portions at 0° C. The mixture was stirred for 15 min, and KS$_2$COOEt (0.7 g, 13.5 mmol) was added in portions. The mixture was stirred at room temperature for 2 h, and extracted with EtOAc. The organic layers was combined, concentrated, and purified by column chromatography (silica gel, EtOAc/hexane=1:4) to provide the product of S-(2-cyano-5-methoxyphenyl) O-ethyl carbonodithioate (1.71 g, 54% yield). C$_{11}$H$_{11}$NO$_2$S$_2$; yellow solid; mp: 87-88° C.; IR ν$_{max}$ 2983, 2942, 2897, 2844, 2222, 1597, 1556, 1495, 1442, 1368, 1307, 1238, 1144, 1111, 1058, 1029, 882, 820, 690 (neat) cm$^{-1}$; $^1$H NMR (400 MHz, CDCl$_3$) δ 7.71 (1H, d, J=8.8 Hz), 7.15 (1H, d, J=2.4 Hz), 7.03 (1H, dd, J=8.8 and 2.4 Hz), 4.65 (2H, q, J=7.2 Hz), 3.88 (3H, s), 1.37 (3H, t, J=7.2 Hz); $^{13}$C NMR (100 MHz, CDCl$_3$) δ 208.9, 162.7, 135.3, 135.1, 122.0, 117.1, 116.2, 110.9, 70.9, 55.9, 13.5; ESI-HRMS calcd for C$_{11}$H$_{12}$NO$_2$S$_2$: 254.0309. found: m/z 254.0312 [M+H]$^+$.

The above-prepared carbonodithioate (0.49 g, 1.9 mmol) was dissolved in MeOH (5 mL), and 3M NaOH (10 mL) was slowly added. The mixture was stirred at 90° C. for 2 h, and allowed to cool to room temperature. After acidification, the mixture was extracted with EtOAc and H$_2$O. The organic phase was dried over MgSO$_4$, filtered, and concentrated to give the product of 2-mercapto-4-methoxybenzonitrile (0.28 g, 87% yield). C$_8$H$_7$NOS; yellow solid; mp 134-136; IR ν$_{max}$ (neat) 3093, 3015, 2970, 2946, 2844, 2222, 2589, 1569, 1548, 1487, 1442, 1303, 1279, 1240, 1046, 1029, 825, 715, 690 cm$^{-1}$; $^1$H NMR (400 MHz, CDCl$_3$) δ 7.50 (1H, d, J=8.4 Hz), 6.87 (1H, d, J=2 Hz), 6.73 (1H, dd, J=8.8 and 2.8 Hz), 4.08 (1H, s), 3.82 (3H, s); $^{13}$C NMR (100 MHz, CDCl$_3$) δ 162.7, 139.1, 134.9, 117.8, 114.2, 112.3, 103.7, 55.7; ESI-HRMS (negative mode) calcd for C$_8$H$_6$NOS: 164.0170. found: m/z 164.0166 [M−H]$^-$.

A mixture of the above-prepared thiol compound (0.79 g, 4.78 mmol), benzyl bromide (0.82 g, 4.78 mmol), and K$_2$CO$_3$ (1.98 g, 14.33 mmol) in DMF (10 mL) was stirred at 25° C. for 14 h. After concentration, the residue was purified by silica gel column chromatography with elution of EtOAc/hexane (1:3) to give the product of 2-benzylthio-4-methoxybenzonitrile (1.15 g, 94%). C$_{15}$H$_{13}$NOS; yellow solid; mp 87-89; IR ν$_{max}$ (neat) 3072, 3032, 2979, 2939, 2839, 2217, 1591, 1552, 1478, 1480, 1456, 1439, 1301, 1275, 1238, 1053, 1028, 890, 832, 809, 768, 698 cm$^{-1}$; $^1$H NMR (400 MHz, CDCl$_3$) δ 7.52 (1H, d, J=8.4 Hz), 7.32 (5H, m), 6.78 (1H, d, J=2.8 Hz), 6.74 (1H, dd, J=8.4 and 2.8 Hz), 4.19 (2H, s), 3.73 (3H, s); $^{13}$C NMR (100 MHz, CDCl$_3$) δ 162.6, 142.6, 136.0, 135.1, 128.9 (2×), 128.6 (2×), 127.6, 117.5, 115.9, 112.6, 105.9, 55.6, 38.6.

A mixture of the above-prepared benzyl thioether (1.15 g, 4.5 mmol) and 37% HCl (3 mL) in CH$_2$Cl$_2$ (15 mL) was stirred in ice-bath under N$_2$ atmosphere, and SO$_2$Cl$_2$ (0.67 g, 4.95 mmol) was added. The mixture was stirred at 65-70° C. for 1 h, and then cooled to room temperature. The mixture was concentrated under reduced pressure, rinsed with H$_2$O, and purified by silica gel column chromatography with elution of EtOAc/hexane (1:1), EtOAc, and MeOH/CH$_2$Cl$_2$ (1:9) to give the product of 6-methoxybenzo[d]isothiazol-3(2H)-one (0.46 g, 58%). C$_8$H$_7$NO$_2$S; white solid; mp 196-198° C.; IR ν$_{max}$ (neat) 1655, 1596, 1573, 1485, 1433, 1264, 1252, 1235, 1218, 1048, 1012, 832, 674, 610, 552 cm$^{-1}$; $^1$H NMR (400 MHz, CDCl$_3$) δ 7.93 (1H, d, J=8.8 Hz), 7.00 (2H, m), 3.89 (3H, s); $^{13}$C NMR (100 MHz, CDCl$_3$) δ 168.0, 163.4, 143.4, 127.3, 115.4, 102.9, 55.8, 30.9; ESI-HRMS calcd for C$_8$H$_8$NO$_2$S: 182.0276. found: m/z 182.0282 [M+H]$^+$.

A mixture of the above-prepared isothiazolone compound (0.10 g, 0.55 mmol), tert-butyl 4-(2-iodoacetyl)piperazine-1-carboxylate (0.22, 0.61 mmol) and DIEA (0.2 mL, 1.1 mmol) in THF (3 mL) was stirred for 4 h at room temperature. The mixture was concentrated under reduced pressure. The residue was extracted with CH$_2$Cl$_2$ and H$_2$O. The organic phase was dried over MgSO$_4$, filtered, concentrated, and purified by flash chromatography on a silica gel column with elution of EtOAc/hexane (1:1, 2:1, 4:1 to 1:0) to give compound I-d-15 (0.18 g, 78% yield). The purity of product I-d-15 was 96.4% as shown by HPLC on DIKMA column (Agilent, 4.6×250 mm, 5 m), t$_R$=40.3 min with elution of EtOAc/hexane (7:3 to 1:0) at a flow rate of 1.0 mL/min for 50 min. C$_{19}$H$_{25}$N$_3$O$_5$S; white solid; mp 216-217° C.; IR ν$_{max}$ (neat) 2979, 2932, 2862, 1695, 1660, 1602, 1480, 1462, 1421, 1368, 1293, 1252, 1176, 1129, 1059, 1024, 1001, 768, 680 cm$^{-1}$; $^1$H NMR (400 MHz, CDCl$_3$) δ 7.90 (1H, d, J=9.2 Hz), 6.94 (2H, m), 4.65 (2H, s), 3.87 (3H, s), 3.59-3.57 (2H, m), 3.54-3.51 (2H, m), 3.42 (4H, s), 1.44 (s, 9H); $^{13}$C NMR (100 MHz, CDCl$_3$) δ 165.5, 165.4, 163.2, 154.4, 143.6, 127.9, 116.5, 114.8, 102.9, 80.4, 55.8, 45.2 (2×), 44.8, 42.0 (2×), 28.3 (3×); ESI-HRMS calcd for C$_{19}$H$_{26}$N$_3$O$_5$S: 408.1593. found: m/z 408.1585 [M+H]$^+$.

Tert-butyl 4-(2-(6-hydroxy-3-oxobenzo[d]isothiazol-2(3H)-yl)acetyl)piperazine-1-carboxylate (I-d-16)

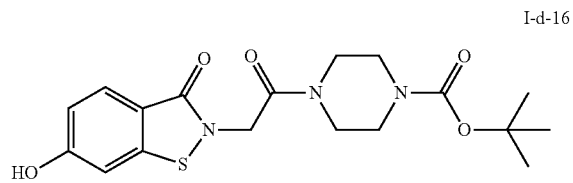 [SMILES: CC(C)(C)OC(=O)N1CCN(C(=O)Cn2sc3cc(O)ccc3c2=O)CC1]

Under an atmosphere of argon, BBr$_3$ in CH$_2$Cl$_2$ (2.76 mL of 1 M solution, 2.76 mmol) was added dropwise to the solution of 6-methoxybenzo[d]isothiazol-3(2H)-one (0.1 g, 0.55 mmol) in anhydrous CH$_2$Cl$_2$ (10 mL) at 0° C. The mixture was stirred at 25° C. for 17 h, and saturated NaHCO$_{3(aq)}$ was slowly added at 0° C. The mixture was extracted with CH$_2$Cl$_2$ and H$_2$O. The organic phase was dried over MgSO$_4$, filtered, concentrated, and purified by flash chromatography on a silica gel column with elution of EtOAc/hexane (1:1 to 1:0) to give 6-hydroxybenzo[d]isothiazol-3(2H)-one (0.09 g, 96% yield). C$_7$H$_5$NO$_2$S; white solid; $^1$H NMR (400 MHz, CD$_3$OD) δ 7.80 (1H, d, J=8.4 Hz), 7.08 (2H, d, J=1.6 Hz), 6.91 (1H, d, J=6.8, 1.6 Hz); ESI-HRMS (negative mode) calcd for C$_7$H$_4$NO$_2$S: 165.9963. found: m/z 165.9962 [M−H]$^-$.

A mixture of the above-prepared isothiazolone compound (0.11 g, 0.63 mmol), tert-butyl 4-(2-iodoacetyl)piperazine-1-carboxylate (0.22, 0.63 mmol) and DIEA (0.22 mL, 1.3 mmol) in THF (2 mL) was stirred for 3 h at room temperature. The mixture was concentrated under reduced pressure. The residue was extracted with EtOAc and H$_2$O. The organic phase was dried over MgSO$_4$, filtered, concentrated, and purified by flash chromatography on a silica gel column with elution of EtOAc/hexane (1:1, 2:1, and EtOAc) to give compound I-d-16 (0.15 g, 62% yield). The purity of product I-d-16 was 96.2% as shown by HPLC on DIKMA column (Agilent, 4.6×250 mm, 5 m), t$_R$=10.9 min with elution of EtOAc at a flow rate of 1.0 mL/min for 30 min. C$_{18}$H$_{23}$N$_3$O$_5$S; white solid; mp 201-203° C.; IR ν$_{max}$ (neat) 3467, 2976, 2929, 2868, 2691, 1689, 1658, 1608, 1568, 1473, 1046, 1422, 1366, 1287, 1237, 1167, 1130, 1030, 995, 904, 861, 763, 733, 679 cm$^{-1}$; $^1$H NMR (400 MHz, CDCl$_3$) δ 7.72 (1H, d, J=8.8 Hz), 6.83 (1H, d, J=2 Hz), 6.79 (1H, dd, J=8.8, 2.0 Hz), 4.63 (2H, s), 3.59-3.57 (2H, m), 3.51-3.50 (2H, m), 3.46-3.40 (4H, m), 1.44 (9H, s); $^{13}$C NMR (100 MHz, CDCl$_3$) δ 165.9, 165.6, 160.4, 154.4, 143.1, 128.1, 116.0, 115.5, 105.7, 80.7, 45.2 (2×), 44.7, 42.2 (2×), 28.4 (3×); ESI-HRMS calcd for C$_{18}$H$_{24}$N$_3$O$_5$S: 394.1437. found: m/z 394.1418 [M+H]$^+$.

Tert-butyl 4-(2-(6-((tert-butyldimethylsilyl)oxy)-3-oxobenzo[d]isothiazol-2(3H)-yl)-acetyl)piperazine-1-carboxylate (I-d-17)

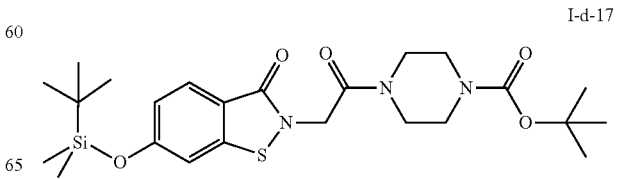

A mixture of tert-butyl 4-(2-(6-hydroxy-3-oxobenzo[d]isothiazol-2(3H)-yl)acetyl)piperazine-1-carboxylate (I-d-16) (42 mg; 0.09 mmol), 1H-imidazole (50 mg, 0.73 mg), and 4-DMAP (6 mg, 0.05 mmol) in $CH_2Cl_2$ (1 mL) was stirred at 0° C., and tert-butyldimethylsilyl chloride (TBDMSCl) (78 mg, 0.52 mmol) was added. The mixture was stirred at room temperature for 11 h, and then concentrated under reduced pressure. The residue was extracted with $CH_2Cl_2$ and $H_2O$. The organic phase was concentrated, and separated by chromatography on a silica gel column with elution of EtOAc/hexane (1:1) to give the compound I-d-17 (15 mg, 32% yield). The purity of product I-d-17 was 98.2% as shown by HPLC on DIKMA column (Agilent, 4.6×250 mm, 5 m), $t_R$=28.6 min with elution of EtOAc/hexane (1:1) at a flow rate of 1.0 mL/min for 40 min. $C_{24}H_{37}N_3O_5SSi$; white solid; mp 137.0-138.4° C.; IR $v_{max}$ (neat) 2962, 2929, 2858, 1701, 1656, 1598, 1473, 1417, 1365, 1267, 1240, 1170, 1125, 1051, 1028, 996, 942, 830, 784, 678 $cm^{-1}$; $^1H$ NMR (400 MHz, $CDCl_3$) δ 7.87 (1H, d, J=8.8 Hz), 6.92 (1H, d, J=2 Hz), 6.86 (1H, dd, J=8.4, 2.0 Hz), 4.64 (2H, s), 3.60-3.57 (2H, m), 3.54-3.51 (2H, m), 3.42-3.41 (4H, m), 1.45 (9H, s), 0.97 (9H, s), 0.22 (6H, s); $^{13}C$ NMR (100 MHz, $CDCl_3$) δ 165.7 (2×), 159.9, 154.6, 143.3, 128.2, 119.6, 117.3, 110.6, 80.7, 45.4 (2×), 45.0, 42.2 (2×), 28.5 (3×), 25.7 (3×), 18.4, −4.2 (2×); ESI-HRMS calcd for $C_{24}H_{38}N_4O_{5S}Si$: 508.2301. found: m/z 508.2302 [M+H]$^+$.

Tert-butyl 4-(2-(6-(4-octyl-1H-1,2,3-triazol-1-yl)-3-oxobenzo[d]isothiazol-2(3H)-yl)acetyl)piperazine-1-carboxylate (I-d-18)

I-d-18

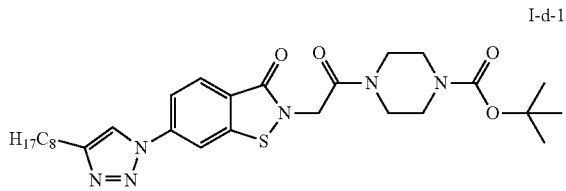

Under an atmosphere of Ar, 1-decyne (17 mg, 0.120 mmol) was added to a mixture of tert-butyl 4-(2-(6-azido-3-oxobenzo[d]isothiazol-2(3H)-yl)acetyl)piperazine-1-carboxylate (I-d-14) (50 mg, 0.120 mmol), copper sulfate (6 mg, 0.024 mmol), and sodium ascorbate (10 mg, 0.048 mmol) in $H_2O$/t-BuOH (1:1, 1 mL) at room temperature. The mixture was stirred for 19 h, and then filtered through a pad of Celite. The filtrate was concentrated under reduced pressure, and purified by flash chromatography on a silica gel column with elution of EtOAc/hexane (0:1 to 1:0) to give compound I-d-18 (46 mg, 70% yield). $C_{28}H_{40}N_6O_4S$; white solid, mp 193-194° C.; IR $v_{max}$ (neat) 3440, 3351, 3233, 3005, 2978, 2929, 2865, 1695, 1660, 1602, 1450, 1421, 1369, 1287, 1240, 1170, 1030, 995, 861, 838, 756 $cm^{-1}$; $^1H$ NMR (400 MHz, $CDCl_3$) δ 8.15 (1H, dd, J 8.4 Hz), 8.03 (1H, s), 7.79 (1H, s), 7.71 (1H, d, J 8.4 Hz), 4.71 (2H, s), 3.61 (2H, m), 3.54 (2H, m), 3.49 (4H, m), 2.81 (2H, t, J 7.2 Hz), 1.74 (2H, t, J 6.4 Hz), 1.45 (9H, s), 1.39 (2H, m), 1.25 (8H, m), 0.88 (3H, t, J 6.4 Hz); $^{13}C$ NMR (100 MHz, $CDCl_3$) δ 165.0, 164.9, 154.4, 149.9, 143.2, 140.0, 128.3, 122.8, 118.8, 117.5, 111.7, 80.6, 45.1 (2×), 44.9, 42.0 (2×), 31.8, 29.3 (4×), 28.3 (3×) 25.6, 22.6, 14.1; ESI-HRMS calcd for $C_{28}H_{41}N_6O_4S$: 557.2910. found: m/z 557.2903 [M+H]$^+$.

Tert-butyl 4-(2-(6-(4-(4-fluorophenyl)-1H-1,2,3-triazol-1-yl)-3-oxobenzo[d]isothiazol-2(3H)-yl)acetyl)piperazine-1-carboxylate (I-d-19)

I-d-19

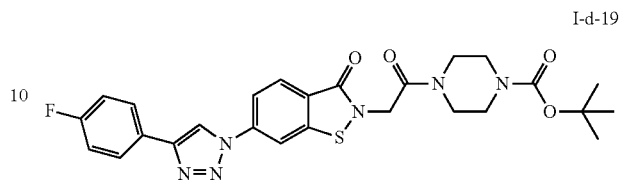

Under an atmosphere of Ar, 1-ethynyl-4-fluorobenzene (29 mg, 0.239 mmol) was added to a mixture of tert-butyl 4-(2-(6-azido-3-oxobenzo[d]isothiazol-2(3H)-yl)acetyl)piperazine-1-carboxylate (I-d-14) (100 mg, 0.239 mmol), copper sulfate (12 mg, 0.048 mmol) and sodium ascorbate (19 mg, 0.096 mmol) in $H_2O$/t-BuOH (1:1, 1.5 mL) at room temperature. The mixture was stirred for 19 h, and filtered through a pad of Celite. The filtrate was concentrated under reduced pressure, and subjected to flash chromatography on a silica gel column with elution of EtOAc/hexane (1:1 to 3:1) to give compound I-d-18 (66 mg, 51% yield). $C_{26}H_{27}FN_6O_4S$; white solid, mp 235-237° C.; IR $v_{max}$ (neat) 2921, 2852, 1687, 1642, 1434, 1230, 1172, 1127, 1037, 841, 816, 760 $cm^{-1}$; $^1H$ NMR (400 MHz, $CDCl_3$) δ 8.26 (1H, s), 8.21 (1H, d, J=8.4 Hz), 8.12 (1H, d, J=2 Hz), 7.91 (2H, m), 7.80 (1H, dd, J=8.4 Hz), 7.20 (2H, m), 4.73 (2H, s), 3.62 (2H, m), 3.55 (2H, m), 3.50 (2H, m), 3.46 (2H, m), 1.46 (9H, s); $^{13}C$ NMR (100 MHz, $CDCl_3$) δ 165.0, 164.8, 163.0 (d, $^1J_{CF}$=247.3 Hz), 154.4, 148.1, 143.3, 139.7, 128.5, 127.7 (2×, d, $^1J_{CF}$=8.3 Hz), 126.0, 123.2, 117.6, 117.3, 116.1 (2×, $^1J_{CF}$=21.2 Hz), 111.9, 80.6, 45.1 (2×), 44.9, 42.1 (2×), 28.3 (3×); ESI-HRMS calcd for $C_{26}H_{28}FN_6O_4S$, 539.1877. found: m/z 539.1885 [M+H]$^+$.

2-[2-(4-(2-Iodoacetyl)piperazin-1-yl)-2-oxoethyl]benzo[d]isothiazol-3(2H)-one (I-e-1)

I-e-1

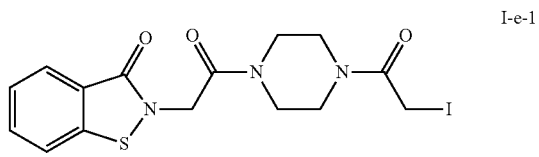 [SMILES: O=C(CI)N1CCN(C(=O)Cn2sc3ccccc3c2=O)CC1]

A solution of benzo[d]isothiazol-3(2H)-one (45 mg, 0.30 mmol) in anhydrous $CH_2Cl_2$ (2.7 mL) was added via syringe pump over a period of 2 h to a suspension of 1,4-bis(iodoacetyl)piperazine (241 mg, 0.57 mmol) and DIEA (0.28 mL, 1.58 mmol) in anhydrous $CH_2Cl_2$ (0.8 mL) at room temperature. The mixture was washed with 1 M $HCl_{(aq)}$, and extracted with $CH_2Cl_2$ and $H_2O$. The organic phase was dried over $MgSO_4$, filtered, and concentrated under reduced pressure. The residual were then washed with MeOH and recrystallized from $CH_2Cl_2$ to give compound I-e-1 (41 mg, 30% yield). $C_{15}H_{16}IN_3O_3S$; pale yellow solid; mp 210-212° C.; TLC (EtOAc/hexane=8:1) $R_f$=0.2; IR $v_{max}$ (neat) 2923, 2858, 1641, 1446, 1342, 1285, 1243, 1020, 985, 743, 673 $cm^{-1}$; $^1H$ NMR (400 MHz, $CDCl_3$) δ 8.02 (1H, d, J=7.2 Hz), 7.62 (1H, t, J=7.2 Hz), 7.54-7.56 (1H, m), 7.40 (1H, t, J=7.4 Hz), 4.71 (2H, s), 3.74 (4H, s), 3.60-3.65 (4H, m), 3.46-3.49 (2H, m); $^{13}$C NMR (100 MHz, CDCl$_3$) δ 166.6, 165.2, 141.1, 132.2, 126.8, 125.5, 123.2, 120.3, 47.0, 46.7, 44.8, 41.9, 41.7, −4.4; ESI-HRMS calcd for C$_{15}$H$_{17}$N$_3$O$_3$S: 446.0035. found: m/z 446.0033 [M+H]$^+$.

Tert-butyl (2-oxo-2-(4-(2-(3-oxobenzo[d]isothiazol-2(3H)-yl)acetyl)piperazin-1-yl)ethyl)carbamate (I-e-2)

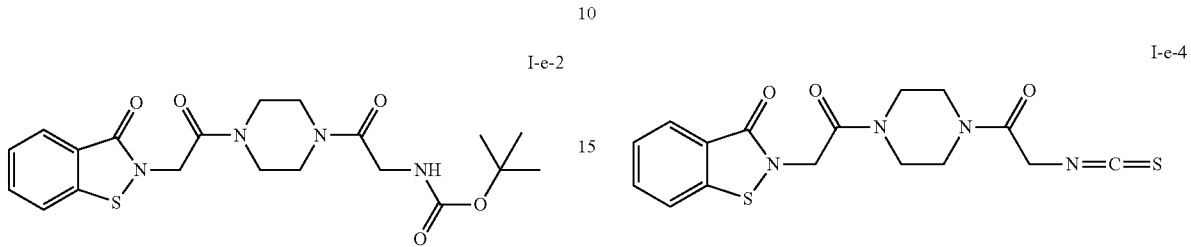

Boc-glycine (223.2 mg, 1.27 mmol), EDC (181 mg, 1.17 mmol), DIEA (0.57 mL, 3.27 mmol), DMAP (39 mg, 0.32 mmol) were added to a solution of 2-(2-oxo-2-(piperazin-1-yl)ethyl)benzo[d]isothiazol-3(2H)-one (I-f-1) (295 mg, 1.06 mmol) in CH$_2$Cl$_2$ (30 mL) at room temperature. The mixture was stirred for 14 h, and then extracted with 1 M HCl$_{(aq)}$ and saturated NaHCO$_{3(aq)}$. The combined organic phase was washed with brine, dried over MgSO$_4$, filtered, and concentrated under reduced pressure to provide compound I-e-2 (265 mg, 58% yield) after flash column chromatography (silica gel, CH$_2$Cl$_2$/MeOH (95:5)). C$_{20}$H$_{26}$N$_4$O$_5$S; white solid (hygroscopic); IR ν$_{max}$ (neat) 3427, 3323, 2986, 2939, 1708, 1654, 1468, 1447, 1251, 1223, 1167 cm$^{-1}$; $^1$H NMR (400 MHz, CDCl$_3$) δ 8.01 (1H, dd, J=7.6, 0.6 Hz), 7.61 (1H, t, J=7.6 Hz), 7.54 (1H, d, J=7.6 Hz), 7.39 (1H, t, J=7.6 Hz), 5.42 (1H, br s), 4.69 (2H, s), 3.94 (2H, br s), 3.63-3.59 (6H, m), 3.41-3.40 (2H, m), 1.42 (9H, s); $^{13}$C NMR (100 MHz, CDCl$_3$) δ 167.2, 165.5, 165.1, 155.6, 141.0, 132.0, 126.4, 125.4, 123.0, 120.2, 79.5, 44.5, 43.9, 43.7, 42.0, 41.5, 41.4, 28.1 (3×); ESI-HRMS calcd for C$_{20}$H$_{26}$N$_4$O$_5$NaS: 457.1522. found m/z 457.1510 [M+Na]$^+$.

2-(2-(4-(2-Aminoacetyl)piperazin-1-yl)-2-oxoethyl)benzo[d]isothiazol-3(2H)-one (I-e-3)

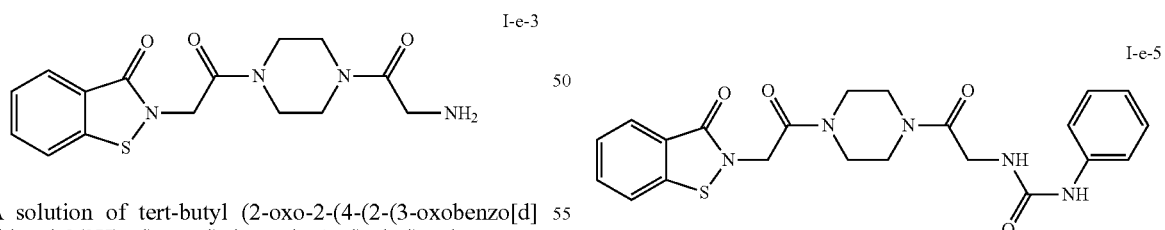

A solution of tert-butyl (2-oxo-2-(4-(2-(3-oxobenzo[d]isothiazol-2(3H)-yl)acetyl)piperazin-1-yl)ethyl)carbamate (I-e-2) (150 mg, 0.35 mmol) and TFA (5.29 mL, 69 mmol) in CH$_2$Cl$_2$ (9.8 mL) was stirred at room temperature for 1 h. TFA was removed under reduced pressure; the residue was extracted with CHCl$_3$ and ammonia solution (35%). The combined organic phase was dried over MgSO$_4$, filtered, and concentrated under reduced pressure to provide the product I-e-3 (109 mg, 94% yield). C$_{15}$H$_{18}$N$_4$O$_3$S; yellow solid (hygroscopic); IR ν$_{max}$ (neat) 3373, 2963, 2933, 2854, 1664, 1658, 1643, 1633, 1467, 1446, 1230, 1027, 794, 745 cm$^{-1}$; $^1$H NMR (400 MHz, CDCl$_3$) δ 8.02 (1H, d, J=7.5 Hz), 7.62 (1H, t, J=7.5 Hz), 7.55 (1H, d, J=7.5 Hz), 7.39 (1H, t, J=7.5 Hz), 4.70 (2H, s), 3.63-3.60 (7H, m), 3.45-3.39 (5H, m); $^{13}$C NMR (100 MHz, CDCl$_3$) δ 165.1 (2×), 165.0, 141.4, 132.0, 125.6, 125.3, 123.4, 121.7, 48.6, 44.5, 43.8 (2×), 41.3 (2×); ESI-HRMS calcd for C$_{15}$H$_{19}$N$_4$O$_3$S: 335.1178. found m/z 335.1174 [M+H]$^+$.

2-(2-(4-(2-Isothiocyanatoacetyl)piperazin-1-yl)-2-oxoethyl)benzo[d]isothiazol-3(2H)-one (I-e-4)

A solution of dithiocarbonyl imidazole (15 mg, 0.084 mmol) in anhydrous DMF (0.2 mL) was slowly added to the solution of 2-(2-(4-(2-aminoacetyl)piperazin-1-yl)-2-oxoethyl)benzo[d]isothiazol-3(2H)-one (I-e-3) (27 mg, 0.081 mmol) in anhydrous DMF (0.2 mL) under Ar atmosphere. The mixture was stirred at room temperature for 17 h, and DMF was washed off with CHCl$_3$/H$_2$O (1:10). The combined organic phase was dried over MgSO$_4$, filtered and concentrated under reduced pressure. After flash column chromatography (silica gel, hexane/EtOAc (1:1 to 1:0)), the isothiocyanate compound I-e-4 was obtained (15 mg, 47% yield). The purity of product I-e-4 was 99% as shown by HPLC on an HC-C18 column (Merck, 4.6×100 mm, 5 m porosity), t$_R$=1.6 min (MeOH, flow rate=1 mL/min). C$_{16}$H$_{16}$N$_4$O$_3$S$_2$; white solid, 198° C. (decomposed); IR ν$_{max}$ (neat) 2921, 2850, 2093, 1656, 1471, 1446, 1426, 1249, 1224, 1020 cm$^{-1}$; $^1$H NMR (400 MHz, CDCl$_3$) δ 8.02 (1H, d, J=7.9 Hz), 7.63 (1H, t, J=7.9 Hz), 7.55 (1H, d, J=7.9 Hz), 7.40 (1H, t, J=7.9 Hz), 4.70 (2H, s), 4.28 (2H, s), 3.68-3.65 (6H, m), 3.37 (2H, br s); $^{13}$C NMR (100 MHz, CDCl$_3$) δ 165.1, 164.9, 163.5, 141.4, 133.8, 131.9, 125.6, 125.3, 123.4, 121.7, 47.5, 44.5, 43.7, 41.9, 41.1, 40.1; ESI-HRMS calcd for C$_{16}$H$_{16}$N$_4$O$_3$NaS$_2$: 399.0562. found m/z 399.0578 [M+Na]$^+$.

1-(2-Oxo-2-(4-(2-(3-oxobenzo[d]isothiazol-2(3H)-yl)acetyl)piperazin-1-yl)ethyl)-3-phenylurea (I-e-5)

Et$_3$N (1.1 mL, 7.88 mmol) was added to a solution of glycine methyl ester hydrochloride (1.00 g, 7.96 mmol) in anhydrous CH$_2$Cl$_2$ (37 mL) at 0° C. The mixture was stirred at room temperature for 15 min to neutralization. Phenyl isocyanate (1.15 g, 6.64 mmol) was added dropwise into the solution. The mixture was stirred at room temperature under Ar atmosphere for 22 h, and then washed with 1 M HCl (aq) and brine. The urea product, methyl 2-(3-phenylureido)acetate (560 mg, 34%), was obtained by flash column chromatography (silica gel, hexane/EtOAc (1:1)).

$C_{10}H_{12}N_2O_3$; white solid, mp 134-135° C.; $^1H$ NMR (400 MHz, $CDCl_3$) δ 8.79 (1H, s), 7.39 (2H, d, J=7.9 Hz), 7.22 (2H, t, J=7.9 Hz), 6.90 (1H, td, J=7.9, 1.2 Hz), 6.45 (1H, t, J=5.7 Hz), 3.88 (2H, d, J=5.7 Hz), 3.65 (3H, s); $^{13}C$ NMR (100 MHz, $CDCl_3$) δ 171.4, 155.2, 140.2, 128.7 (2×), 121.3, 117.7 (2×), 51.6, 41.3; ESI-HRMS calcd for $C_{10}H_{13}N_2O_3$: 209.0926. found m/z 209.0927 [M+H]$^+$.

The above-prepared ester compound (60 mg, 0.29 mmol) was dissolved in MeOH (2 mL), and 1 M $NaOH_{(aq)}$ was added into the solution at room temperature. The mixture was stirred for 90 min, adjusted to pH=6-7 by adding Dowex resin. After filtration and concentration, the saponification product, 2-(3-phenylureido)acetic acid (50 mg, 87%), was obtained. $C_9H_{10}N_2O_3$; white solid, mp 195-196° C.; IR ν$_{max}$ (neat) 3351, 2925, 1651, 1630, 1596, 1584, 1551, 1441, 1246, 1230 cm$^{-1}$; $^1H$ NMR (400 MHz, DMSO-d$_6$) δ 12.58 (1H, br), 8.76 (1H, s), 7.38 (2H, d, J=7.8 Hz), 7.22 (2H, t, J=7.8 Hz), 6.89 (1H, t, J=7.8 Hz), 6.35 (1H, t, J=5.8 Hz), 3.79 (2H, d, J=5.8 Hz); $^{13}C$ NMR (100 MHz, DMSO-d$_6$) δ 172.2, 155.2, 140.3, 128.7 (2×), 121.2, 117.6 (2×), 41.3; ESI-HRMS (negative mode) calcd for $C_9H_9N_2O_3$: 193.0613. found m/z 193.0612 [M−H]$^-$.

To a solution of the above-prepared carboxylic acid compound (47 mg, 0.24 mmol) in DMF (5.6 mL) were added 2-(2-oxo-2-(piperazin-1-yl)ethyl)benzo[d]isothiazol-3(2H)-one (I-f-1) (55 mg, 0.20 mmol), EDC (34 mg, 0.22 mmol), DMAP (7 mg, 0.06 mmol) and DIEA (0.1 mL, 0.60 mmol) at room temperature. The mixture was stirred for 16 h, and then concentrated under reduced pressure. The residue was extracted with $CHCl_3$ and 1 M $HCl_{(aq)}$ and saturated $NaHCO_{3(aq)}$. The combined organic phase was washed with brine, dried over $MgSO_4$ and concentrated under removed pressure. After flash column chromatography (silica gel, $CH_2Cl_2$/MeOH=95:5), the product I-e-5 (50 mg, 56% yield) was obtained. The purity of product I-e-5 was 95% as shown by HPLC on an HC-C18 column (Merck, 4.6×100 mm, 5 μm porosity), t$_R$=2.5 min (MeOH/H$_2$O=1:1, flow rate=1 mL/min). $C_{22}H_{23}N_5O_4$; white solid, mp 194-195° C.; IR ν$_{max}$ (neat) 3355, 2921, 2860, 1671, 1644, 1597, 1555, 1446, 1226 cm$^{-1}$; $^1H$ NMR (400 MHz, $CDCl_3$) δ 8.90 (1H, br s), 7.96 (1H, d, J=8.0 Hz), 7.88 (1H, d, J=8.0 Hz), 7.70 (1H, t, J=8.0 Hz), 7.44 (1H, t, J=8.0 Hz), 6.89 (1H, t, J=7.6 Hz), 6.50 (1H, br s), 4.80 (2H, s), 4.04 (2H, s); $^{13}C$ NMR (100 MHz, $CDCl_3$) δ 167.9, 165.2, 165.1, 155.1, 141.5, 140.4, 132.0, 128.7 (2×), 125.7, 125.4, 123.5, 121.7, 121.2, 117.6 (2×), 44.5, 44.0, 43.8, 43.5, 41.3, 41.1; ESI-HRMS calcd for $C_{22}H_{23}N_5O_4NaS$: 476.1368. found m/z 476.1382 [M+Na]$^+$.

1-(4-Methoxyphenyl)-3-(2-oxo-2-(4-(2-(3-oxobenzo[d]isothiazol-2(3H)-yl)acetyl)piperazin-1-yl)ethyl)urea (I-e-6)

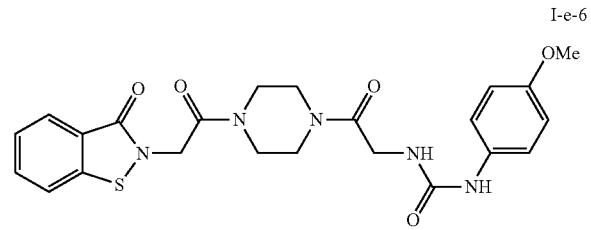 [SMILES: COc1ccc(NC(=O)NCC(=O)N2CCN(C(=O)Cn3sc4ccccc4c3=O)CC2)cc1]

I-e-6

Et$_3$N (0.33 mL, 2.36 mmol) was added to a solution of glycine methyl ester hydrochloride (300 mg, 2.39 mmol) in anhydrous $CH_2Cl_2$ (13 mL) at 0° C., the mixture was stirred at room temperature for 15 min to neutralization. 4-Methoxyphenyl isocyanate (297 mg, 1.99 mmol) was added dropwise into the solution. The mixture was stirred at room temperature under Ar atmosphere for 24 h, and then washed with 1 M $HCl_{(aq)}$ and brine. The urea product, methyl 2-[3-(4-methoxyphenyl)ureido]acetate (432 mg, 91%), was obtained by flash column chromatography (silica gel, hexane/EtOAc (1:1)). $C_{11}H_{14}N_2O_4$; white solid, mp 130-131° C.; IR ν$_{max}$ (neat) cm$^{-1}$; $^1H$ NMR (400 MHz, CDCl3) δ 7.20 (2H, d, J=8.8 Hz), 6.83 (2H, d, J=8.8 Hz), 6.70 (br s, 1H), 5.39 (br s, 1H), 4.01 (2H, d, J=5.6 Hz), 3.76 (s, 3H), 3.71 (s, 3H); $^{13}C$ NMR (100 MHz, $CDCl_3$) δ 171.7, 156.7, 156.4, 131.0, 123.6 (2×), 114.3 (2×), 55.4, 52.2, 41.8; ESI-HRMS calcd for $C_{11}H_{15}N_2O_4$: 239.1032. found m/z 239.1035 [M+H]$^+$.

The above-prepared ester compound (150 mg, 0.63 mmol) was dissolved in MeOH (4.5 mL), and 1 M $NaOH_{(aq)}$ (4.5 mL) was added. The mixture was stirred at room temperature for 2 h, and adjusted to pH=6-7 by adding Dowex resin. After filtration and concentration, the saponification product, 2-[3-(4-methoxyphenyl)ureido]acetic acid (94 mg, 100%), was obtained. $C_{10}H_{12}N_2O_4$; white solid; mp 194-196° C.; $^1H$ NMR (400 MHz, DMSO-d$_6$) δ 12.53 (1H, br s), 8.55 (1H, br s), 7.28 (2H, d, J=9.0 Hz), 6.81 (2H, d, J=9.0 Hz), 6.24 (1H, t, J=5.6 Hz), 3.77 (2H, d, J=5.6 Hz), 3.69 (3H, s); $^{13}C$ NMR (100 MHz, DMSO-d$_6$) δ 172.4, 155.5, 154.1, 144.5, 119.5 (2×), 114.0 (2×), 55.2; ESI-HRMS calcd for $C_{10}H_{11}N_2O_4$: 223.0719. found m/z 223.0732 [M−H]$^-$.

To a solution of the above-prepared carboxylic acid compound (39 mg, 0.16 mmol) in DMF (4.1 mL) were added 2-(2-oxo-2-(piperazin-1-yl)ethyl)benzo[d]isothiazol-3(2H)-one (I-f-1) (40 mg, 0.14 mmol), EDC (25 mg, 0.16 mmol), DMAP (5 mg, 0.04 mmol) and DIEA (0.075 mL, 0.43 mmol) at room temperature. The mixture was stirred for 21 h, and then concentrated under reduced pressure. The residue was extracted with $CH_2Cl_2$ and 1 M $HCl_{(aq)}$ and saturated $NaHCO_{3(aq)}$. The combined organic phase was washed with brine, dried over $MgSO_4$ and concentrated under reduced pressure. After flash column chromatography (silica gel, $CH_2Cl_2$/MeOH=98:2), the product I-e-6 (16 mg, 23% yield) was obtained. The purity of product I-e-6 was 96% as shown by HPLC on an HC-C18 column (Merck, 4.6×100 mm, 5 m porosity), t$_R$=5.13 min (MeOH/H$_2$O=1:3, flow rate=1 mL/min). $C_{23}H_{25}N_5O_5S$; white solid, mp 200-202° C.; IR ν$_{max}$ (neat) 3361, 1665, 1648, 1604, 1562, 1510, 1462, 1440 cm$^{-1}$; $^1H$ NMR (400 MHz, DMSO-d$_6$) δ 8.69 (1H, br s), 7.97 (1H, dd, J=7.7, 1.0 Hz), 7.88 (1H, dd, J=7.7, 1.0 Hz), 7.70 (1H, td, J=7.7, 1.0 Hz), 7.44 (1H, td, J=7.7, 1.0 Hz), 7.29 (2H, d, J=9.2 Hz), 6.81 (1H, d, J=9.2 Hz), 6.23 (1H, br s), 4.81 (2H, s), 4.02 (2H, m), 3.69 (3H, s), 3.58 (2H, br s), 3.53-3.45 (6H, m); $^{13}C$ NMR (100 MHz, $CD_3OD$) δ 167.9, 165.1, 165.0, 155.3, 153.9, 141.4, 133.6, 132.0, 125.6, 125.3, 123.5, 121.7, 119.2 (2×), 113.8 (2×), 55.1, 44.5, 43.7 (2×), 41.2 (2×), 41.0; ESI-HRMS calcd for $C_{23}H_{26}N_5O_5S$: 484.1655. found m/z 484.1656 [M+H]$^+$.

Butyl-3-(2-oxo-2-(4-(2-(3-oxobenzo[d]isothiazol-2(3H)-yl)acetyl)piperazin-1-yl)ethyl)urea (I-e-7)

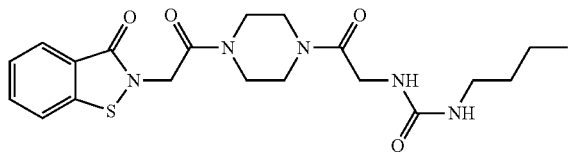

I-e-7

Et$_3$N (0.33 mL, 2.36 mmol) was added to a solution of glycine methyl ester hydrochloride (300 mg, 2.39 mmol) in anhydrous CH$_2$Cl$_2$ (13 mL) at 0° C. The mixture was stirred at room temperature for 15 min to neutralization. n-Butyl isocyanate (197 mg, 1.99 mmol) was added dropwise into the solution. The mixture was stirred at room temperature under Ar atmosphere for 24 h, and then washed with 1 M HCl$_{(aq)}$ and brine. The urea product, methyl 2-(3-butylureido)acetate (183 mg, 50%), was obtained after flash column chromatography (silica gel, hexane/EtOAc (1:1)). C$_8$H$_{16}$N$_2$O$_3$; white solid; mp 68-69° C.; IR $\nu_{max}$ (neat) cm$^{-1}$; $^1$H NMR (400 MHz, CDCl$_3$) δ 5.63 (br s, 1H), 5.35 (br s, 1H), 3.92 (2H, d, J=5.2 Hz), 3.68 (s, 3H), 3.10 (2H, td, J=7.2, 5.6 Hz), 1.44-1.38 (2H, m), 1.35-1.23 (2H, m), 0.86 (3H, t, J=7.2 Hz); $^{13}$C NMR (100 MHz, CDCl$_3$) 171.8, 158.9, 51.7, 41.7, 39.8, 32.1, 19.8, 13.5; ESI-HRMS calcd for C$_8$H$_{17}$N$_2$O$_3$: 189.1239. found m/z 189.1240 [M+H]$^+$.

The above-prepared methyl ester (60 mg, 0.32 mmol) was dissolved in MeOH (2.3 mL), and 1 M NaOH$_{(aq)}$ (2.3 mL) was added into the solution at room temperature. The mixture was stirred for 5 h, and adjusted to pH=6-7 by adding Dowex resin. After filtration and concentration, 2-(3-butylureido)acetic acid (56 mg, 100%) was obtained. C$_7$H$_{14}$N$_2$O$_3$; white solid; mp 87-88° C.; $^1$H NMR (400 MHz, CD$_3$OD) δ 3.85 (2H, s), 3.12 (2H, t, J=7.0 Hz), 1.46 (2H, m), 1.36 (2H, m), 0.93 (3H, J=7.4 Hz); $^{13}$C NMR (100 MHz, CD$_3$OD) δ 174.6, 161.2, 42.7, 40.9, 33.5, 21.1, 14.3; ESI-HRMS calcd for C$_7$H$_{13}$N$_2$O$_3$: 173.0926. found m/z 173.0938 [M−H]$^−$.

To a solution of the above-prepared carboxylic acid (30 mg, 0.17 mmol) in DMF (4.1 mL) were added 2-(2-oxo-2-(piperazin-1-yl)ethyl)benzo[d]isothiazol-3(2H)-one (I-f-1) (40 mg, 0.14 mmol), EDC (27 mg, 0.17 mmol), DMAP (5 mg, 0.04 mmol) and DIEA (0.075 mL, 0.43 mmol) at room temperature. The mixture was stirred for 21 h, and then concentrated under reduced pressure. The residue was extracted with CH$_2$Cl$_2$ and 1 M HCl (aq) and saturated NaHCO$_{3(aq)}$. The combined organic phase was washed with brine, dried over MgSO$_4$ and concentrated under reduced pressure. After flash column chromatography (silica gel, CH$_2$Cl$_2$/MeOH=98:2), the product I-e-7 (17 mg, 27% yield) was obtained. The purity of product I-e-7 was 92% as shown by HPLC on an HC-C18 column (Merck, 4.6×100 mm, 5 m porosity), t$_R$=2.10 min (MeOH/H$_2$O=1:1, flow rate=1 mL/min). C$_{20}$H$_{27}$N$_5$O$_4$S; white solid, mp 172-173° C.; IR $\nu_{max}$ (neat) 3366, 3269, 2958, 2927, 2864, 1709, 1647, 1445, 1339, 1228 cm$^{-1}$; $^1$H NMR (400 MHz, DMSO-d$_6$) δ 7.97 (1H, d, J=7.8 Hz), 7.88 (1H, d, J=7.8 Hz), 7.70 (1H, t, J=7.8 Hz), 7.44 (1H, t, J=7.8 Hz), 6.26 (1H, t, J=5.4 Hz), 5.95 (1H, br s), 4.80 (2H, s), 4.04 (2H, br s), 3.55-3.46 (8H, m), 2.98 (2H, q, J=4.6 Hz), 1.35-1.24 (4H, m), 0.87 (3H, t, J=7.0 Hz); $^{13}$C NMR (100 MHz, CD$_3$OD) δ 168.3, 165.1, 164.9, 157.9, 141.4, 131.9, 125.6, 125.3, 123.4, 121.7, 44.4, 43.7 (4×), 40.1, 32.1, 19.5, 13.7; ESI-HRMS calcd for C$_{20}$H$_{28}$N$_5$O$_4$S: 434.1862. found m/z 434.1859 [M+H]$^+$.

1,4-Bis[(3-oxo-benzo[d]isothiazol-2-yl)acetyl]piperazine (I-e-8)

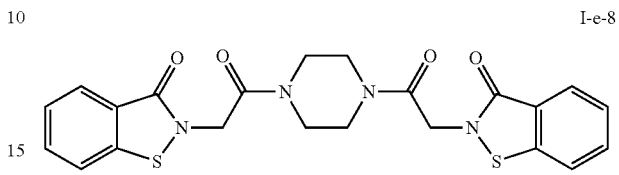

I-e-8

A mixture of benzo[d]isothiazol-3(2H)-one (63 mg, 0.46 mmol), 1,4-bis(iodoacetyl)piperazine (80 mg, 0.19 mmol) and DIEA (0.16 mL, 0.95 mmol) in anhydrous CH$_2$Cl$_2$ (2.2 mL) was stirred at room temperature for 12 h to give a suspension containing white solids. The suspension was concentrated under reduced pressure and washed with MeOH. The residual solids were collected by centrifugation, rinsed successively with CH$_2$Cl$_2$ and EtOAc, and dried in vacuo to give compound I-e-8 (72 mg, 82% yield). C$_{22}$H$_{20}$N$_4$O$_4$S$_2$; white solid; TLC (CH$_2$Cl$_2$/MeOH=30:1) R$_f$=0.1; $^1$H NMR (400 MHz, DMSO-d$_6$); δ 7.99 (2H, d, J=8.0 Hz), 7.88 (2H, d, J=8.0 Hz), 7.70 (2H, t, J=7.6 Hz), 7.43 (2H, t, J=7.6 Hz), 4.80-4.82 (4H, m), 3.63 (2H, br s), 3.57 (4H, br s), 3.48 (2H, br s); $^{13}$C NMR (100 MHz, CDCl$_3$) δ 165.2 (2×), 165.0 (2×), 141.4 (2×), 132.0 (2×), 125.7 (2×), 125.4 (2×), 123.5 (2×), 121.7 (2×), 44.5 (2×), 44.0 (2×); ESI-HRMS calcd for C$_{22}$H$_{21}$N$_4$O$_4$S$_2$: 469.1004. found: m/z 469.1003 [M+H]$^+$.

2-(2-Oxo-2-(piperazin-1-yl)ethyl)benzo[d]isothiazol-3(2H)-one (I-f-1)

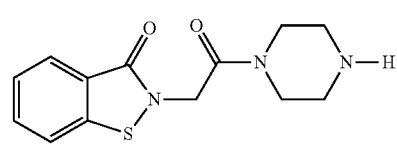

I-f-1

Tert-butyl 4-(2-(3-oxobenzo[d]isothiazol-2(3H)-yl)acetyl)piperazine-1-carboxylate (I-d-2) (50 mg, 0.13 mmol) and TFA (2 mL, 26.1 mmol) were dissolved in CH$_2$Cl$_2$ (15 mL) and stirred at room temperature for 1 h. TFA was removed under reduced pressure; the residue was extracted with CHCl$_3$ and ammonia solution (35%). The combined organic phase was dried over MgSO$_4$, filtered, and concentrated under reduced pressure to provide the product I-f-1 (36.5 mg, 99% yield). C$_{13}$H$_{15}$N$_3$O$_2$S; white solid; mp 157-159° C.; $^1$H NMR (400 MHz, CD$_3$OD) δ 7.98 (1H, dt, J=7.9, 0.8 Hz), 7.82-7.79 (1H, m), 7.73-7.69 (1H, m), 7.47 (1H, td, J=7.9, 1.1 Hz), 4.82 (2H, s), 3.59-3.55 (4H, m), 2.88 (2H, t, J=5.1 Hz), 2.82 (2H, t, J=5.1 Hz); $^{13}$C NMR (100 MHz, CDCl$_3$) δ 165.6, 164.9, 141.4, 132.0, 126.6, 125.3, 123.3, 120.2, 46.3, 46.0, 45.6, 44.7, 43.1; ESI-HRMS calcd for C$_{13}$H$_{16}$N$_3$O$_2$S: 278.0963. found m/z 278.0958 [M+H]$^+$.

6-Bromo-2-(2-oxo-2-(piperazin-1-yl)ethyl)benzo[d]isothiazol-3(2H)-one (I-f-2)

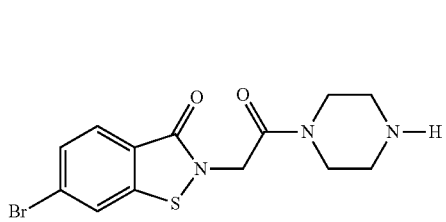

I-f-2

Tert-butyl 4-(2-(6-bromo-3-oxobenzo[d]isothiazol-2(3H)-yl)acetyl)piperazine-1-carboxylate (I-d-10) (56 mg, 0.12 mmol) and TFA (1.5 mL) was dissolved in $CH_2Cl_2$ (10 mL), and then stirred for 2 h at 25° C. TFA was removed under reduced pressure, and gave compound I-f-2 (22 mg; 50%). $C_{13}H_{14}N_3O_2SBr$; yellow foaming solid; $^1H$ NMR (400 MHz, $CD_3OD$) δ 8.00 (2H, d, J=1.6 Hz), 7.79 (1H, d, J=8.4 Hz), 7.55 (1H, dd, J=8.4, 1.6 Hz), 4.77 (2H, s), 3.76 (5H, m), 3.16 (3H, s); $^{13}C$ NMR (100 MHz, $CD_3OD$) δ 167.4, 167.2, 145.1, 130.5, 128.5, 128.3, 125.3, 123.9, 45.9 (2×), 44.5, 43.2, 40.3; ESI-HRMS calcd for $C_{13}H_{15}N_3O_2SBr$: 356.0068. found: m/z 356.0070 $[M+H]^+$.

6-Azido-2-(2-oxo-2-(piperazin-1-yl)ethyl)benzo[d]isothiazol-3(2H)-one (I-f-3)

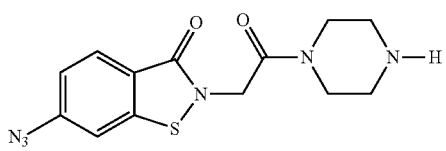

I-f-3

Tert-butyl 4-(2-(6-azido-3-oxobenzo[d]isothiazol-2(3H)-yl)acetyl)piperazine-1-carboxylate (I-d-14) (140 mg, 0.34 mmol) and TFA (5.1 mL, 67 mmol) was dissolved in $CH_2Cl_2$ (20 mL), and then stirred for 0.5 h at 25° C. TFA was removed under reduced pressure, and compound I-f-3 (127 mg; 87%) was obtained. $C_{13}H_{14}N_6O_2S$; light yellow oil; IR $v_{max}$ (neat) 2910, 2851, 2130, 1683, 1653, 1472, 1201, 1130, 721, 672 $cm^{-1}$; $^1H$ NMR (400 MHz, $CD_3OD$) δ 7.95 (1H, d, J=8.4 Hz), 7.53 (1H, d, J=2.0 Hz), 7.15 (1H, dd, J=8.4, 2.0 Hz), 4.84 (2H, s), 3.86-3.84 (4H, m), 3.35-3.30 (2H, m), 3.26 (2H, m); $^{13}C$ NMR (100 MHz, $CD_3OD$) δ 167.4 (2×), 146.6, 145.3, 128.7, 121.7, 118.8, 112.0, 45.9 (2×), 44.4, 43.1, 40.2; ESI-HRMS calcd for $C_{13}H_{15}N_6O_2S$: 319.0977. found: m/z 319.0977 $[M+H]^+$.

Example 5

In Vitro Activity of TMPK Inhibitor Derivatives

The in vitro inhibitory activities of test compounds (at 2 μM concentration) against human TMPK are shown in Table 3 and compared with that of YMU1 and YMU2.

YMU1

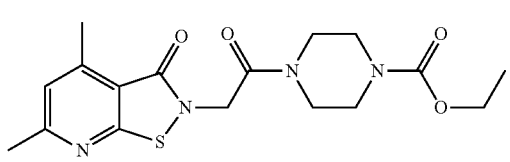

YMU2

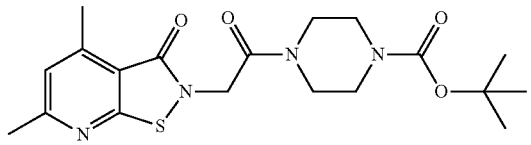

TABLE 3

| Compound | Inhibition (%) |
| --- | --- |
| YMU1 | 42 ± 15 |
| YMU2 | 46 ± 2 |
| I-a-1 | 77 ± 4 |
| I-a-2 | 80 ± 10 |
| I-a-3 | 16 ± 5 |
| I-a-4 | 10 ± 7 |
| I-a-5 | 93 ± 9 |
| I-b-1 | 54 ± 7 |
| I-b-2 | 32 ± 2 |
| I-b-3 | 29 ± 3 |
| I-b-4 | 32 ± 2 |
| I-b-5 | 79 ± 12 |
| I-b-6 | 48 ± 5 |
| I-c-1 | 75 ± 11 |
| I-c-2 | 46 ± 2 |
| I-c-3 | 6 ± 5 |
| I-d-1 | 79 ± 5 |
| I-d-2 | 100 ± 9 |
| I-d-3 | 54 ± 1 |
| I-d-5 | 56 ± 4 |
| I-d-6 | 87 ± 5 |
| I-d-7 | 66 ± 7 |
| I-d-8 | 25 ± 3 |
| I-d-9 | 55 ± 7 |
| I-d-10 | 56 ± 0 |
| I-d-11 | 86 ± 6 |
| I-d-12 | 84 ± 1 |
| I-d-13 | 39 ± 14 |
| I-d-14 | 66 ± 5 |
| I-d-15 | 51 ± 9 |
| I-d-16 | 22 ± 12 |
| I-d-17 | 80 ± 4 |
| I-d-18 | 78 ± 7 |
| I-e-1 | 31 ± 5 |
| I-e-4 | 63 ± 10 |
| I-e-5 | 100 ± 7 |
| I-e-6 | 55 ± 7 |
| I-e-7 | 50 ± 5 |
| I-e-8 | 89 ± 6 |
| I-f-1 | 34 ± 2 |
| I-f-2 | 38 ± 14 |

In one embodiment, the $IC_{50}$ values were determined by enzymatic assay. The test compounds inhibited human TMPK with the $IC_{50}$ values in micro- and submicromolar range: YMU1, 2.21±0.06 μM; I-a-5, 0.5 μM; I-b-1, 1.81±0.28 μM; I-b-4, 0.8 μM; I-b-6, 1.1 μM; I-e-5, 1.29±0.20 μM; I-e-5, 1.73±0.05 μM; I-e-8, 0.45 μM.

In one embodiment, the inhibitory mode of test compound was determined by pre-incubating different concentrations of test compound with purified hTMPK protein and measuring initial velocity using the conventional TMPK assay. The values of $K_m$ and $V_{max}$ were determined using a non-linear regression analysis.

For determination of inhibition constant ($K_i$ value), the inhibitor at the indicated concentration was pre-incubated with 0.5 μg of purified hTMPK protein for 10 min, and the initial velocity of the TMPK reaction was measured in the presence of ATP (1 mM) and different concentrations of TMP (2-200 μM) or in the presence of TMP (200 μM) and different concentrations of ATP (5-1000 μM) using NADH-coupled TMPK assay as described in the Methods of the Invention section. The $K_i$ value was calculated from an equation of $$K_i=[I]/(V_{max}/V_{max}^I-1)$$

wherein [I] is the concentration of inhibitor, and $V_{max}^I$ is the maximal velocity in the presence of inhibitor.

In one embodiments, YMU1 and I-b-5 exhibited $K_i$ values of 0.22±0.03 μM and 0.17±0.07 μM, respectively.

In one embodiment, compounds YMUI and I-d-2 at 2 μM had 30-fold enhancement on doxorubicin sensitization in MDA-MB231 cell treatment.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

REFERENCES

Agarwal, K. C., Miech, R. P., and Parks, R. E., Jr. (1978). Guanylate kinases from human erythrocytes, hog brain, and rat liver. Methods Enzymol 51, 483-490.

Ahmad, S. I., Kirk, S. H., and Eisenstark, A. (1998). Thymine metabolism and thymineless death in prokaryotes and eukaryotes. Annu Rev Microbiol 52, 591-625.

Bessman, M. J., Lehman, I. R., Adler, J., Zimmerman, S. B., Simms, E. S., and Kornberg, A. (1958). Enzymatic Synthesis of Deoxyribonucleic Acid. Iii. The Incorporation of Pyrimidine and Purine Analogues into Deoxyribonucleic Acid. Proc Natl Acad Sci USA 44, 633-640.

Bolderson, E., Richard, D. J., Zhou, B. B., and Khanna, K. K. (2009). Recent advances in cancer therapy targeting proteins involved in DNA double-strand break repair. Clin Cancer Res 15, 6314-6320.

Bunz, F., Dutriaux, A., Lengauer, C., Waldman, T., Zhou, S., Brown, J. P., Sedivy, J. M., Kinzler, K. W., and Vogelstein, B. (1998). Requirement for p53 and p21 to sustain G2 arrest after DNA damage. Science 282, 1497-1501.

Burkhalter, M. D., Roberts, S. A., Havener, J. M., and Ramsden, D. A. (2009). Activity of ribonucleotide reductase helps determine how cells repair DNA double strand breaks. DNA Repair (Amst) 8, 1258-1263.

Chang, Z. F., Huang, D. Y., and Chi, L. M. (1998). Serine 13 is the site of mitotic phosphorylation of human thymidine kinase. J Biol Chem 273, 12095-12100.

Chang, Z. F., Huang, D. Y., and Hsue, N. C. (1994). Differential phosphorylation of human thymidine kinase in proliferating and M phase-arrested human cells. J Biol Chem 269, 21249-21254.

Cory, A. H., Owen, T. C., Barltrop, J. A., and Cory, J. G. (1991). Use of an aqueous soluble tetrazolium/formazan assay for cell growth assays in culture. Cancer Commun 3, 207-212.

Ferraro, P., Franzolin, E., Pontarin, G., Reichard, P., and Bianchi, V. (2010). Quantitation of cellular deoxynucleoside triphosphates. Nucleic Acids Res 38, e85.

Garg, D., Henrich, S., Salo-Ahen, O. M., Myllykallio, H., Costi, M. P., and Wade, R. C. (2010). Novel approaches for targeting thymidylate synthase to overcome the resistance and toxicity of anticancer drugs. J Med Chem 53, 6539-6549.

Helleday, T., Petermann, E., Lundin, C., Hodgson, B., and Sharma, R. A. (2008). DNA repair pathways as targets for cancer therapy. Nat Rev Cancer 8, 193-204.

Hu, C. M., and Chang, Z. F. (2008). Synthetic lethality by lentiviral short hairpin RNA silencing of thymidylate kinase and doxorubicin in colon cancer cells regardless of the p53 status. Cancer Res 68, 2831-2840.

Hu, C. M., and Chang, Z. F. (2010). A bioluminescent method for measuring thymidylate kinase activity suitable for high-throughput screening of inhibitor. Anal Biochem 398, 269-271.

Hu, C M, Yeh, M T, Chen C W, Tsao N, Gao, Q Z, Chang, C Y, Lee M H, Fang J M, Sheu S Y and Lin C J, Tseng M C, Chen Y J, Chang Z F. Tumor cells require thymidylate kinase to prevent dUTP incorporation during DNA repair. Cancer Cell 22, 36-50, 2012 (selected for preview in the issue).

Huang, S. H., Tang, A., Drisco, B., Zhang, S. Q., Seeger, R., Li, C., and Jong, A. (1994). Human dTMP kinase: gene expression and enzymatic activity coinciding with cell cycle progression and cell growth. DNA Cell Biol 13, 461-471.

Jackson, S. P., and Bartek, J. (2009). The DNA-damage response in human biology and disease. Nature 461, 1071-1078.

Jensen, R. A., Page, D. L., and Holt, J. T. (1994). Identification of genes expressed in premalignant breast disease by microscopy-directed cloning. Proc Natl Acad Sci USA 91, 9257-9261.

Jiang, H., Reinhardt, H. C., Bartkova, J., Tommiska, J., Blomqvist, C., Nevanlinna, H., Bartek, J., Yaffe, M. B., and Hemann, M. T. (2009). The combined status of ATM and p53 link tumor development with therapeutic response. Genes Dev 23, 1895-1909.

Kastan, M. B., and Bartek, J. (2004). Cell-cycle checkpoints and cancer. Nature 432, 316-323.

Ke, P. Y., Kuo, Y. Y., Hu, C. M., and Chang, Z. F. (2005). Control of dTTP pool size by anaphase promoting complex/cyclosome is essential for the maintenance of genetic stability. Genes Dev 19, 1920-1933.

Ladner, R. D., and Caradonna, S. J. (1997). The human dUTPase gene encodes both nuclear and mitochondrial isoforms. Differential expression of the isoforms and characterization of a cDNA encoding the mitochondrial species. J Biol Chem 272, 19072-19080.

Longley, D. B., Harkin, D. P., and Johnston, P. G. (2003). 5-fluorouracil: mechanisms of action and clinical strategies. Nat Rev Cancer 3, 330-338.

Mimeault, M., Hauke, R., and Batra, S. K. (2008). Recent advances on the molecular mechanisms involved in the drug resistance of cancer cells and novel targeting therapies. Clin Pharmacol Ther 83, 673-691.

Miyata, S., Oshima, K., Kakizawa, S., Nishigawa, H., Jung, H. Y., Kuboyama, T., Ugaki, M., and Namba, S. (2003). Two different thymidylate kinase gene homologues, including one that has catalytic activity, are encoded in the onion yellows phytoplasma genome. Microbiology 149, 2243-2250.

Mosbaugh, D. W. (1988). Purification and characterization of porcine liver DNA polymerase gamma: utilization of dUTP and dTTP during in vitro DNA synthesis. Nucleic Acids Res 16, 5645-5659.

Nordlund, P., and Reichard, P. (2006). Ribonucleotide reductases. Annu Rev Biochem 75, 681-706.

Okumura, H., Natsugoe, S., Matsumoto, M., Mataki, Y., Takatori, H., Ishigami, S., Takao, S., and Aikou, T. (2005). The predictive value of p53, p53R2, and p21 for the effect of chemoradiation therapy on oesophageal squamous cell carcinoma. Br J Cancer 92, 284-289.

Ostermann, N., Segura-Pena, D., Meier, C., Veit, T., Monnerjahn, C., Konrad, M., and Lavie, A. (2003). Structures of human thymidylate kinase in complex with prodrugs: implications for the structure-based design of novel compounds. Biochemistry 42, 2568-2577.

Robert, T., Vanoli, F., Chiolo, I., Shubassi, G., Bernstein, K. A., Rothstein, R., Botrugno, O. A., Parazzoli, D., Oldani, A., Minucci, S., and Foiani, M. (2011). HDACs link the DNA damage response, processing of double-strand breaks and autophagy. Nature 471, 74-79.

San Filippo, J., Sung, P., and Klein, H. (2008). Mechanism of eukaryotic homologous recombination. Annu Rev Biochem 77, 229-257.

Yanamoto, S., Kawasaki, G., Yoshitomi, I., and Mizuno, A. (2003). Expression of p53R2, newly p53 target in oral normal epithelium, epithelial dysplasia and squamous cell carcinoma. Cancer Lett 190, 233-243.

Yang, T. C., Georgy, K. A., Tavakoli, A., Craise, L. M., and Durante, M. (1996). Radiogenic transformation of human mammary epithelial cells in vitro. Radiat Oncol Investig 3, 412-419.

Zhang, K., Hu, S., Wu, J., Chen, L., Lu, J., Wang, X., Liu, X., Zhou, B., and Yen, Y. (2009). Overexpression of RRM2 decreases thrombspondin-1 and increases VEGF production in human cancer cells in vitro and in vivo: implication of RRM2 in angiogenesis. Mol Cancer 8, 11.

What is claimed:

1. A compound of Formula (I):

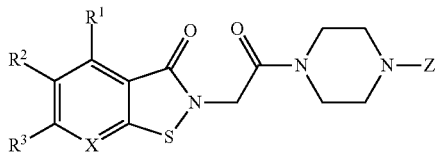

or a pharmaceutically acceptable salt thereof,
wherein
X is independently N or $CR^4$;
Z is H or Y-G
wherein
Y is —C(=O)O or —C(=O)$CH_2$;
G is optionally substituted alkyl, optionally substituted alkenyl, optionally substituted alkynyl, optionally substituted carbocyclyl, optionally substituted aryl, optionally substituted heterocyclyl, optionally substituted heteroaryl, —$NHR^B$, —NHC(=O)$NHR^B$, —N=C=O, or —N=C=S;
$R^1$, $R^2$, $R^3$ and $R^4$ is independently hydrogen, halogen, —CN, —$NO_2$, —$N_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$SR^A$, —$NHR^B$, —N($R^B$)$_2$, —C(=O)$R^A$, —C(=O)$OR^A$, —OC(=O)$R^A$, —O$CH_2$C(=O)N($R^B$)$_2$, —C(=O)$NHR^B$, —C(=O)N($R^B$)$_2$, —$NR^B$C(=O)$R^A$, —OC(=O)N($R^B$)$_2$, $NR^B$C(=O)$OR^A$, —$NR^B$C(=O)N($R^B$)$_2$, —S(=O)$R^A$, —OS(=O)$_2R^A$, —$SO_2R^A$, —$NR^B SO_2R^A$, —$SO_2$N($R^B$)$_2$, or optionally substituted triazole;
wherein
$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;
$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

or two $R^B$ taken together with the intervening nitrogen form optionally substituted heterocyclyl;
providing
Z is not —C(=O)$OC_2H_5$ or —C(=O)OC($CH_3$)$_3$ when X, $R^1$, $R^2$, $R^3$ are simultaneously N, $CH_3$, H and $CH_3$, respectively.

2. The compound of claim 1, wherein the compound is of Formula (I-a):

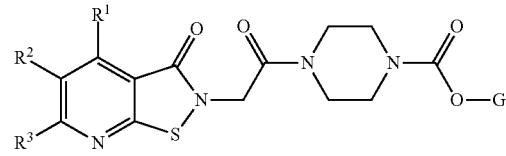

or a pharmaceutically acceptable salt thereof,
wherein
G, $R^1$, $R^2$ and $R^3$ are defined as that in claim 1.

3. The compound of claim 1, wherein the compound is of Formula (I-b):

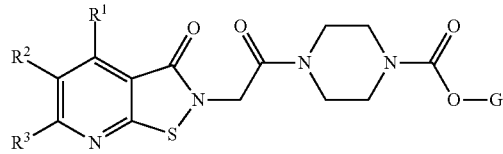

or a pharmaceutically acceptable salt thereof,
wherein
G, $R^1$, $R^2$ and $R^3$ are defined as that in claim 1.

4. The compound of claim 1, wherein the compound is of Formula (I-c):

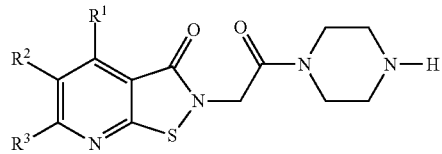

or a pharmaceutically acceptable salt thereof, wherein

R$^1$, R$^2$ and R$^3$ are defined as that in claim 1.

5. The compound of claim 1, wherein the compound is of Formula (I-d):

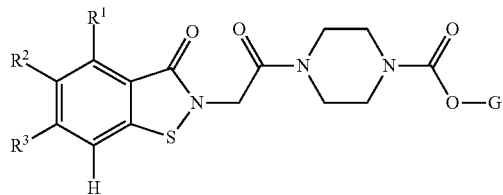

(I-d)

or a pharmaceutically acceptable salt thereof,
wherein

G, R$^1$, R$^2$ and R$^3$ are defined as that in claim 1.

6. The compound of claim 1, wherein the compound is of Formula (I-e):

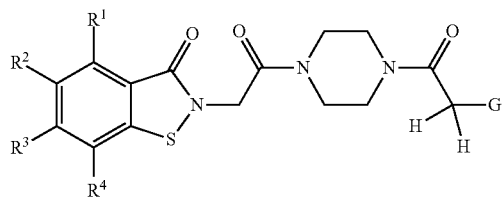

(I-e)

or a pharmaceutically acceptable salt thereof,
wherein

G, R$^1$, R$^2$ and R$^3$ are defined as that in claim 1.

7. The compound of claim 1, wherein the compound is of Formula (I-f):

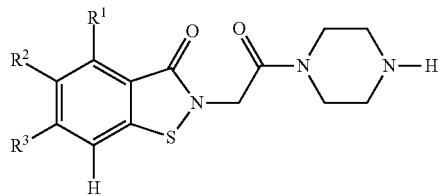

(I-f)

or a pharmaceutically acceptable salt thereof,
wherein

R$^1$, R$^2$ and R$^3$ are defined as that in claim 1.

8. The compound of claim 1, wherein the compound is one of the following:

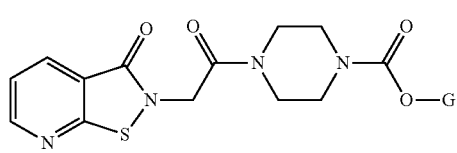

wherein G is C$_n$H$_{2n+1}$, CH$_2$Ph, CH$_2$CH=CH$_2$; wherein n=1-6; or

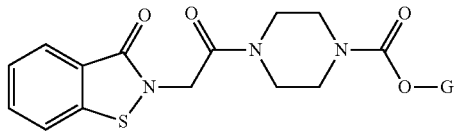

wherein G is C$_n$H$_{2n+1}$, CH$_2$Ph, CH$_2$CH=CH$_2$; wherein n=1-6; or

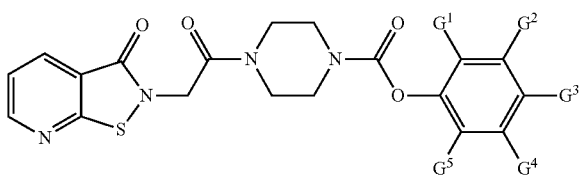

wherein G$^1$, G$^2$, G$^3$, G$^4$ and G$^5$ is independently F, Cl, Br, I, CN, NO$_2$, N$_3$, C$_n$H$_{2n+1}$, OC$_n$H$_{2n+1}$, SC$_n$H$_{2n+1}$, NHC$_n$H$_{2n+1}$, N(C$_n$H$_{2n+1}$)$_2$, O(C=O)C$_n$H$_{2n+1}$, NH(C=O)C$_n$H$_{2n+1}$, C(=O)C$_n$H$_{2n+1}$, C(=O)OC$_n$H$_{2n+1}$, C(=O)NHC$_n$H$_{2n+1}$, SO$_2$C$_n$H$_{2n+1}$; wherein n=0-4; or

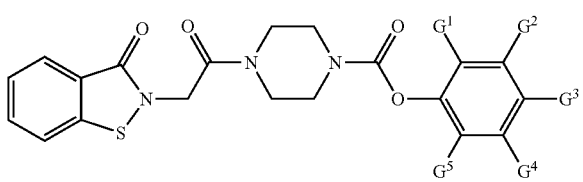

wherein G$^1$, G$^2$, G$^3$, G$^4$ and G$^5$ is independently F, Cl, Br, I, CN, NO$_2$, N$_3$, C$_n$H$_{2n+1}$, OC$_n$H$_{2n+1}$, SC$_n$H$_{2n+1}$, NHC$_n$H$_{2n+1}$, N(C$_n$H$_{2n+1}$)$_2$, O(C=O)C$_n$H$_{2n+1}$, NH(C=O)C$_n$H$_{2n+1}$, C(=O)C$_n$H$_{2n+1}$, C(=O)OC$_n$H$_{2n+1}$, C(=O)NHC$_n$H$_{2n+1}$, SO$_2$C$_n$H$_{2n+1}$; wherein n=0-4; or

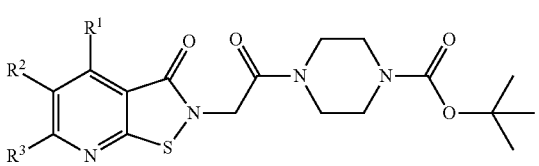

wherein R$^1$, R$^2$ and R$^3$ is independently F, Cl, Br, I, CN, NO$_2$, N$_3$, C$_n$H$_{2n+1}$, OC$_n$H$_{2n+1}$, SC$_n$H$_{2n+1}$, NHC$_n$H$_{2n+1}$, N(C$_n$H$_{2n+1}$)$_2$, O(C=O)C$_n$H$_{2n+1}$, NH(C=O)C$_n$H$_{2n+1}$, C(=O)C$_n$H$_{2n+1}$, C(=O)OC$_n$H$_{2n+1}$, C(=O)NHC$_n$H$_{2n+1}$, SO$_2$C$_n$H$_{2n+1}$; wherein n=0-4; or

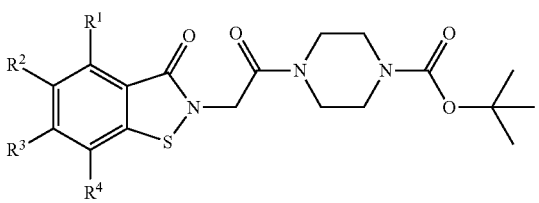

wherein $R^1$, $R^2$, $R^3$ and $R^4$ is independently F, Cl, Br, I, CN, $NO_2$, $N_3$, $C_nH_{2n+1}$, $OC_nH_{2n+1}$, $OSi(C_nH_{2n+1})_3$, $OSiMe_2(t\text{-}Bu)$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$;

wherein n=0-4; or

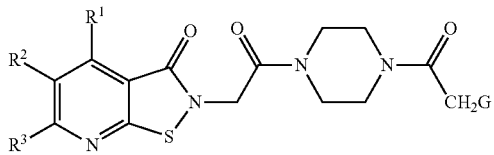

wherein $R^1$, $R^2$ and $R^3$ is independently F, Cl, Br, I, $N_3$, $C_nH_{2n+1}$, $OC_nH_{2n+1}$, $NHC_nH_{2n+1}$, $N(C_nH_{2n+1})_2$; G is F, Cl, Br, I, $N_3$, $NH_2$, N=C=S, N=C=O, $NH(C=O)C_nH_{2n+1}$, $NH(C=O)Ar$, $NH(C=O)OC_nH_{2n+1}$, $NH(C=O)OAr$, $NH(C=O)NHC_nH_{2n+1}$, $NH(C=O)NHAr$;

wherein Ar is optionally substituted phenyl; n=0-4; or

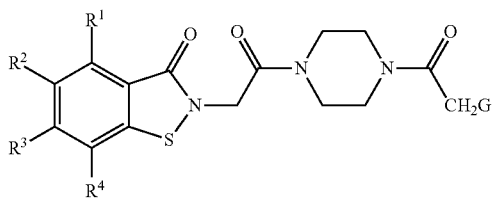

wherein $R^1$, $R^2$, $R^3$ and $R^4$ is independently F, Cl, Br, I, $N_3$, $C_nH_{2n+1}$, $OC_nH_{2n+1}$, $NHC_nH_{2n+1}$, $N(C_nH_{2n+1})_2$;
G is F, Cl, Br, I, $N_3$, $NH_2$, N=C=S, N=C=O, $NH(C=O)C_nH_{2n+1}$, $NH(C=O)Ar$, $NH(C=O)OC_nH_{2n+1}$, $NH(C=O)OAr$, $NH(C=O)NHC_nH_{2n+1}$, $NH(C=O)NHAr$;

wherein Ar is optionally substituted phenyl; n=0-4; or

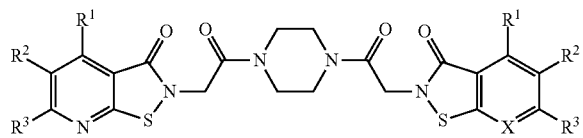

wherein X is N or $CR^4$;
$R^1$, $R^2$, $R^3$ and $R^4$ is independently F, Cl, Br, I, $N_3$, $C_nH_{2n+1}$, $OC_nH_{2n+1}$, $NHC_nH_{2n+1}$, $N(C_nH_{2n+1})_2$;
wherein n=0-4; or

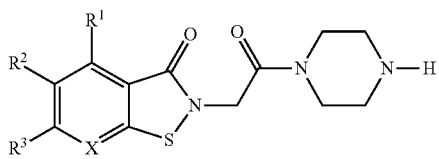

wherein
X is N or CH;
$R^1$, $R^2$ and $R^3$ is independently F, Cl, Br, I, CN, $NO_2$, $N_3$, $C_nH_{2n+1}$, $OC_nH_{2n+1}$, $OSi(C_nH_{2n+1})_3$, $OSiMe_2(t\text{-}Bu)$, $SC_nH_{2n+1}$, $NHC_nH_{2n+1}$, $N(C_nH_{2n+1})_2$, $O(C=O)C_nH_{2n+1}$, $NH(C=O)C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$;

wherein n=0-4; or

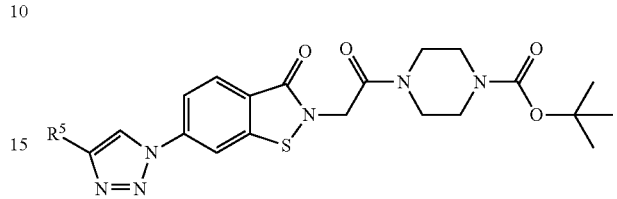

wherein $R^5$ is $C_nH_{2n+1}$, $C(=O)C_nH_{2n+1}$, $C(=O)OC_nH_{2n+1}$, $C(=O)NHC_nH_{2n+1}$, $SO_2C_nH_{2n+1}$ or optionally substituted phenyl; wherein n=0-4.

9. The compound of claim 2, wherein the Formula (I-a) is one of the following:

I-a-1

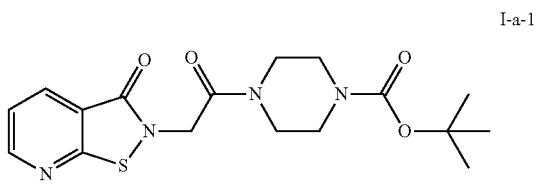

I-a-2

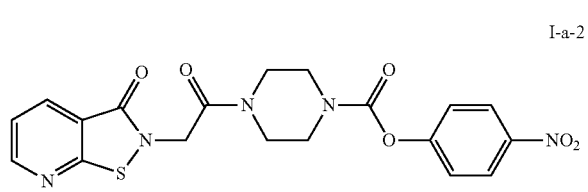

I-a-3

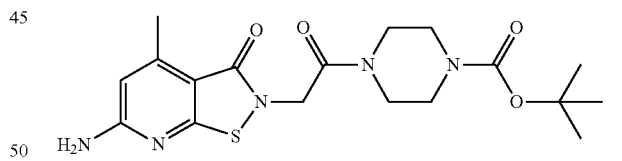

I-a-4

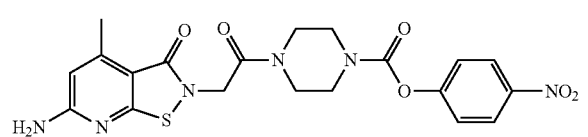

I-a-5

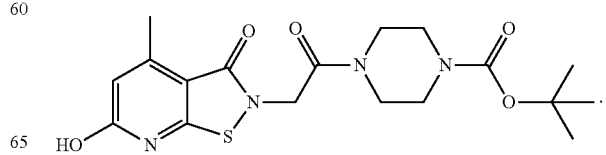

10. The compound of claim 3, wherein the Formula (I-b) is one of the following:
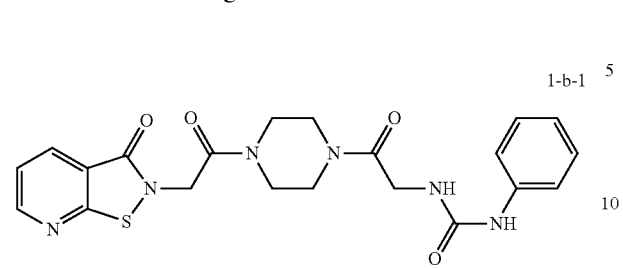
I-b-1
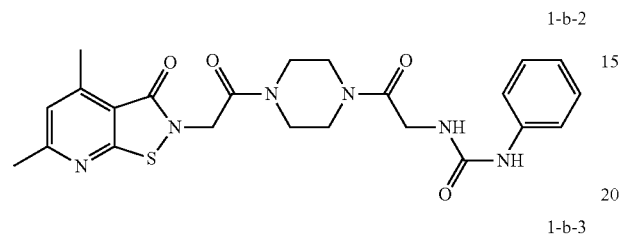
I-b-2
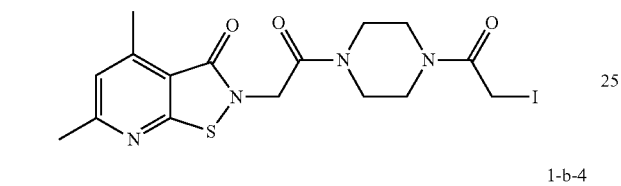
I-b-3
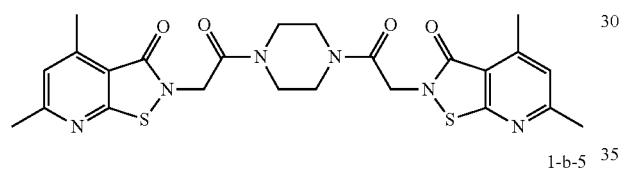
I-b-4
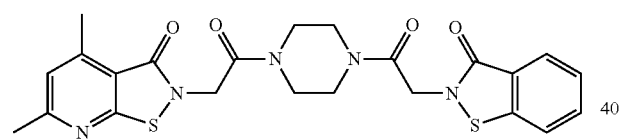
I-b-5
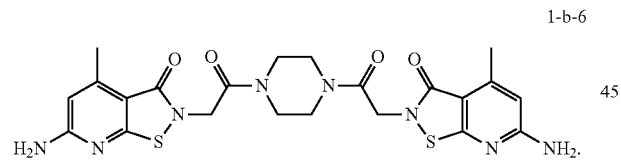
I-b-6
11. The compound of claim 4, wherein Formula (I-c) is one of the following:
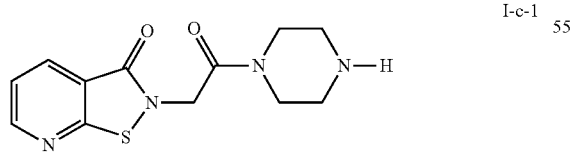
I-c-1
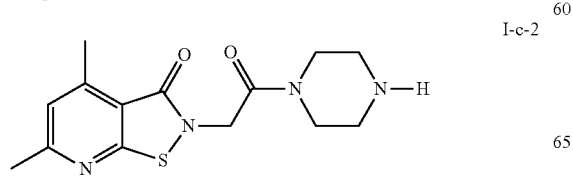
I-c-2
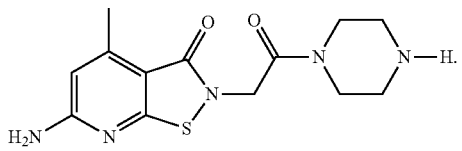
I-c-3
12. The compound of claim 5, wherein the Formula (I-d) is one of the following:
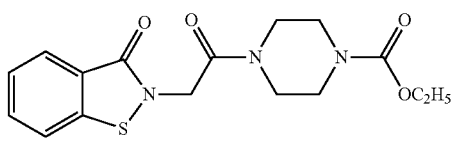
I-d-1
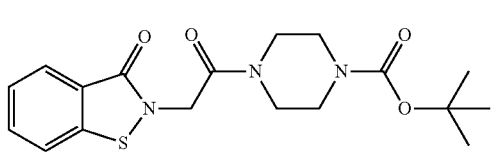
I-d-2
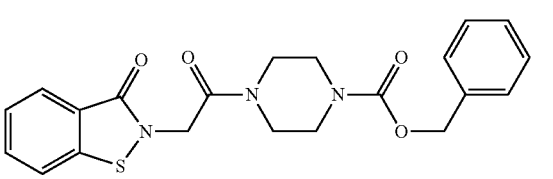
I-d-3
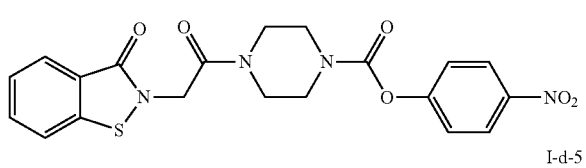
I-d-4
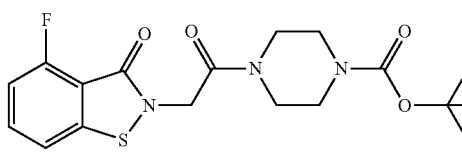
I-d-5
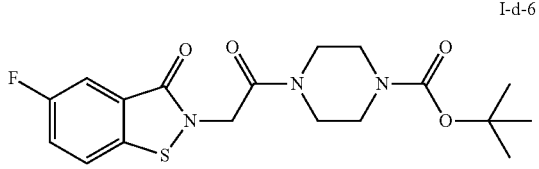
I-d-6
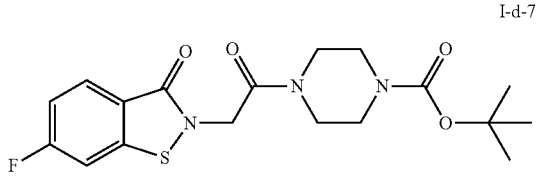
I-d-7

I-d-8
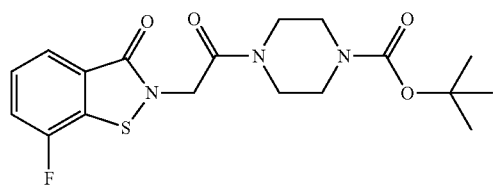
I-d-9
I-d-10
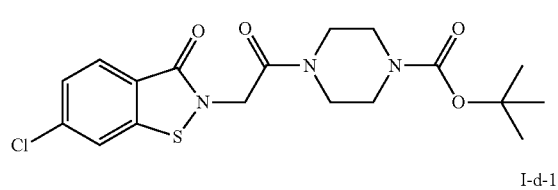
I-d-11
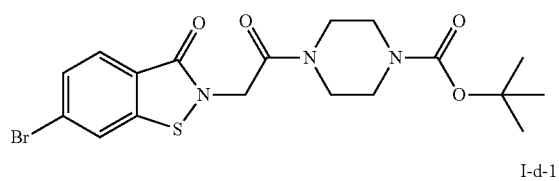
I-d-12
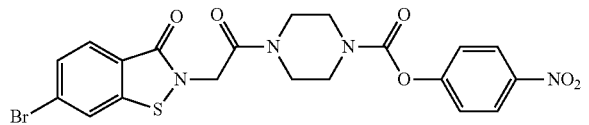
I-d-13
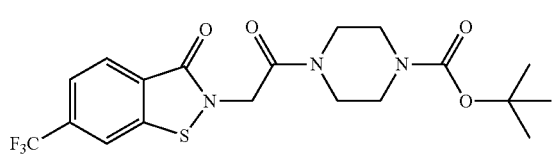
I-d-14
I-d-15
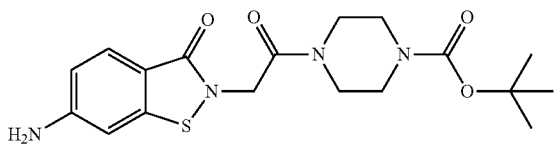
I-d-16
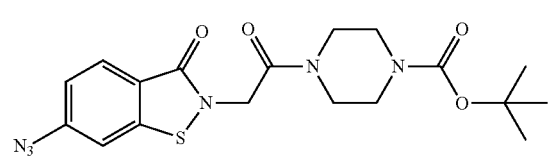
I-d-17
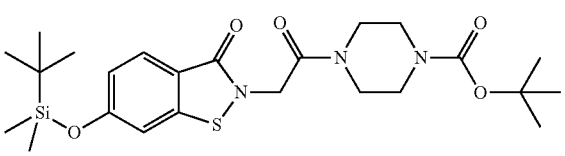
I-d-18
I-d-19
13. The compound of claim 6, wherein the Formula (I-e) is one of the following:
I-e-1
I-e-2
I-e-3
I-e-4
I-e-5

-continued

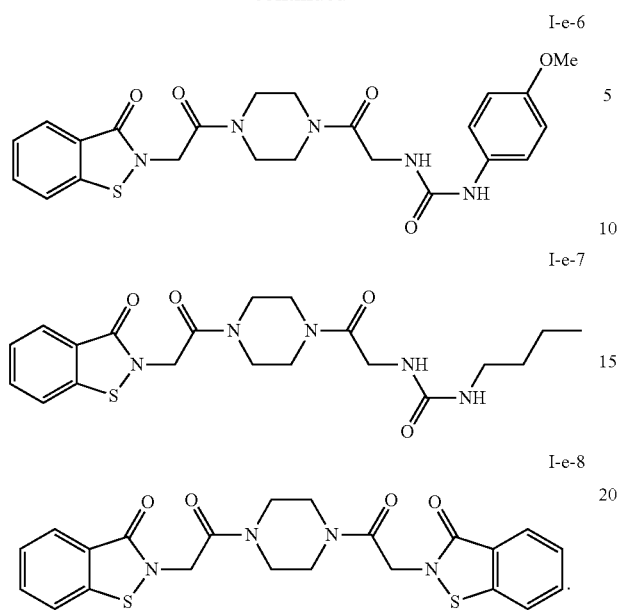

I-e-6
I-e-7
I-e-8

14. The compound of claim 7, wherein the Formula (I-f) is one of the following:

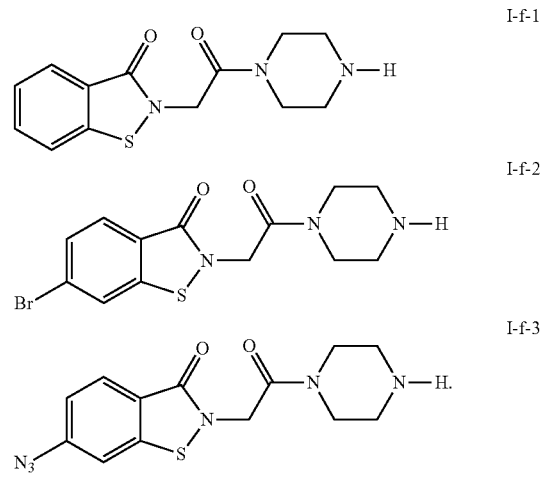

I-f-1
I-f-2
I-f-3

15. A pharmaceutical composition comprising a compound of claim 1 or a pharmaceutically acceptable salt thereof, and a pharmaceutically acceptable carrier.

16. A method for inhibiting thymidylate kinase (TMPK) activity comprising contacting a cell with an effective amount of a compound of claim 1.

* * * * *

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: LacZ shRNA targeting sequence

<400> SEQUENCE: 1
ctacacaaat cagcgattt                                                 19

<210> SEQ ID NO 2
<211> LENGTH: 19
<212> TYPE: DNA
<213> ORGANISM: Artificial Sequence
<220> FEATURE:
<223> OTHER INFORMATION: TMPK shRNA targeting sequence

<400> SEQUENCE: 2
acacgacttt gaactggaa                                                 19

<210> SEQ ID NO 3
<211> LENGTH: 20
<212> TYPE: DNA
<213> ORGANISM: Artificial Sequence
<220> FEATURE:
<223> OTHER INFORMATION: TS shRNA targeting sequence

<400> SEQUENCE: 3
ggatattgtc agtctttagg                                                20

<210> SEQ ID NO 4
<211> LENGTH: 18
<212> TYPE: DNA
<213> ORGANISM: Artificial Sequence
<220> FEATURE:
<223> OTHER INFORMATION: R2 siRNA targeting sequence
```

```
<400> SEQUENCE: 4
accggaaaag aaaatgct                                              18

<210> SEQ ID NO 5
<211> LENGTH: 19
<212> TYPE: DNA
<213> ORGANISM: Artificial Sequence
<220> FEATURE:
<223> OTHER INFORMATION: GAPDH primer

<400> SEQUENCE: 5
ccaggggtgc taagcagtt                                             19
```